(12) United States Patent
Goldring et al.

(10) Patent No.: US 9,562,848 B2
(45) Date of Patent: Feb. 7, 2017

(54) SPECTROMETRY SYSTEMS, METHODS, AND APPLICATIONS

(71) Applicant: VERIFOOD, LTD., Herzliya (IL)

(72) Inventors: Damian Goldring, Tel-Aviv (IL); Dror Sharon, Benei Atarot (IL); Guy Brodetzki, Rehovot (IL); Amit Ruf, Hod HaSharon (IL); Menahem Kaplan, Tel-Aviv (IL); Sagee Rosen, Netzer Sireni (IL); Omer Keilaf, Kfar Saba (IL); Uri Kinrot, Hod HaSharon (IL); Kai Engelhardt, Buckenhof (DE); Ittai Nir, Tel-Aviv (IL); Nitzan Waisberg, Tel-Aviv (IL); Dana Cohen Bar-On, Kfar-Saba (IL)

(73) Assignee: VERIFOOD, LTD., Herzliya (IL)

( * ) Notice: Subject to any disclaimer, the term of this patent is extended or adjusted under 35 U.S.C. 154(b) by 0 days.

(21) Appl. No.: 15/183,114

(22) Filed: Jun. 15, 2016

(65) Prior Publication Data

US 2016/0299061 A1    Oct. 13, 2016

Related U.S. Application Data

(63) Continuation of application No. PCT/IL2015/050002, filed on Jan. 1, 2015.
(Continued)

(51) Int. Cl.
*G01J 3/00*     (2006.01)
*G01N 21/31*    (2006.01)

(52) U.S. Cl.
CPC ....... *G01N 21/31* (2013.01); *G01N 2201/0221* (2013.01)

(58) Field of Classification Search
CPC .......... G01N 21/31; G01N 21/552; G01J 3/02; G01J 3/28; G01J 3/42; G01J 3/10
See application file for complete search history.

(56) References Cited

U.S. PATENT DOCUMENTS

| 679,577 A | 7/1901 | Henry |
| 5,469,252 A | 11/1995 | Doles et al. |

(Continued)

FOREIGN PATENT DOCUMENTS

| WO | WO-9953350 A1 | 10/1999 |
| WO | WO-2010027982 A2 | 3/2010 |

(Continued)

OTHER PUBLICATIONS

Acktar Advanced Coatings Website. Accessed Jun. 3, 2015. http://www.acktar.com/.
(Continued)

*Primary Examiner* — Abdullahi Nur
(74) *Attorney, Agent, or Firm* — Wilson Sonsini Goodrich & Rosati

(57) ABSTRACT

A hand held spectrometer is used to illuminate the object and measure the one or more spectra. The spectral data of the object can be used to determine one or more attributes of the object. In many embodiments, the spectrometer is coupled to a database of spectral information that can be used to determine the attributes of the object. The spectrometer system may comprise a hand held communication device coupled to a spectrometer, in which the user can input and receive data related to the measured object with the hand held communication device. The embodiments disclosed herein allow many users to share object data with many people, in order to provide many people with actionable intelligence in response to spectral data.

20 Claims, 35 Drawing Sheets

Related U.S. Application Data

(60) Provisional application No. 61/923,422, filed on Jan. 3, 2014, provisional application No. 61/985,447, filed on Apr. 28, 2014.

(56) References Cited

U.S. PATENT DOCUMENTS

| | | | |
|---|---|---|---|
| 6,031,233 | A | 2/2000 | Levin et al. |
| 6,031,619 | A | 2/2000 | Wilkens et al. |
| 6,212,312 | B1 | 4/2001 | Grann et al. |
| 6,483,583 | B1 | 11/2002 | Wright et al. |
| 7,236,243 | B2 | 6/2007 | Beecroft et al. |
| 7,262,839 | B2 | 8/2007 | Treado et al. |
| 7,286,233 | B2 | 10/2007 | Pizzi |
| 7,414,724 | B2 | 8/2008 | Eckert et al. |
| 7,420,663 | B2 | 9/2008 | Wang et al. |
| 7,433,042 | B1 | 10/2008 | Cavanaugh et al. |
| 7,528,957 | B2 | 5/2009 | Lewis et al. |
| 7,535,617 | B2 | 5/2009 | Gupta et al. |
| 7,667,740 | B2 | 2/2010 | Hofer |
| 7,805,319 | B2 | 9/2010 | Badinelli |
| 7,897,923 | B2 | 3/2011 | Shelley et al. |
| 7,986,193 | B2 | 7/2011 | Krah |
| 8,060,383 | B2 | 11/2011 | Badinelli |
| 8,149,415 | B2 | 4/2012 | Sanders et al. |
| 8,269,174 | B2 | 9/2012 | Gardner, Jr. et al. |
| 8,274,739 | B2 | 9/2012 | Lee et al. |
| 8,284,401 | B2 | 10/2012 | Choi et al. |
| 8,330,945 | B2 | 12/2012 | Choi et al. |
| 8,462,420 | B2 | 6/2013 | Lee et al. |
| 8,542,359 | B2 | 9/2013 | Choi et al. |
| 8,665,440 | B1 | 3/2014 | Kompaniets et al. |
| 9,060,113 | B2 | 6/2015 | Rhoads et al. |
| 9,291,504 | B2 | 3/2016 | Goldring et al. |
| 9,383,258 | B2 | 7/2016 | Goldring et al. |
| 2002/0039186 | A1 | 4/2002 | Rosenberg et al. |
| 2002/0131047 | A1 | 9/2002 | Zarrabian et al. |
| 2002/0163641 | A1 | 11/2002 | Shroder |
| 2002/0191127 | A1 | 12/2002 | Roberts et al. |
| 2004/0019462 | A1* | 1/2004 | Gehrlein .............. B01F 3/02 702/188 |
| 2004/0136577 | A1 | 7/2004 | Rao et al. |
| 2005/0151975 | A1 | 7/2005 | Melnyk |
| 2005/0196046 | A1 | 9/2005 | Hudnut et al. |
| 2006/0086901 | A1 | 4/2006 | Price et al. |
| 2006/0124656 | A1 | 6/2006 | Popovich, Jr. et al. |
| 2006/0146315 | A1 | 7/2006 | Treado |
| 2007/0230932 | A1 | 10/2007 | Tanaka et al. |
| 2008/0061236 | A1 | 3/2008 | Meredith et al. |
| 2008/0073510 | A1 | 3/2008 | Finlay |
| 2008/0137328 | A1 | 6/2008 | Lee et al. |
| 2008/0204578 | A1 | 8/2008 | Scheuch et al. |
| 2008/0277625 | A1 | 11/2008 | Nakamura et al. |
| 2009/0201577 | A1 | 8/2009 | Laplante et al. |
| 2010/0085537 | A1 | 4/2010 | Ramella-Roman et al. |
| 2010/0110442 | A1 | 5/2010 | Adibi et al. |
| 2010/0128370 | A1 | 5/2010 | Chen et al. |
| 2010/0134794 | A1 | 6/2010 | Odegard et al. |
| 2010/0191493 | A1 | 7/2010 | Brown et al. |
| 2010/0201979 | A1 | 8/2010 | Momtahan et al. |
| 2010/0271352 | A1 | 10/2010 | Nakano et al. |
| 2010/0284005 | A1 | 11/2010 | Malinen et al. |
| 2010/0309454 | A1 | 12/2010 | Zhang |
| 2011/0255745 | A1 | 10/2011 | Hodder et al. |
| 2011/0261252 | A1 | 10/2011 | Chen |
| 2011/0318717 | A1 | 12/2011 | Adamowicz |
| 2012/0018829 | A1 | 1/2012 | Beck et al. |
| 2012/0019819 | A1 | 1/2012 | Messerchmidt |
| 2012/0053426 | A1 | 3/2012 | Webster et al. |
| 2012/0088486 | A1 | 4/2012 | Messerchmidt |
| 2013/0021611 | A1 | 1/2013 | Tsurutani |
| 2013/0155402 | A1 | 6/2013 | Walton et al. |
| 2014/0052555 | A1 | 2/2014 | Macintosh |
| 2014/0293091 | A1 | 10/2014 | Rhoads et al. |
| 2014/0320858 | A1 | 10/2014 | Goldring et al. |
| 2015/0036138 | A1 | 2/2015 | Watson et al. |
| 2015/0055132 | A1 | 2/2015 | Ricketts et al. |
| 2015/0204833 | A1 | 7/2015 | O'Brien et al. |
| 2015/0292948 | A1 | 10/2015 | Goldring et al. |
| 2015/0300879 | A1 | 10/2015 | Goldring et al. |
| 2015/0369725 | A1 | 12/2015 | Carvalho Sousa et al. |
| 2016/0033328 | A1 | 2/2016 | Walters |

FOREIGN PATENT DOCUMENTS

| | | |
|---|---|---|
| WO | WO-2010036906 A1 | 4/2010 |
| WO | WO-2013065035 A1 | 5/2013 |
| WO | WO-2015015493 A2 | 2/2015 |
| WO | WO-2015101992 A2 | 7/2015 |

OTHER PUBLICATIONS

Anoplate Website. Accessed Jun. 3, 2015. http://www.anoplate.com/capabilities/anoblack_ni.html.
Avian Technologies Website. Accessed Jun. 3, 2015. http://www.aviantechnologies.com/products/coatings/diffuse_black.php.
Co-pending U.S. Appl. No. 15/052,286, filed Feb. 24, 2016.
"Interference Filter Handbook," published by JDS Uniphase (Second Edition), Sep. 2006, p. 195-202 and 213-214.
International search report and written opinion dated Jan. 26, 2015 for PCT Application No. IL2014/050688.
International search report and written opinion dated Jul. 14, 2015 for PCT Application No. PCT/IL2015/050002.
Notice of allowance dated Jan. 22, 2016 for U.S. Appl. No. 14/702,342.
Notice of allowance dated Feb. 11, 2016 for U.S. Appl. No. 14/702,422.
Notice of allowance dated May 20, 2016 for U.S. Appl. No. 14/702,470.
Notice of allowance dated Jun. 2, 2016 for U.S. Appl. No. 14/702,461.
Notice of allowance dated Jul. 13, 2016 for U.S. Appl. No. 14/702,422.
Office action dated Jul. 5, 2016 for U.S. Appl. No. 15/052,286.
Office action dated Oct. 7, 2015 for U.S. Appl. No. 14/702,342.
Office action dated Oct. 21, 2015 for U.S. Appl. No. 14/702,422.
Office action dated Oct. 21, 2015 for U.S. Appl. No. 14/702,461.
Office action dated Oct. 30, 2015 for U.S. Appl. No. 14/702,470.

* cited by examiner

SPECTROMETRY SYSTEMS, METHODS, AND APPLICATIONS

CROSS-REFERENCE

The present application is a continuation of PCT Application Ser. No. PCT/IL2015/050002, filed on Jan. 1, 2015, entitled "Spectrometry Systems, Methods, and Applications"; which claims priority to U.S. Provisional Application Ser. No. 61/923,422, filed on Jan. 3, 2014, entitled "Spectroscopic Devices and Systems"; and U.S. Provisional Application Ser. No. 61/985,447 filed on Apr. 28, 2014, entitled "Spectroscopic Devices and Systems"; each of which is incorporated herein by reference in its entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference.

FIELD OF THE INVENTION

This invention relates to small, low-cost spectrometry systems. For example, it relates to hand-held systems that have sufficient sensitivity and resolution to perform spectroscopic analysis of substances (including complex mixtures, e.g. foodstuffs).

BACKGROUND OF THE INVENTION

Spectrometers are used for many purposes. For example spectrometers are used in the detection of defects in industrial processes, satellite imaging, and laboratory research. However these instruments have typically been too large and too costly for the consumer market.

Spectrometers detect radiation from a sample and process the resulting signal to obtain and present information about the sample that includes spectral, physical and chemical information about the sample. These instruments generally include some type of spectrally selective element to separate wavelengths of radiation received from the sample, and a first-stage optic, such as a lens, to focus or concentrate the radiation onto an imaging array.

The prior spectrometers can be less than ideal in at least some respects. Prior spectrometers having high resolution can be larger than ideal for use in many portable applications. Also, the cost of prior spectrometers can be greater than would be ideal. The prior spectrometers can be somewhat bulky, difficult to transport and the optics can require more alignment than would be ideal in at least some instances.

Although prior spectrometers with decreased size have been proposed, the prior spectrometers having decreased size and optical path length can have less than ideal resolution, sensitivity and less accuracy than would be ideal.

Data integration of prior spectrometers with measured objects can be less than ideal in at least some instances. For example, although prior spectrometers can provide a spectrum of a measured object, the spectrum may be of little significance to at least some users. It would be helpful if a spectrum of a measured object could be associated with attributes of the measured object that are useful to a user. For example, although prior spectrometers may be able to measure sugar, it would be helpful if a spectrometer could be used to determine the sweetness of an object such as an apple. Many other examples exist where spectral data alone does not adequately convey relevant attributes of an object, and it would be helpful to provide attributes of an object to a user in response to measured spectral data.

In light of the above, it an improved spectrometer and interpretation of spectral data that overcomes at least some of the above mentioned deficiencies of the prior spectrometers would be beneficial. Ideally such a spectrometer would be a compact, integrated with a consumer device such as a cellular telephone, sufficiently rugged and low in cost to be practical for end-user spectroscopic measurements of items, convenient to use. Further, it would be helpful to provide attribute data of many objects are related to the spectral data of the objects to many people.

SUMMARY

Embodiments of the present disclosure provide improved spectrometer methods and apparatus. In many embodiments, a spectrometer is used to determine one or more spectra of the object, and the one or more spectra are associated with one or more attributes of the object that are relevant to the user. While the spectrometer can take many forms, in many embodiments the spectrometer comprises a hand held spectrometer with wavelength multiplexing in which a plurality of wavelengths are used to illuminate the object and measure the one or more spectra. The spectral data of the object can be used to determine one or more attributes of the object. In many embodiments, the spectrometer is coupled to a database of spectral information that can be used to determine the attributes of the object. The spectrometer system may comprise a hand held communication device coupled to a spectrometer, in which the user can input and receive data related to the measured object with the hand held communication device. The embodiments disclosed herein allow many users to share object data with many people, in order to provide many people with actionable intelligence in response to spectral data.

In one aspect, an apparatus to measure spectra of an object comprises a spectrometer and a mobile communication device. The mobile communication device may comprise a processor and wireless communication circuitry to couple to the spectrometer and communicate with a remote server, the processor comprising instructions to transmit spectral data of an object to a remote server and receive object data in response to the spectral data from the remote server.

In many embodiments, the object data comprises one or more of an identification of the object, a classification of the object among a plurality of classifications, one or more components of the object, or food categories of the object.

In many embodiments, the processor comprises instructions to display a number of scans of a class of object, a number of countries associated with the number of scans, and a number of sub-classes of the class of object.

In many embodiments, the processor comprises instructions for a user to tag the spectral data with meta data, the meta data comprising one or more of an identification of the object, a classification of the object, a date of the spectral data, or a location of the object, and to transmit the spectral data with the meta data to a remote server.

In many embodiments, the spectrometer comprises a hand held spectrometer with a measurement beam capable of being directed at an object with user hand manipulations when the mobile communication device is operatively coupled to the hand held spectrometer with wireless communication.

In many embodiments, the mobile communication device comprises a user interface coupled to the processor for the user to input commands to the spectrometer. The user interface can comprise a touch screen display coupled to the spectrometer with the wireless communication circuitry, wherein the processor may comprise instructions to activate the screen of the user interface in response to a spectrometer user input. The spectrometer user input can comprise one or more buttons.

In many embodiments, the processor comprises instructions for the user to control the spectrometer in response to user input on the mobile communication device.

In many embodiments, the hand held spectrometer comprises an optical head, a control board, digital signal processing circuitry and wireless communication circuitry arranged to be supported with a hand of a user.

In many embodiments, the spectral data comprises compressed spectral data and the processor comprises instructions to transmit the compressed spectral data to the remote server.

In many embodiments, the spectral data comprises compressed spectral data, and the processor comprises instructions to relay the compressed spectral data to the remote server and receive the object data in response to the relayed compressed spectral data.

In many embodiments, the processor comprises instructions to transmit control instructions to the remote server and to receive control instructions from the remote server. The remote server can comprise a cloud based server. The remote server can comprise a database and a tangible medium embodying instructions of an algorithm to compare the spectral data to the database.

In many embodiments, the remote server comprises instructions to receive compressed, encrypted spectrometer data, generate a spectrum from the compressed, encrypted spectrometer data, generate a comparison the spectrum with a database of spectral information, and output one or more results of the comparison to the mobile communication device.

In many embodiments, the processor comprises instructions to provide a plurality of user navigable screens, the plurality of user navigable user interface screen configurations comprising one or more of a home screen, a user data screen, a user tools screen, a scan screen, a screen of a database of objects, or a result screen.

In many embodiments, the processor comprises instructions to receive an identification of the object from the remote server and to display the identification to the user.

In many embodiments, the processor comprises instructions to receive a plurality of possible identifications from the remote server and to display the plurality of possible identifications to the user, and to allow the user to select one of the plurality of possible identifications and to transmit the selected one to the remote server.

In many embodiments, the processor comprises instructions to receive user input in response to the user tasting the object and to transmit the user input to the remote server.

In many embodiments, the processor comprises instructions to display a graphical depiction of a plurality of classes of objects of a spectral database of the remote server to the user.

In many embodiments, the processor comprises instructions to receive a notification from the remote that a user has scanned a new class of objects and to display the notification.

In many embodiments, the processor comprises instructions to receive a notification from the remote that a user has scanned a new class of objects and to display the notification.

In many embodiments, the processor comprises instructions of a user application downloaded onto the mobile communication device and wherein the mobile communication device comprises a smart phone coupled to the spectrometer with a wireless communication protocol.

In many embodiments, the processor comprises instructions to display a message on the communication device that the communication device is waiting for a scan of the object from the spectrometer.

In many embodiments, the processor comprises instructions to display one or more spectrometer controls on the mobile communication device.

In many embodiments, the processor comprises instructions to display one or more user selectable applications for the user to operate spectrometer.

In another aspect, an apparatus to measure spectra of an object comprises a processor comprising a tangible medium embodying instructions of an application. The application can be configured to couple a mobile communication device to a spectrometer in order to receive spectral data and to transmit the spectral data to a remote server, and receive spectral data from the remote server.

In another aspect, an apparatus comprises a processor comprising instructions to receive spectral data from a remote spectrometer and compare a database of spectral data to the spectral data in order to identify an object in response to the spectral data.

In another aspect, a method of measuring spectra of an object comprises providing a spectrometer and providing a mobile communication device. The mobile communication device may comprise a processor and wireless communication circuitry, to couple the mobile communication device to the spectrometer and communicate with a remote server. The processor may comprise instructions to transmit spectral data of an object to a remote server and receive object data in response to the spectral data from the remote server.

In many embodiments, the spectrometer comprises a unique identification and the mobile communication device comprises instructions to receive the unique identification from the spectrometer with wireless communication and transmit the unique identification to the remote server with the spectral data.

In another aspect, an apparatus comprises a mobile communication device comprising a processor with instructions to receive spectral data from a spectrometer and a unique identification of the spectrometer.

In another aspect, an apparatus comprises a remote server comprising instructions to receive spectral data from a spectrometer and a unique identification of the spectrometer.

In many embodiments, the remote server comprises a centralized cloud based server configured to receive spectral data from millions of spectrometers and to transmit object data to the millions of spectrometers in response to the calibrated spectral data.

In many embodiments, the remote server comprises a plurality of unique identifications for a plurality of spectrometers, and calibration data for each of the plurality of spectrometers. The calibration data for each of the plurality of spectrometers may be associated with one of the plurality of unique identifications.

In many embodiments, the remote server comprises instructions to determine a calibrated spectrum in response to the spectral data, a unique identification of the spectrometer, and calibration data at the remote server associated with the unique identification, the remote server comprising instructions to transmit object data to the mobile communication device in response to the calibrated spectral data.

In many embodiments, the remote server is configured to receive one or more of the spectral data, an ambient temperature measured with the mobile device, a temperature of the object, a unique identification of the spectrometer, or compressed spectral data from the mobile communication device coupled to the spectrometer. The remote server can also be configured to determine a calibrated spectrum in response to the one or more of the ambient temperature measured with the mobile device, the temperature of the object, the unique identification of the spectrometer, or compressed spectral data from the mobile communication device coupled to the spectrometer. The remote server can also be configured to determine the object data in response to the calibrated spectrum, and output the object data to the mobile communication device.

In many embodiments, the remote server comprises instructions to receive spectrometer and mobile communication device data from a plurality of the mobile communication devices coupled to a plurality of spectrometers. The remove server can also comprise instructions to store the spectrometer and mobile communication device data from the plurality of mobile communication devices coupled to the plurality of spectrometers on a database of the remote server. The remove server can also comprise instructions to share the spectrometer and mobile communication device data of the database among the plurality of mobile communication devices.

In many embodiments, the mobile communication device data comprises one or more of a location of the spectral data when measured, a store associated with the location of the spectral data when measured, a time of the spectral data, a date of the spectral data, a temperature associated with the spectral data, and a user input indicating a type of the object as a member of a class of object types.

In many embodiments, the processor comprises instructions to display on the mobile communication device the type of object, a map showing spectral data of similar objects, or an indication of status of the similar objects based on the spectral data of the similar objects.

In many embodiments, the processor comprises instructions to download a map of attributes derived from spectral data of a plurality of spectrometers, the map having locations on the map, a location of a store, and the user interface configured for the user to click on the store and display object data in response to spectral data for objects of a type selected by the user.

The processor can be configured with instructions to display a time profile of object data in response to spectral data for the type of object at the store over time. The processor can be configured with instructions to display a plurality of time lines comprising a plurality of object data profiles in response to spectral data for a plurality of types of objects at the location with one or more pop up windows associated with the location. The plurality of object data profiles can comprise graphic profiles shown on the display corresponding to one or more of fruit or dairy products, and corresponding amounts of one or more of sweetness or fat.

In many embodiments, one or more of the processor or a processor of the remote server comprises instructions to determine a solid soluble content of an unpicked fruit.

In many embodiments, one or more of the processor or a processor of the remote server comprises instructions to determine a fertilization status of an unpicked plant, with non-destructive measurement of a near infrared spectrum of the unpicked plant or soil near the plant in response to a spectral signature of one or more of nitrogen, phosphate, or potash.

In many embodiments, one or more of the processor or a processor of the remote server comprises instructions to determine an on-line in-field spectrum analysis of different parts of plants, in order to provide early detection of stress of the plants and detection disease development.

In many embodiments, one or more of the processor or a processor of the remote server comprises instructions to monitor one or more of fertilization, watering or salinity of soil at many points in a field along with measurement location data in the field.

In many embodiments, one or more of the processor or a processor of the remote server comprises instructions to determine water content of leaves of a plant in response to a spectral signature of water, and display the water content to the user in order to provide the plant's watering status to the user.

In many embodiments, one or more of the processor or a processor of the remote server comprises instructions to determine water and fertilization status of soil and to display the water and fertilization status to the user.

In many embodiments, one or more of the processor or a processor of the remote server comprises instructions to identify a pill in response to a spectral signature of one or more of the medication of the pill or a coating of the pill.

In many embodiments, one or more of the processor or a processor of the remote server comprises instructions to determine active ingredient levels of Cannabis in response to one or more spectral features of an inflorescence of the Cannabis.

In many embodiments, one or more of the processor or a processor of the remote server comprises instructions to determine nutrients comprising one or more of fats, carbohydrates or water and a macro-nutrient estimation comprising an estimate of caloric value.

In many embodiments, one or more of the processor or a processor of the remote server comprises instructions to determine a cooking oil quality assessment in response to one or more of oxidation or acidity levels of the oil and display the cooking oil quality assessment to the user.

In many embodiments, one or more of the processor or a processor of the remote server comprises instructions to determine food quality in response to spectral data of one or more chemical traces related to bacteria or enzymes.

In many embodiments, one or more of the processor or a processor of the remote server comprises instructions to determine fruit ripeness in response to spectral data of one or more of enzymatic processes or water content.

In many embodiments, one or more of the processor or a processor of the remote server comprises instructions to identify gutter oil in response to spectral data related to fatty acid composition.

In many embodiments, one or more of the processor or a processor of the remote server comprises instructions to determine food safety in response to spectral data of one or more hazardous materials in a food product.

In many embodiments, one or more of the processor or a processor of the remote server comprises instructions to determine pet food quality in response to spectral data of meat and macro-nutrients of pet food.

In many embodiments one or more of the processor or a processor of the remote server comprises instructions to determine authenticity of a gem in response to spectral data of the gem.

In many embodiments, one or more of the processor or a processor of the remote server comprises instructions to determine a classification of a gem in response to spectral data and to sort the gem in response to the classification.

In many embodiments, one or more of the processor or a processor of the remote server comprises instructions to identify one or more explosives in response to spectral data of the object and link explosives identified at different places and times.

In many embodiments, one or more of the processor or a processor of the remote server comprises instructions to identify one or more drugs in response to spectral data of the object.

In many embodiments, one or more of the processor or a processor of the remote server comprises instructions to determine authentication of an alcoholic beverage in response to spectral data of the object.

In many embodiments, one or more of the processor or a processor of the remote server comprises instructions to identify the object as an authentic good in response to an infrared spectrum of the object as proof of originality of the object.

In many embodiments, one or more of the processor or a processor of the remote server comprises instructions to determine body fat in response to measured thickness of subcutaneous adipose tissue at a plurality of locations of a human or animal body, wherein the measured thickness is determined in response to spectra measured through skin at the plurality of locations.

In many embodiments, one or more of the processor or a processor of the remote server comprises instructions to determine dehydration of a human or animal subject in response spectral data measured through skin and related to skin morphology.

In many embodiments, one or more of the processor or a processor of the remote server comprises instructions to determine levels of hemoglobin of a subject in response to spectral data of blood measured through skin or in a sample container.

In many embodiments, one or more of the processor or a processor of the remote server comprises instructions to test blood and determine blood components in response to spectral data of a blood sample measured with blood placed in a container.

In many embodiments, one or more of the processor or a processor of the remote server comprises instructions to analyze urine and determine amounts of one or more of sodium, potassium or creatinine in response to the spectral data.

In many embodiments, one or more of the processor or a processor of the remote server comprises instructions to analyze skin to determine the presence of one or more of lesions, wounds, moles, spots, tissue hypoxia, deep tissue injury or melanoma.

In many embodiments, one or more of the processor or a processor of the remote server comprises instructions to analyze hair in response to the spectral data of the hair related to one or more of hair type, lotion, shampoo, conditioner or hair lotion cream.

In another aspect, an apparatus to measure an amount of sodium intake of a subject comprises: a sensor to measure one or more of sodium, potassium or creatinine provided with urine of the subject; and a processor comprising instructions to determine the amount of oral sodium intake in response to the one or more of sodium, potassium or creatinine provided with the urine.

In many embodiments, the sensor comprises one or more of a spectrometer or an electro-chemical sensor. In many embodiments, the sensor comprises an embedded sensor placed in one or more of a urinal or a toilet.

In many embodiments, one or more of the processor or a processor of the remote server comprises instructions to determine an amount of the creatinine provided with urine and the amount of oral sodium intake in response to the amount of creatinine. The processor or processor of the remote server may also comprise instructions to determine an amount of potassium provided with the urine and the amount of oral sodium intake in response to the amount of potassium.

In many embodiments, the amount of oral sodium intake comprises a normalized amount and one or more of the processor or the processor of the remote server comprises instructions to determine the normalized amount by dividing the amount of sodium by one or more of the amount of creatinine provided with the urine or the amount of potassium provided with the urine.

In another aspect, an optical spectrometer to measure spectra of a sample comprises a plurality of light sources, an optical diffuser, one or more photodetectors, and a circuitry. The plurality of light sources are arranged on a support, and the optical diffuser is located at a distance from the plurality of light sources. The one or more photodetectors receive a multiplexed optical signal from the sample illuminated with light from the plurality of light sources. The circuitry is coupled to the one or more photodetectors to receive the multiplexed optical signal.

In many embodiments, the spectrometer further comprises a second optical diffuser located at a second distance greater than the distance from the plurality of light sources. Each of the plurality of light sources may be mounted on the support, the plurality of light sources arranged in an array, and the first diffuser and the second diffuser may be arranged to provide a substantially uniform illumination pattern of the sample. The support may comprise a printed circuit board, and each of the plurality of light sources may comprise a light emitting diode.

In many embodiments, the spectrometer further comprises a housing to support the first diffuser and the second diffuser with fixed distances from the light sources, and the inner surface of the housing comprises a plurality of light absorbing structures to inhibit reflection of light from an inner surface of the housing. The plurality of light absorbing structures may comprise one or more of a plurality of baffles or a plurality of threads. The inner surface of the housing may define an inner diameter, wherein a separation distance between the first diffuser and the second diffuser may comprise no more than the diameter defined with the inner surface, and wherein the first diffuser may provide a substantially uniform illumination pattern on the second diffuser for light from each of the plurality of light sources.

In many embodiments, the first diffuser is separated from the second diffuser with a separation distance greater than the first distance, in order to illuminate the second diffuser with similar amounts of light from each of the plurality of light sources at each of a plurality of locations. The second distance may be at least about twice the first distance. The similar amounts of light at each of the plurality of locations may comprise a uniform illumination pattern comprising an energy profile with an energy profile variation of no more than about 10 percent of a mean value across the second diffuser.

In many embodiments, the optical signal comprises a time division multiplexed optical signal or a frequency division multiplexed optical signal. The multiplexed optical signal can comprise the frequency division multiplexed optical signal in order to inhibit motion related system noise. The multiplexed optical signal can comprise the frequency division multiplexed optical signal, and the circuitry can comprise a processor having a tangible medium embodying instructions to determine intensities of light from each of the plurality of light sources in response to frequency encoding of each of the plurality of light sources.

In many embodiments, the spectrometer further comprises drive circuitry configured to drive each of the light sources at an identifiable frequency corresponding to the light source, and the processor comprises instructions to determine an intensity of light from said each of the plurality of light sources based on an intensity of the identifiable frequency.

In many embodiments, the multiplexed optical signal comprises a time division multiplexed optical signal, and the circuitry is configured to illuminate the sample with each of the plurality of light sources in a sequence and determine the spectrum in response to the light energy measured with the one or more detectors for said each of the plurality of light sources of the sequence.

In many embodiments, the one or more photodetectors comprises a plurality of photodetectors to measure light of a plurality of wavelengths, and the plurality of photodetectors comprises a first photodetector to measure visible light and a second photodetector to measure infrared light.

In many embodiments, the spectrometer further comprises a lens located at a distance from the plurality of photodetectors, the plurality of photodetectors located in proximity in order to define a field of view of the plurality of photodetectors and wherein the field of view overlaps with an illumination patter of the plurality of light sources.

In many embodiments, the spectrometer further comprises a third diffuser separated from the plurality of light sources at a distance greater than the first distance and the second distance, in order to provide substantially uniform illumination with light from each of the plurality of light sources. The spectrometer may further comprise a plurality of light absorbing structures located on an inner surface of a housing, between the first diffuser and the second diffuser and between the second diffuser and the third diffuser, in order to inhibit reflections of the inner surface of the housing.

In many embodiments, the spectrometer further comprises one or more lenses located between the first diffuser and the second diffuser in order to direct light energy toward the second diffuser.

In many embodiments, the spectrometer further comprises a first optically transmissive cover plate located between the first plurality of light sources and the first diffuser, and a second optically transmissive cover plate located on a second side of the second diffuser away from a first side of the second diffuser. The first side may be oriented toward the plurality of light sources, and a housing may extend around the first optically transmissive cover plate and the second optically transmissive cover plate, in order to enclose the first diffuser and the second diffuser with a housing and the first optically transmissive cover plate and the second optically transmissive cover plate.

In many embodiments, the plurality of light sources of the spectrometer comprises at least about ten (10) light emitting diodes.

In another aspect, a spectroscopic device for collecting light spectra from a material to be analyzed comprises a diffuser, a first filter element, and a second filter element. The diffuser is configured to receive incident light from the material to be analyzed and to transmit diffuse light. The first filter element is configured to receive a portion of the diffuse light transmitted by the diffuser, and output a pattern of light angularly related to wavelengths associated with the diffuse light transmitted by the diffuser. The first filter element is responsive to wavelengths within a first wavelength range. The second filter element is configured to receive a portion of the diffuse light transmitted by the diffuser, and output a pattern of light angularly related to wavelengths associated with the diffuse light transmitted by the diffuser. The second filter element is responsive to wavelengths within a second wavelength range different from the first wavelength range, but the second wavelength range partially overlaps with the first wavelength range.

In many embodiments, the first wavelength range falls within a wavelength range of about 400 nm to about 1100 nm. In many embodiments, the second wavelength range falls within a wavelength range of about 400 nm to about 1100 nm. The second wavelength range may overlap the first wavelength range by at least 2% of the second wavelength range. The second wavelength range may overlap the first wavelength range by an amount of about 1% to 5% of the second wavelength range.

In many embodiments, the first and second filter elements are included within a plurality of filter elements arranged in an array.

In many embodiments, the device further includes at least one processing device configured to detect a sodium level in urine based on an output of the light sensitive detector. In many embodiments, the device further includes at least one processing device configured to detect a urea level in urine based on an output of the light sensitive detector. In many embodiments, the device further includes at least one processing device configured to detect an amount of carbohydrates present in food based on an output of the light sensitive detector. In many embodiments, the device further includes at least one processing device configured to confirm the material to be analyzed including an expected pharmaceutical composition based on an output of the light sensitive detector. In many embodiments, the device further includes at least one processing device configured to confirm the material to be analyzed including an expected alcoholic beverage composition based on an output of the light sensitive detector. In many embodiments, the device includes at least one processing device configured to detect an amount of methanol or gamma-hydroxybutyric acid present in a beverage based on an output of the light sensitive detector.

In many embodiments, the overlap between the first wavelength range and the second wavelength range is configured to provide algorithmic correction of gains across outputs of the first filter element and the second filter element.

In many embodiments, one or more of the first filter element, the second filter element, and a support array of the first and second filter elements may comprise one or more of a black coating configured to absorb light.

In another aspect, a spectroscopic device for collecting light spectra from a material to be analyzed comprises a diffuser, an array of filters, and a light sensitive detector. The diffuser is configured to receive incident light from the material to be analyzed and to transmit diffuse light. Each filter in the array of filters is configured to receive a portion of the diffuse light transmitted by the diffuser, and to output a pattern of light angularly related to wavelengths associated with the diffuse light transmitted by the diffuser. At least a first filter in the array is configured to induce cross talk in at least a second filter in the array, such that at least one feature in the pattern of light output by the second filter is associated with least one feature in the pattern of light output by the first filter, The light sensitive detector is configured to receive the pattern of light output by each filter.

In many embodiments, the light received by the first filter results in a pattern of non-concentric rings on the light sensitive detector.

In many embodiments, each filter includes an associated lens.

In many embodiments, each filter is associated with a range of wavelengths.

In many embodiments, a first range of wavelengths associated with a first filter partially overlaps with a second range of wavelengths associated with a second filter.

In many embodiments, the device is further configured such that when two different wavelengths, separated by at least five times a spectral resolution of the spectroscopic device, pass through the array of filters, light from at least two filters impinge on at least one common pixel of the light sensitive detector.

In many embodiments, the device further comprises at least one processing device configured to stitch together the light output by the array of filters to generate or reconstruct a spectrum associated with the incident light.

In many embodiments, the device further includes at least one processing device configured to detect a sodium level in urine based on an output of the light sensitive detector. In many embodiments, the device further includes at least one processing device configured to detect a urea level in urine based on an output of the light sensitive detector. In many embodiments, the device further includes at least one processing device configured to detect an amount of carbohydrates present in food based on an output of the light sensitive detector. In many embodiments, the device further includes at least one processing device configured to confirm the material to be analyzed including an expected pharmaceutical composition based on an output of the light sensitive detector. In many embodiments, the device further includes at least one processing device configured to confirm the material to be analyzed including an expected alcoholic beverage composition based on an output of the light sensitive detector. In many embodiments, the device further includes at least one processing device configured to detect an amount of methanol or gamma-hydroxybutyric acid present in a beverage based on an output of the light sensitive detector.

In another aspect, a spectroscopic device for collecting light spectra from a material to be analyzed comprises a first radiation emitter, a second radiation emitter, and a radiation diffusion unit. The first radiation emitter is configured to emit radiation within a first wavelength range, and the second radiation emitter configured to emit radiation within a second wavelength range, wherein the second wavelength range is different from the first wavelength range. The radiation diffusion unit is configured to receive as an input the radiation emitted from the first radiation emitter and the radiation emitted from the second radiation emitter and to provide as an output illumination radiation for use in analyzing the material. The radiation diffusion unit includes a first diffuser element, a second diffuser element, and at least one lens disposed between the first diffuser element and the second diffuser element.

In many embodiments, the first diffuser element is placed at an aperture plane of the lens, such that outputs of the first diffuser element at each of the directions from the first diffuser element are uniform.

In many embodiments, the first radiation emitter includes a light-emitting diode. In many embodiments, the second radiation emitter includes a light-emitting diode. In many embodiments, at least one of the first radiation emitter and the second radiation emitter includes a laser. In many embodiments, the device further includes third and fourth radiation emitters.

In many embodiments, the radiation emitted by the first radiation emitter and the second radiation emitter are time multiplexed.

In many embodiments, the radiation emitted by the first radiation emitter and the second radiation emitter are frequency modulated.

In many embodiments, the radiation emitted by the first radiation emitter and the second radiation emitter are amplitude modulated, each at a different frequency.

In many embodiments, the device further includes a light sensitive detector, sensitive to one or more spectral components in light gathered from the material as a result of interaction between the material and the illumination radiation provided by the radiation diffusion unit.

In many embodiments, the device further includes at least one processing device configured to detect a sodium level in urine based on an output of the light sensitive detector. In many embodiments, the device further includes at least one processing device configured to detect a urea level in urine based on an output of the light sensitive detector. In many embodiments, the device further includes at least one processing device configured to detect an amount of carbohydrates present in food based on an output of the light sensitive detector. In many embodiments, the device further includes at least one processing device configured to confirm the material to be analyzed including an expected pharmaceutical composition based on an output of the light sensitive detector. In many embodiments, the device further includes at least one processing device configured to confirm the material to be analyzed including an expected alcoholic beverage composition based on an output of the light sensitive detector. In many embodiments, the device further includes at least one processing device configured to detect an amount of methanol or gamma-hydroxybutyric acid present in a beverage based on an output of the light sensitive detector.

In another aspect, a portable device for analyzing at least one material from an environment comprises a spectrometer and at least one processing device. The spectrometer is configured to collect light spectra from the at least one material and provide an output including signals representative of patterns of light provided to a light sensitive detector associated with the spectrometer, wherein the patterns of light are spatially related to wavelengths associated with the light spectra collected from the at least one material. The at least one processing device is configured to receive the output of the spectrometer, receive an output from at least one additional sensor, and provide to a display unit information relating to at least one characteristic of the material to be analyzed. The one additional sensor is configured to generate a signal associated with at least one aspect of the environment including the at least one material. The information provided to the display unit is developed based on analysis of both the output of the spectrometer and the output of the at least one additional sensor.

In many embodiments, the at least one additional sensor is located on the portable device together with the spectrometer.

In many embodiments, the display unit is located on the portable device together with the spectrometer.

In many embodiments, both the output of the spectrometer and the output of the at least one additional sensor are analyzed by the at least one processing device.

In many embodiments, the at least one additional sensor includes one or more of a camera, temperature sensor, capacitance sensor, resistance sensor, conductivity sensor, inductance sensor, altimeter, global positioning system unit, turbidity sensor, pH sensor, accelerometer, vibration sensor, biometric sensor, chemical sensor, color sensor, clock, ambient light sensor, microphone, penetrometer, durometer, barcode reader, flowmeter, speedometer, magnetometer, and another spectrometer.

In another aspect, a portable analysis system for analyzing at least one material from an environment comprises a spectrometer and at least one processing device. The spectrometer is configured to collect light spectra from the at least one material and provide an output including signals representative of patterns of light provided to a light sensitive detector associated with the spectrometer, wherein the patterns of light are spatially related to wavelengths associated with the light spectra collected from the at least one material; and at least one processing device. The at least one processing device is configured to generate a user interface for a display. The user interface includes a first user-selectable interface element associated with a first type of analysis to be performed relative to the light spectra collected from the at least one material. The user interface also includes at least a second user-selectable interface element associated with a second type of analysis to be performed relative to the light spectra collected from the at least one material, wherein the second type of analysis is different from the first type of analysis in at least one aspect. The at least one processing device is further configured to determine whether selection of the first user-selectable interface element or selection of the second user-selectable interface element has occurred, cause performance of the type of analysis associated with the selected user-interface element, and provide to the display information relating to the analysis performed.

In many embodiments, the system further includes a display.

In many embodiments, the spectrometer is associated with a first mobile device, and the display is associated with a second mobile device different from the first mobile device. The second mobile device may include a mobile phone.

In many embodiments, one or more of the first type of analysis and the second type of analysis relates to one or more of a fat content in food, sugar content in food, protein content in food, gluten content in food, water level in a material, characteristics of wine, characteristics of cheese, fiber content in food, spoilage agents in food, food composition, pharmaceutical composition, material authenticity, presence of poisonous materials, gas composition, water quality, and urine composition.

In many embodiments, at least one of the first user-selectable interface element and the second user-selectable interface element includes an icon associated with a spectroscopic analysis application.

In many embodiments, at least one of the first user-selectable interface element and the second user-selectable interface element includes an analysis identifier included among a plurality of available analysis functions. The analysis identifier may include an image. The analysis identifier may include text.

In many embodiments, analysis data can be shared between applications associated with the first user-selectable interface element and the second user-selectable interface element.

In many embodiments, the system further includes at least a third user-selectable interface element associated with a third type of analysis to be performed relative to the light spectra collected from the at least one material, wherein the third type of analysis includes at least one aspect different from the first type of analysis and the second type of analysis.

In another aspect, a portable analysis system for analyzing at least one material from an environment comprises a spectrometer and at least one processing device. The spectrometer is configured to collect light spectra from the at least one material and provide an output including signals representative of patterns of light provided to a light sensitive detector associated with the spectrometer, wherein the patterns of light are spatially related to wavelengths associated with the light spectra collected from the at least one material; and at least one processing device. The at least one processing device is configured to receive the output from the spectrometer. The processing device is further configured to select, based on the output, between a first type of analysis to be performed relative to the light spectra collected from the at least one material and a second type of analysis to be performed relative to the light spectra collected from the at least one material. The second type of analysis may be different from the first type of analysis in at least one respect. The processing device is further configured to cause performance of the selected type of analysis, and provide to a display information relating to the automatically selected type of analysis to be performed.

In many embodiments, selection between the first and second type of analysis is automatically performed based on at least one characteristic of the output provided by the spectrometer. The at least one characteristic may be indicative of a material that includes wine. The at least one characteristic may be indicative of a material that includes cheese. The at least one characteristic may be indicative of a material that includes multiple food types.

In many embodiments, the selection between the first and second type of analysis may be based on user input.

In many embodiments, one or more of the first type of analysis and the second type of analysis relates to one or more of a fat content in food, sugar content in food, protein content in food, gluten content in food, water level in a material, characteristics of wine, characteristics of cheese, fiber content in food, spoilage agents in food, food composition, pharmaceutical composition, material authenticity, presence of poisonous materials, gas composition, water quality, and urine composition.

In many embodiments, the system further includes an image capture device configured to acquire image data representative of the environment. The image capture device can include a camera, wherein the at least one processing device is further configured to: receive the image data acquired by the image capture device; and use at least a portion of the image data in the selection of the first type of analysis or the second type of analysis.

In many embodiments, the at least one processing device is configured to recognize a characteristic of the at least one material from the environment based on the image data and select between the first type of analysis and the second type of analysis based on the recognized characteristic. The recognized characteristic may be that the at least one material includes one or more of a wine, cheese, or other food type.

In many embodiments, the selection of the first and second types of analysis may be further based on a predetermined hierarchy.

In many embodiments, the system further comprises a display.

In many embodiments, the spectrometer is associated with a first mobile device, and the display is associated with a second mobile device different from the first mobile device. The second mobile device can include a mobile phone.

In another aspect, a spectroscopic device for analyzing characteristics of fuel comprises a diffuser configured to receive incident light from the material to be analyzed and to transmit diffuse light, and an array of filters. Each filter is configured to receive a portion of the diffuse light transmitted by the diffuser and output a pattern of light angularly related to wavelengths associated with the diffuse light transmitted by the diffuser. The device further comprises a light sensitive detector is configured to receive the patterns of light output from the array of filters and provide an output signal representative of the received patterns of light. The device further comprises at least one processing device. The at least one processing device is configured to receive the output signal of the light sensitive detector and determine, based on analysis of the output signal, at least one characteristic associated with the fuel. The processing device is further configured to provide to a display information relating to the at least one characteristic.

In many embodiments, the device may further include an array of lenses disposed between the array of filters and the light sensitive detector, wherein each lens in the array of lenses is associated with a corresponding filter in the array of filters.

In many embodiments, the at least one characteristic includes a determined type associated with the fuel. In many embodiments, the at least one characteristic includes a determined contaminant level associated with the fuel. In many embodiments, the at least one characteristic includes a determined octane level associated with the fuel. In many embodiments, the at least one characteristic includes a determined cetane level associated with the fuel. In many embodiments, the at least one characteristic includes a substance composition associated with the fuel.

In many embodiments, the device further comprises a display.

In many embodiments, the device is configured for integration with a vehicle component. The vehicle component may include a fuel system component of the vehicle. The vehicle component may include at least one of a fuel tank, fuel line, or a fuel injector of the vehicle.

In another aspect, a spectroscopic device for analyzing characteristics of an agricultural product comprises a diffuser configured to receive incident light from the material to be analyzed and to transmit diffuse light, and an array of filters. Each filter is configured to receive a portion of the diffuse light transmitted by the diffuser and output a pattern of light angularly related to wavelengths associated with the diffuse light transmitted by the diffuser. The device further comprises a light sensitive detector configured to receive the patterns of light output from the array of filters and provide an output signal representative of the received patterns of light. The device further comprises at least one processing device. The processing device is configured to receive the output signal of the light sensitive detector, determine, based on analysis of the output signal, at least one characteristic associated with the fuel, and provide to a display information relating to the at least one characteristic.

In many embodiments, the device further includes an array of lenses disposed between the array of filters and the light sensitive detector, wherein each lens in the array of lenses is associated with a corresponding filter in the array of filters.

In many embodiments, the at least one characteristic includes a determined type associated with the agricultural product. In many embodiments, the at least one characteristic includes a determined ripeness level of the agricultural product. In many embodiments, the at least one characteristic includes a determined moisture level of the agricultural product.

In many embodiments, the agricultural product includes at least one of grain, rice, coffee, spice, oil-seed, or forage. In many embodiments, the agricultural product includes milk, and the at least one characteristic includes a determined fat content of the milk.

In many embodiments, the device further includes at least one sensor configured to provide an output from which another characteristic of the agricultural product can be determined.

In many embodiments, the at least one processing device is configured to provide to the display information determined based on the at least one characteristic and the another characteristic. The another characteristic may include a firmness level.

In many embodiments, the device may further comprise a display.

In many embodiments, the device is configured to detect methanol in an alcoholic beverage. In many embodiments, the device is configured to detect melamine in dairy products.

In another aspect, a spectroscopic device for analyzing characteristics of a power converting component comprises a diffuser configured to receive incident light from the material to be analyzed and to transmit diffuse light and an array of filters. Each filter is configured to receive a portion of the diffuse light transmitted by the diffuser and output a pattern of light angularly related to wavelengths associated with the diffuse light transmitted by the diffuser. The device further comprises a light sensitive detector, configured to receive the patterns of light output from the array of filters and provide an output signal representative of the received patterns of light. The device further comprises a data interface and at least one processing device. The at least one processing device may be configured to receive the output signal of the light sensitive detector, determine, based on analysis of the output signal, at least one characteristic associated with the fuel, and provide to a display information relating to the at least one characteristic.

In many embodiments, the device may further comprise an array of lenses disposed between the array of filters and the light sensitive detector, wherein each lens in the array of lenses is associated with a corresponding filter in the array of filters.

In many embodiments, the at least one characteristic includes a determined condition associated with a fluid, the fluid associated with the power converting component.

In many embodiments, the device further comprises a display.

In another aspect, a server-based spectroscopic analysis engine system comprises a data interface, a database, and at least one processing device. The at least one processing device is configured to receive a spectroscopic analysis request from each of a plurality of analysis requesters. Each spectroscopic analysis request is received via the data interface and includes data representing at least one acquired light spectrum and one or more pieces of accompanying data associated with the light spectrum. The processing device is further configured to analyze, for each analysis request, the acquired light spectrum and the one or more pieces of accompanying data associated with the light spectrum using spectroscopic information stored in the database and compile a list of analysis results, for each respective analysis request, based on algorithms associated with the database. The processing device is further configured to update the database, for each analysis request, with the at least one acquired light spectrum and the one or more pieces of accompanying data associated with the light spectrum. The processing device is further configured to provide, for each analysis request, the list of analysis results compiled for the respective analysis request.

In many embodiments, the update to the database is performed only if the one or more pieces of accompanying data are determined to represent valid data associated with the light spectrum.

In many embodiments, the one or more pieces of information include one or more conditions associated with collection of the acquired light spectrum, including at least one of a temperature, a geographic location, a category of a material, a type of a material, a chemical composition, a time, an appearance of a material, a color of a material, a taste of a material, a smell of a material, and an observable characteristic associated with a material.

In many embodiments, the data interface is configured to transmit and receive communications from the Internet.

In many embodiments, the acquired light spectrum includes at least one of an absorption spectrum, a fluorescence spectrum, and a Raman spectrum.

In many embodiments, the analysis results include one or more of an identification of a material, a freshness of a material, an image of a material, and a textual description of a material.

In many embodiments, the system is configured to provide a user interface on a user device, the user interface including analysis request data inputs. The data interface may be configured to receive the analysis request as data provided by the user to the analysis request data inputs.

In another aspect, a server-based spectroscopic system comprises a data interface, a database configured to store spectroscopic data and associated preference data for each of a plurality of users, and at least one processing device. The at least one processing device is configured to receive a recommendation request from a device associated with a user from among the plurality of users. The recommendation request is received via the data interface and includes data representing at least one acquired light spectrum. The processing device is further configured to analyze the acquired light spectrum using spectroscopic information stored in the database for the user, and generate at least one recommendation based on the analysis, and to provide the recommendation to the user device via the data interface.

In many embodiments, the at least one processing device is further configured to receive a preference update from a device of the user, wherein the preference update is received via the data interface and includes data representing at least one acquired light spectrum and at least one indicator of user preference, and updates the database with the at least one acquired light spectrum and the at least one indicator of user preference.

In many embodiments, the acquired light spectrum includes at least one of an absorption spectrum, a fluorescence spectrum, and a Raman spectrum.

In another aspect, a server-based spectroscopic system comprises a sensor configured to collect data from a material, a communication device configured to transmit the collected data to a cloud-based server, a cloud-based server configured to analyze the data transmitted from the communication device, and a device configured to receive analysis results from the cloud-based server and present the analysis results to a user.

In many embodiments, the sensor comprises an optical spectroscopy system, wherein the optical spectroscopy system comprises an optical spectrometer, an illumination light source, and a processing device. The system is configured to produce a spectrum that corresponds to one or more chemical or physical properties of the material.

In many embodiments, the optical spectrometer has dimensions smaller than 2 cm×2 cm×2 cm.

In many embodiments, the communication device is a mobile phone.

In many embodiments, the communication device receives the collected data from the sensor using wireless communication.

In many embodiments, the cloud-based server comprises a database of spectra. The database of spectra may be updatable. The cloud-based server may comprise one or more algorithms for data analysis. The cloud-based server may support more than one sensor or more than one user. The more than one sensors may be configured and calibrated to support the same database.

In many embodiments, the sensor has a warm-up time of less than 5 seconds. In many embodiments, the sensor has a warm-up time of less than 1 second.

In many embodiments, the illumination light source comprises one or more light-emitting diodes. In many embodiments, the illumination light source is broad-band. In many embodiments, the illumination light source comprises one or more lasers.

In many embodiments, the system comprises one or more applications allowing users to perform a specific operation.

In many embodiments, the system is configured to provide to the users a method for developing applications. In many embodiments, the method for developing applications comprises a method for creating a new database.

In many embodiments, a spectroscopic device may further comprise one or more lens elements having a shape such that an output of each lens element is configured to have a point-spread-function size that is larger than optimal, thereby increasing a depth-of-field of the one or more lens elements.

In many embodiments, a spectroscopic device may further comprise one or more lens elements having an aspheric shape profile configured to distort an output of each lens element, such that the output width of a ring of a wavelength of said each lens element comprises reduced non-linearity with respect to an angle of an incident light beam.

DETAILED DESCRIPTION

Figure 1:
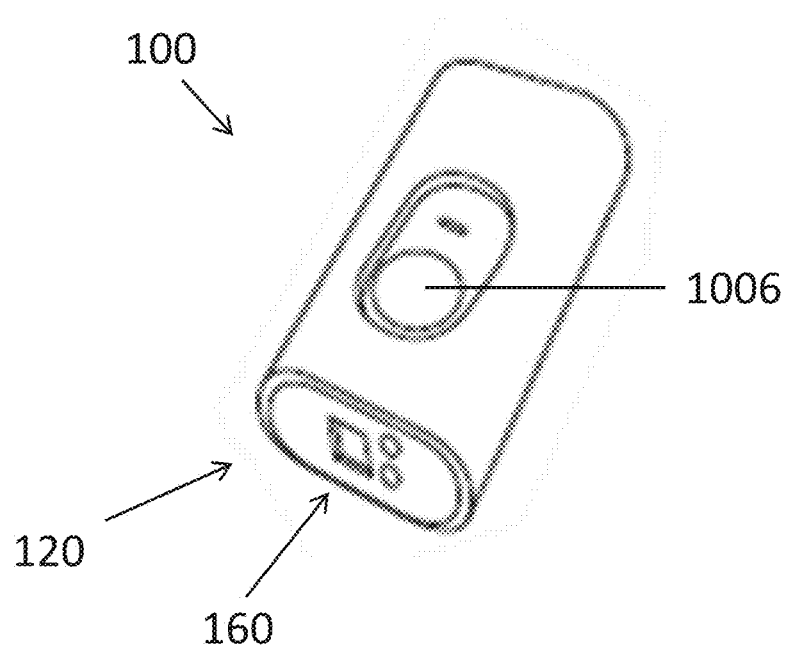
FIG. 1 shows an isometric view of a compact spectrometer, in accordance with embodiments.

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figure and described in the specification, but only as indicated in the accompanying claims, with the proper scope determined only by the broadest interpretation of said claims.

A better understanding of the features and advantages of the present disclosure will be obtained by reference to the following detailed description that sets forth illustrative embodiments, in which the principles of embodiments of the present disclosure are utilized, and the accompanying drawings.

The embodiments disclosed herein can be combined in one or more of many ways to provide improved spectrometer methods and apparatus. One or more components of the embodiments disclosed herein can be combined with each other in many ways. In many embodiments, a spectrometer as described herein can be used to generate spectral data of the object, and the spectral data of the object transmitted to a cloud based server in order to determine one or more attributes of the object. Alternatively or in combination, data of the cloud based server can be made available to both users and non-users of the spectrometers in order to provide useful information related to attributes of measured objects. The data of the cloud based server can be made available to users and non-users in many ways, for example with downloadable apps capable of connecting to the cloud based server and downloading information related to spectra of many objects.

The embodiments disclosed herein are also capable of providing a database of attributes of many objects related to spectral data. A mobile communication device can be configured for a user to input attributes of one or more measured objects in order to construct a database based on spectral data of many measured objects.

As used herein like characters refer to like elements.

As used herein "light" encompasses electromagnetic radiation having wavelengths in one or more of the ultraviolet, visible, or infrared portions of the electromagnetic spectrum.

As used herein, the term "dispersive" is used, with respect to optical components, to describe a component that is designed to separate spatially, the different wavelength components of a polychromatic beam of light. Non-limiting examples of "dispersive" optical elements by this definition include diffraction gratings and prisms. The term specifically excludes elements such as lenses that disperse light because of non-idealities such as chromatic aberration or elements such as interference filters that have different transmission profiles according to the angle of incident radiation. The term also excludes the filters and filter matrixes described herein.

As used herein the term "store" encompasses a structure that stores objects, such as a crate or building.

Overview of Compact Spectrometer System

FIG. 1 shows an isometric view of a compact spectrometer, in accordance with embodiments. The spectrometer 102 can be used a general purpose material analyzer for many applications, as described in further detail herein. In particular, the spectrometer 102 can be used to identify materials or objects, provide information regarding certain properties of the identified materials, and accordingly provide users with actionable insights regarding the identified materials. The spectrometer 102 comprises a spectrometer head 120 configured to be directed towards a sample material. The spectrometer head 120 comprises a spectrometer module 160, configured to obtain spectral information associated with the sample material. The spectrometer may comprise simple means for users to control the operation of the spectrometer, such as operating button 1006. The compact size of the spectrometer 102, in some embodiments smaller than 2 cm×2 cm×2 cm, can provide a hand held device that can be directed (e.g., pointed) at a material to rapidly obtain information about the material.

Figure 2:
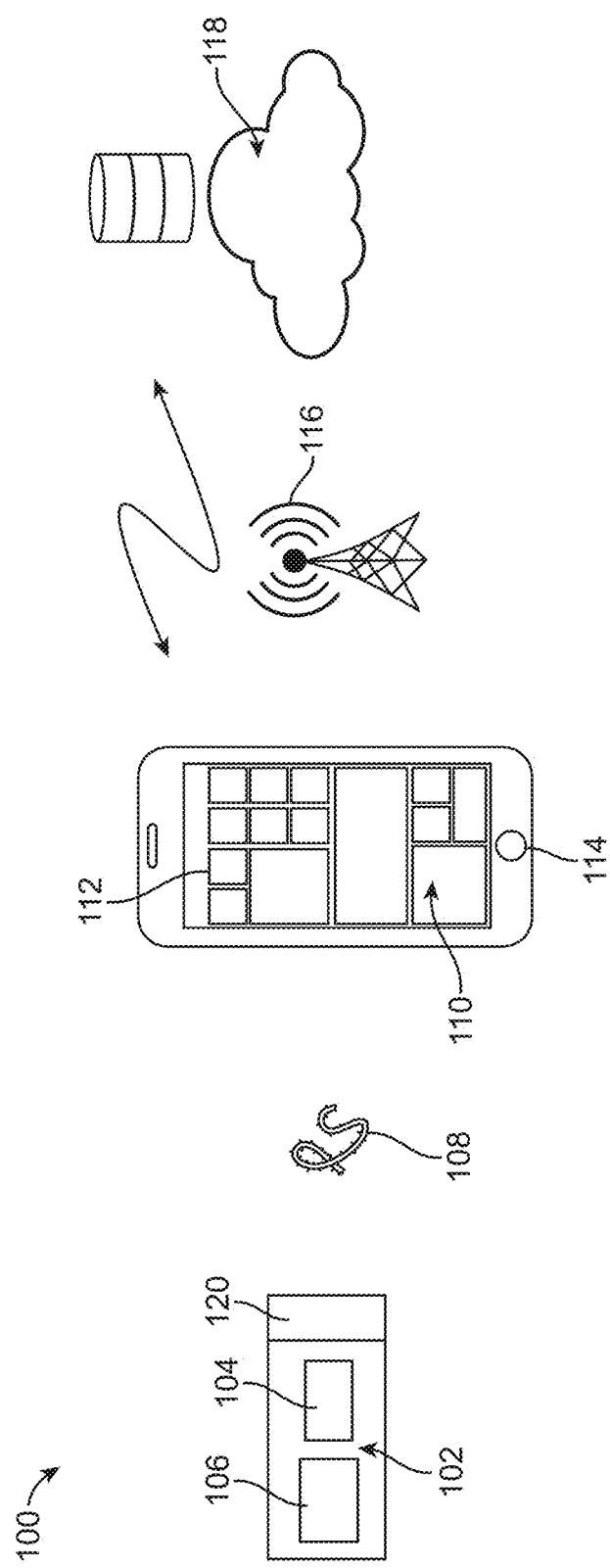
FIG. 2 shows a schematic diagram of a spectrometer system, in accordance with embodiments.

FIG. 2 shows a schematic diagram of a spectrometer system, in accordance with embodiments. In many embodiments, the spectrometer system 100 comprises a spectrometer 102 as described herein and a hand held device 110 in wireless communication 116 with a cloud based server or storage system 118. The spectrometer 102 can acquire the data as described herein. The hand held spectrometer 102 may comprise a processor 106 and communication circuitry 104 coupled to the spectrometer head 120 having spectrometer components as described herein. The spectrometer can transmit the data to the hand held device 110 with communication circuitry 104 with a communication link, such as a wireless serial communication link, for example Bluetooth™. The hand held device can receive the data from the spectrometer 102 and transmit the data to the cloud based storage system 118. The data can be processed and analyzed by the cloud based server 118, and transmitted back to the hand held device 110 to be displayed to the user.

The spectrometer system may allow multiple users to connect to the cloud based server 118 via their hand held devices 110, as described in further detail herein. In some embodiments, the server 118 may be configured to simultaneously communicate with up to millions of hand held devices 110. The ability of the system to support a large number of users and devices at the same time can allow users of the system to access, in some embodiments in real-time, large amounts of information relating to a material of interest. Access to such information may provide users with a way of making informed decisions relating to a material of interest.

The hand held device 110 may comprise one or more components of a smart phone, such as a display 112, an interface 114, a processor, a computer readable memory and communication circuitry. The device 110 may comprise a substantially stationary device when used, such as a wireless communication gateway, for example.

The processor 106 may comprise a tangible medium embodying instructions, such as a computer readable memory embodying instructions of a computer program. Alternatively or in combination the processor may comprise logic such as gate array logic in order to perform one or more logic steps.

Because of its small size and low complexity, the compact spectrometer system herein disclosed can be integrated into a mobile communication device such as a cellular telephone. It can either be enclosed within the device itself, or mounted on the device and connected to it by wired or wireless means for providing power and a data link. By incorporating the spectrometer system into a mobile device, the spectra obtained can be uploaded to a remote location, analysis can be performed there, and the user notified of the results of the analysis. The spectrometer system can also be equipped with a GPS device and/or altimeter so that the location of the sample being measured can be reported. Further non-limiting examples of such components include a camera for recording the visual impression of the sample and sensors for measuring such environmental variables as temperature and humidity.

Figure 3:
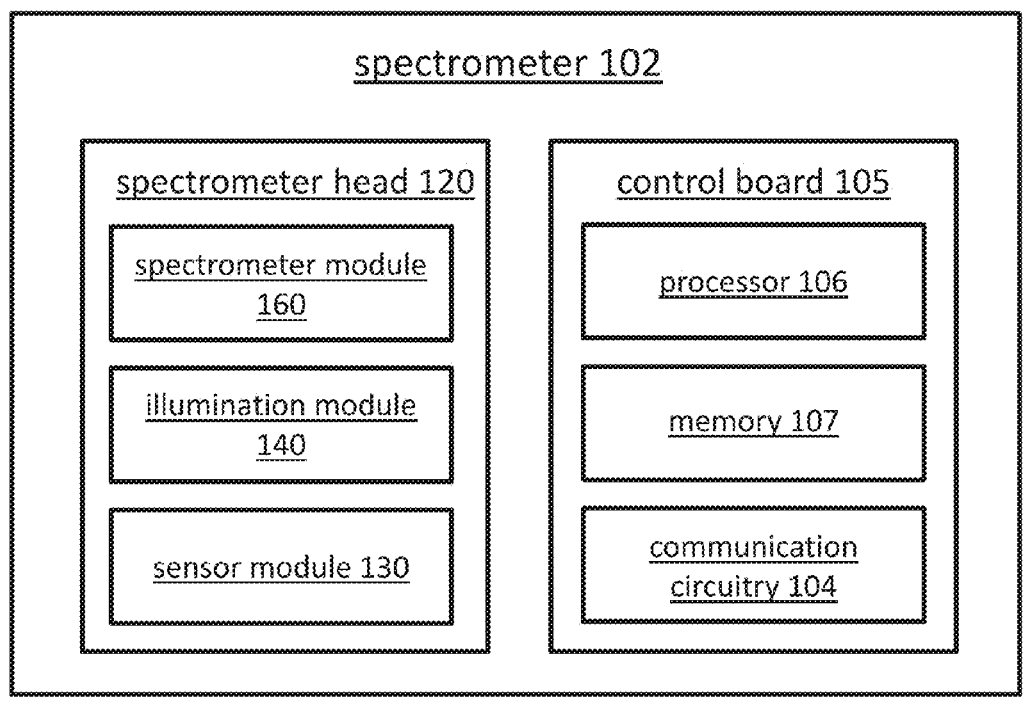
FIG. 3 shows a schematic diagram of the compact spectrometer of FIG. 1, in accordance with embodiments.

FIG. 3 shows a schematic diagram of the compact spectrometer of FIG. 1, in accordance with embodiments. The spectrometer 102 may comprise a spectrometer head 120 and a control board 105. The spectrometer head 102 may comprise one or more of a spectrometer module 160 and an illumination module 140, which together can be configured to measure spectroscopic information relating to a sample material. The spectrometer head 102 may further comprise one or more of a sensor module 130, which can be configured to measure non-spectroscopic information relating to a sample material. The control board 105 may comprise one or more of a processor 106, communication circuitry 104, and memory 107. Components of the control board 105 can be configured to transmit, store, and/or analyze data, as described in further detail herein.

The sensor module 130 can enable the identification of the sample material based on non-spectroscopic information in addition to the spectroscopic information measured by the spectrometer module 160. Such a dual information system may enhance the accuracy of detection or identification of the material.

The sensor element of sensor module 130 may comprise any sensor configured to generate a non-spectroscopic signal associated with at least one aspect of the environment, including the material being analyzed. For example, the sensor element may comprise one or more of a camera, temperature sensor, electrical sensor (capacitance, resistance, conductivity, inductance), altimeter, GPS unit, turbidity sensor, pH sensor, accelerometer, vibration sensor, biometric sensor, chemical sensor, color sensor, clock, ambient light sensor, microphone, penetrometer, durometer, barcode reader, flowmeter, speedometer, magnetometer, and another spectrometer.

The output of the sensor module 130 may be associated with the output of the spectrometer module 160 via at least one processing device of the spectrometer system. The processing device may be configured to receive the outputs of the spectrometer module and sensor module, analyze both outputs, and based on the analysis provide information relating to at least one characteristic of the material to a display unit. A display unit may be provided on the device in order to allow display of such information.

In many embodiments, the spectrometer module comprises one or more lens elements. Each lens can be made of two surfaces, and each surface may be an aspheric surface. In designing the lens for a fixed-focus system, it may be desirable to reduce the system's sensitivity to the exact location of the optical detector on the z-axis (the axis perpendicular to the plane of the optical detector), in order to tolerate larger variations and errors in mechanical manufacturing. To do so, the point-spread-function (PSF) size and shape at the nominal position may be traded off with the depth-of-field (DoF) length. For example, a larger-than-optimal PSF size may be chosen in return for an increase in the DoF length. One or more of the aspheric lens surfaces of each lens of a plurality of lenses can be shaped to provide the increased PSF size and the increased DoF length for each lens. Such a design may help reduce the cost of production by enabling the use of mass production tools, since mass production tools may not be able to meet stringent tolerance requirements associated with systems that are comparatively more sensitive to exact location of the optical detector.

In some embodiments, the measurement of the sample is performed using scattered ambient light.

In many embodiments, the spectrometer system comprises a light or illumination source. The light source can be of any type (e.g. laser or light-emitting diode) known in the art appropriate for the spectral measurements to be made. In some embodiments the light source emits from 350 nm to 1100 nm. The wavelength(s) and intensity of the light source will depend on the particular use to which the spectrometer will be put. In some embodiments the light source emits from 0.1 mW to 500 mW.

In many embodiments, the spectrometer also includes a power source (e.g. a battery or power supply). In some embodiments the spectrometer is powered by a power supply from a consumer hand held device (e.g. a cell phone). In some embodiments the spectrometer has an independent power supply. In some embodiments a power supply from the spectrometer can supply power to a consumer hand held device.

The spectrometers as described herein can be adapted, with proper choice of light source, detector, and associated optics, for a use with a wide variety of spectroscopic techniques. Non-limiting examples include Raman, fluorescence, and IR or UV-VIS reflectance and absorbance spectroscopies. Because, as described above, compact spectrometer system can separate a Raman signal from a fluorescence signal, in some embodiments of the invention, the same spectrometer is used for both spectroscopies.

In some embodiments, the spectrometer does not comprise a monochromator.

Spectrometer Using Secondary Emission Illumination with Filter-Based Optics

Figure 4:
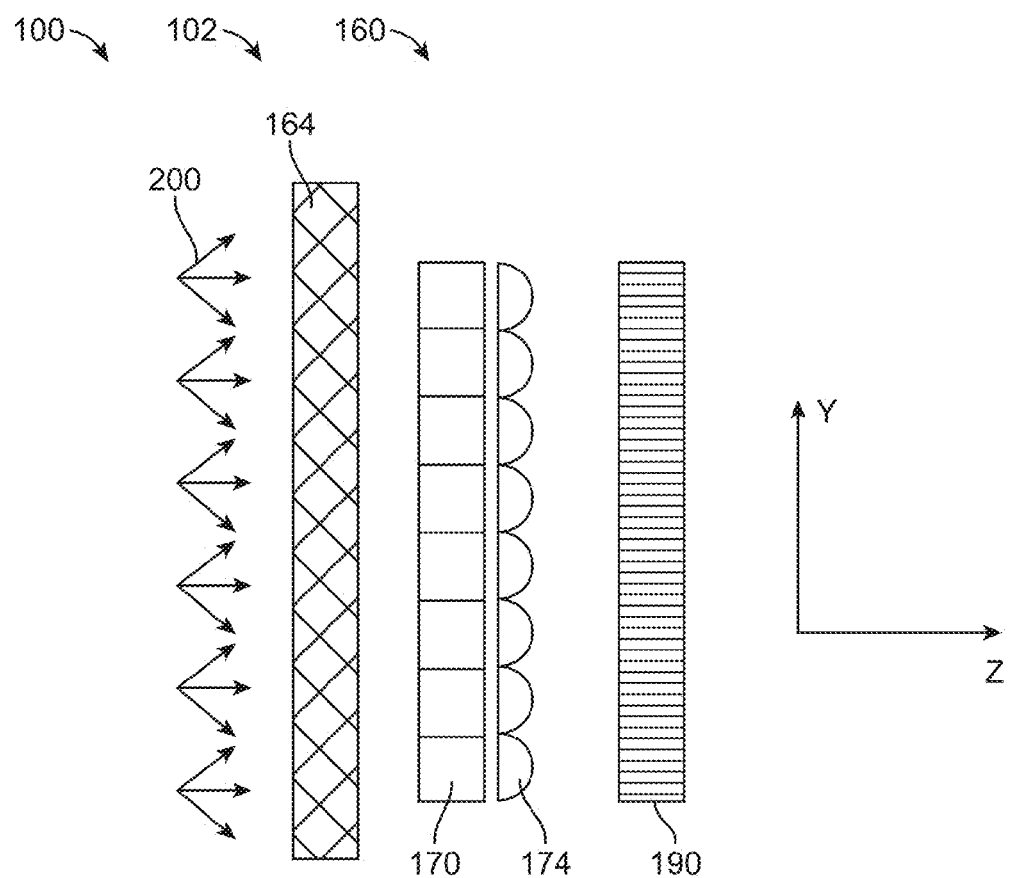
FIG. 4 shows a schematic diagram of an optical layout in accordance with embodiments.

Reference is now made to FIG. 4, which illustrates non-limiting embodiments of the compact spectrometer system 100 herein disclosed. The system comprises a spectrometer 102, which comprises various modules such as a spectrometer module 160. As illustrated, the spectrometer module 160 may comprise a diffuser 164, a filter matrix 170, a lens array 174 and a detector 190.

In many embodiments, the spectrometer system comprises a plurality of optical filters of filter matrix 170. The optical filter can be of any type known in the art. Non-limiting examples of suitable optical filters include Fabry-Perot (FP) resonators, cascaded FP resonators, and interference filters. For example, a narrow bandpass filter (≤10 nm) with a wide blocking range outside of the transmission band (at least 200 nm) can be used. The center wavelength (CWL) of the filter can vary with the incident angle of the light impinging upon it.

In many embodiments, the central wavelength of the central band can vary by 10 nm or more, such that the effective range of wavelengths passed with the filter is greater than the bandwidth of the filter. In many embodiments, the central wavelength varies by an amount greater than the bandwidth of the filter. For example, the bandpass filter can have a bandwidth of no more than 10 nm and the wavelength of the central band can vary by more than 10 nm across the field of view of the sensor.

In many embodiments, the spectrometer system comprises a filter matrix. The filter matrix can comprise one or more filters, for example a plurality of filters. The use of a single filter can limit the spectral range available to the spectrometer. A filter can be an element that only permits transmission of a light signal with a predetermined incident angle, polarization, wavelength, and/or other property. For example, if the angle of incidence of light is larger than 30°, the system may not produce a signal of sufficient intensity due to lens aberrations and the decrease in the efficiency of the detector at large angles. For an angular range of 30° and an optical filter center wavelength (CWL) of ~850 nm, the spectral range available to the spectrometer can be about 35 nm, for example. As this range can be insufficient for some spectroscopy based applications, embodiments with larger spectral ranges may comprise an optical filter matrix composed of a plurality of sub-filters. Each sub-filter can have a different CWL and thus covers a different part of the optical spectrum. The sub-filters can be configured in one or more of many ways and be tiled in two dimensions, for example.

Depending on the number of sub-filters, the wavelength range accessible to the spectrometer can reach hundreds of nanometers. In embodiments comprising a plurality of sub-filters, the approximate Fourier transforms formed at the image plane (i.e. one per sub-filter) overlap, and the signal obtained at any particular pixel of the detector can result from a mixture of the different Fourier transforms.

In some embodiments the filter matrixes are arranged in a specific order to inhibit cross talk on the detector of light emerging from different filters and to minimize the effect of stray light. For example, if the matrix is composed of 3×4 filters then there are 2 filters located at the interior of the matrix and 10 filters at the periphery of the matrix. The 2 filters at the interior can be selected to be those at the edges of the wavelength range. Without being bound by a particular theory the selected inner filters may experience the most spatial cross-talk but be the least sensitive to cross-talk spectrally.

In many embodiments the spectrometer module comprises a lens array 174. The lens array can comprise a plurality of lenses. The number of lenses in the plurality of lenses can be determined such that each filter of the filter array corresponds to a lens of the lens array. Alternatively or in combination, the number of lenses can be determined such that each channel through the support array corresponds to a lens of the lens array. Alternatively or in combination, the number of lenses can be selected such that each region of the plurality of regions of the image sensor corresponds to an optical channel and corresponding lens of the lens array and filter of the filter array.

In many embodiments, the spectrometer system comprises detector 190, which may comprise an array of sensors. In many embodiments, the detector is capable of detecting light in the wavelength range of interest. The compact spectrometer system disclosed herein can be used from the UV to the IR, depending on the nature of the spectrum being obtained and the particular spectral properties of the sample being tested. The detector can be sensitive to one or more of ultraviolet wavelengths of light, visible wavelengths of light, or infrared wavelengths of light. In some embodiments, a detector that is capable of measuring intensity as a function of position (e.g. an array detector or a two-dimensional image sensor) is used.

In some embodiments the spectrometer does not comprise a cylindrical beam volume hologram (CVBH).

The detector can be located in a predetermined plane. The predetermined plane can be the focal plane of the lens array. Light of different wavelengths (X1, X2, X3, X4, etc.) can arrive at the detector as a series of substantially concentric circles of different radii proportional to the wavelength. The relationship between the wavelength and the radius of the corresponding circle may not be linear.

The detector, in some embodiments, receives non-continuous spectra, for example spectra that can be unlike a dispersive element would create. The non-continuous spectra can be missing parts of the spectrum. The non-continuous spectrum can have the wavelengths of the spectra at least in part spatially out of order, for example. In some embodiments, first short wavelengths contact the detector near longer wavelengths, and second short wavelengths contact the detector at distances further away from the first short wavelengths than the longer wavelengths.

The detector may comprise a plurality of detector elements, such as pixels for example. Each detector element may be configured so as to receive signals of a broad spectral range. The spectral range received on a first and second pluralities of detector elements may extend at least from about 10 nm to about 400 nm. In many embodiments, spectral range received on the first and second pluralities of detector elements may extend at least from about 10 nm to about 700 nm. In many embodiments, spectral range received on the first and second pluralities of detector elements may extend at least from about 10 nm to about 1600 nm. In many embodiments, spectral range received on the first and second pluralities of detector elements may extend at least from about 400 nm to about 1600 nm. In many embodiments, spectral range received on the first and second pluralities of detector elements may extend at least from about 700 nm to about 1600 nm.

In many embodiments, the spectrometer system comprises a diffuser. In embodiments in which the light emanating from the sample is not sufficiently diffuse, a diffuser can be placed in front of other elements of the spectrometer. The diffuser can be placed in a light path between a light emission and a detector and/or filter. Collimated (or partially collimated light) can impinge on the diffuser, which then produces diffuse light which then impinges on other aspects of the spectrometer, e.g. an optical filter.

In many embodiments the lens array, the filter matrix, and the detector are not centered on a common optical axis. In many embodiments the lens array, the filter matrix, and the detector are aligned on a common optical axis.

In many embodiments, the principle of operation of compact spectrometer comprises one or more of the following attributes. Light impinges upon the diffuser and at least a fraction of the light is transmitted through the diffuser. The light next impinges upon the filter matrix at a wide range of propagation angles and the spectrum of light passing through the sub-filters is angularly encoded. The angularly encoded light then passes through the lens array (e.g. Fourier transform focusing elements) which performs (approximately) a spatial Fourier transform of the angle-encoded light, transforming it into a spatially-encoded spectrum. Finally the light reaches the detector. The location of the detector element relative to the optical axis of a lens of the array corresponds to the wavelength of light, and the wavelength of light at a pixel location can be determined based on the location of the pixel relative to the optical axis of the lens of the array. The intensity of light recorded by the detector element such as a pixel as a function of position (e.g. pixel number or coordinate reference location) on the sensor corresponds to the resolved wavelengths of the light for that position.

In some embodiments, an additional filter is placed in front of the compact spectrometer system in order to block light outside of the spectral range of interest (i.e. to prevent unwanted light from reaching the detector).

In embodiments in which the spectral range covered by the optical filters is insufficient, additional sub-filters with differing CWLs can be used.

In some embodiments, shutters allow for the inclusion or exclusion of light from part of the spectrometer 102. For example, shutters can be used to exclude particular sub-filters. Shutters may also be used to exclude individual lens.

Figure 5:
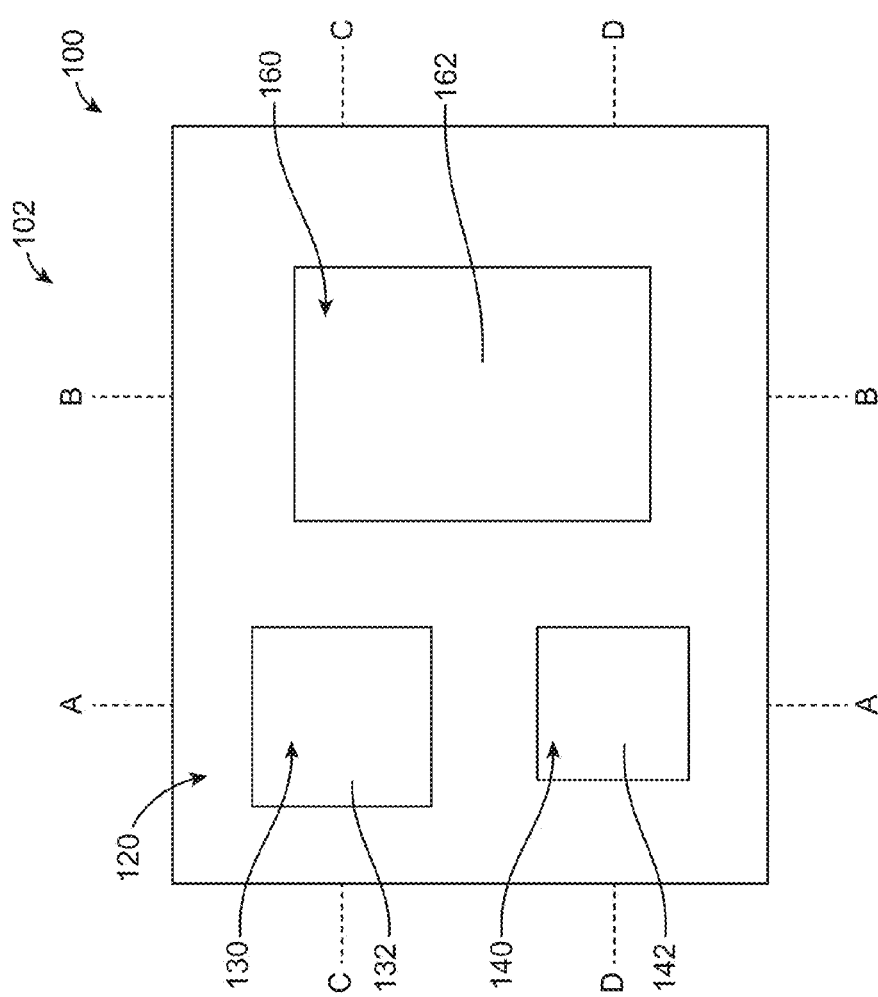
FIG. 5 shows a schematic diagram of a spectrometer head, in accordance with embodiments.

FIG. 5 shows a schematic diagram of spectrometer head in accordance with embodiments. In many embodiments, the spectrometer 102 comprises a spectrometer head 120. The spectrometer head comprises one or more of a spectrometer module 160, a temperature sensor module 130, and an illumination module 140. Each module, when present, can be covered with a module window. For example, the spectrometer module 160 can comprise a spectrometer window 162, the temperature sensor module 130 can comprise a sensor window 132, and the illumination module 140 can comprise an illumination window 142.

In many embodiments, the illumination module and the spectrometer module are configured to have overlapping fields of view at the sample. The overlapping fields of view can be provided in one or more of many ways. For example, the optical axes of the illumination source, the temperature sensor and the matrix array can extend in a substantially parallel configuration. Alternatively, one or more of the optical axes can be oriented toward another optical axis of another module.

Figure 6:
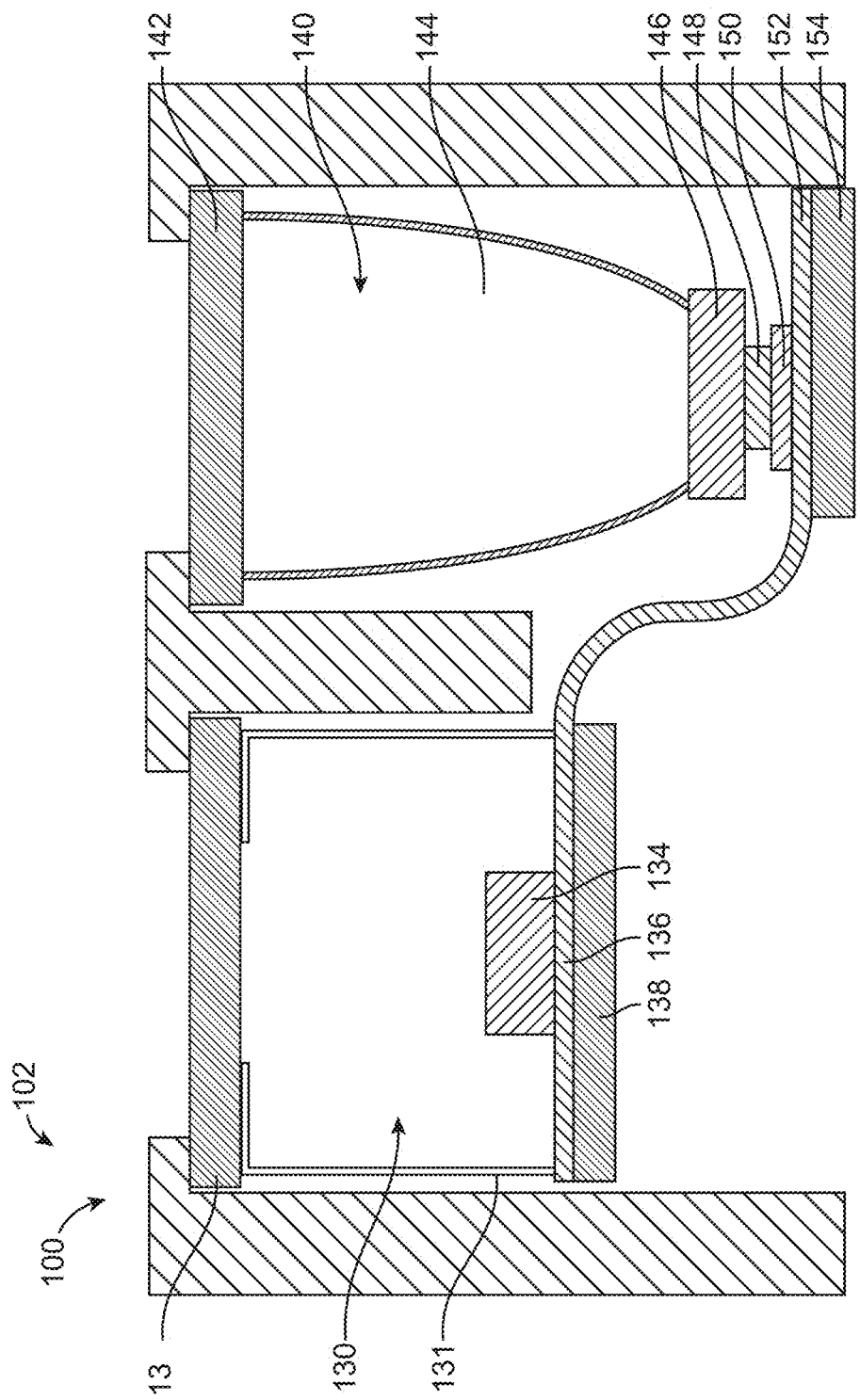
FIG. 6 shows a schematic drawing of cross-section A of the spectrometer head of FIG. 5, in accordance with embodiments.

FIG. 6 shows a schematic drawing of cross-section A of the spectrometer head of FIG. 3, in accordance with embodiments. In order to lessen the noise and/or spectral shift produced from fluctuations in temperature, a spectrometer head 102 comprising a temperature sensor module 130 can be used to measure and record the temperature during the measurement. In some embodiments, the temperature sensor element can measure the temperature of the sample in response to infrared radiation emitted from the sample, and transmit the temperature measurement to a processor. Accurate and/or precise temperature measurement can be used to standardize or modify the spectrum produced. For example, different spectra of a given sample can be measured based on the temperature at which the spectrum was taken. In some embodiments, a spectrum can be stored with metadata relating to the temperature at which the spectrum was measure. In many embodiments, the temperature sensor module 130 comprises a temperature sensor window 132. The temperature sensor window can seal the sensor module. The temperature sensor window 132 can be made of material that is substantially non-transmissive to visible light and transmits light in the infrared spectrum. In some embodiments the temperature sensor window 132 comprises germanium, for example. In some embodiments, the temperature sensor window is about 0.2, 0.3, 0.4, 0.5, 0.6, 0.7, 0.8, 0.9 or 1.0 mm thick.

In many embodiments, the spectrometer head comprises illumination module 140. The illumination module can illuminate a sample with light. In some embodiments, the illumination module comprises an illumination window 142. The illumination window can seal the illumination module. The illumination window can be substantially transmissive to the light produced in the illumination module. For example, the illumination window can comprise glass. The illumination module can comprise a light source 148. In some embodiments, the light source can comprise one or more light emitting diodes (LED). In some embodiments, the light source comprises a blue LED. In some embodiments, the light source comprises a red or green LED or an infrared LED.

The light source 148 can be mounted on a mounting fixture 150. In some embodiments, the mounting fixture comprises a ceramic package. For example, the light fixture can be a flip-chip LED die mounted on a ceramic package. The mounting fixture 150 can be attached to a flexible printed circuit board (PCB) 152 which can optionally be mounted on a stiffener 154 to reduce movement of the illumination module. The flex PCB of the illumination module and the PCT of temperature sensor modules may comprise different portions of the same flex PCB, which may also comprise portions of spectrometer PCB.

The wavelength of the light produced by the light source 148 can be shifted by a plate 146. Plate 146 can be a wavelength shifting plate. In some embodiments, plate 146 comprises phosphor embedded in glass. Alternatively or in combination, plate 146 can comprise a nano-crystal, a quantum dot, or combinations thereof. The plate can absorb light from the light source and release light having a frequency lower than the frequency of the absorbed light. In some embodiments, a light source produces visible light, and plate 146 absorbs the light and emits near infrared light. In some embodiments, the light source is in close proximity to or directly touches the plate 146. In some embodiments, the light source and associated packaging is separated from the plate by a gap to limit heat transfer. For example the gap between the light source and the plate can be at least 0.1, 0.2, 0.3, 0.4, 0.5, 0.6, 0.7, 0.8, 0.9, 1.0, 1.5, 2.0, 2.5, 3.0, 3.5, 4.0, 5.0, 6.0, 7.0, 8.0, 9.0, or 10.0 mm. In many alternative embodiments, the light source packaging touches the plate 146 in order to conduct heat from the plate such that the light source packaging comprises a heat sink.

The illumination module can further comprise a light concentrator such as a parabolic concentrator 144 or a condenser lens in order to concentrate the light. In some embodiments, the parabolic concentrator 144 is a reflector. In some embodiments, the parabolic concentrator 144 comprises stainless steel. In some embodiments, the parabolic concentrator 144 comprises gold-plated stainless steel. In some embodiments, the concentrator can concentrate light to a cone. For example, the light can be concentrated to a cone with a field of view of about 30-45, 25-50, or 20-55 degrees.

In some embodiments, the illumination module is configured to transmit light and the spectrometer module is configured to receive light along optical paths extending substantially perpendicular to an entrance face of the spectrometer head. In some embodiments, the modules can be configured to such that light can be transmitted from one module to an object (such as a sample 108) and reflected or scattered to another module which receives the light.

In some embodiments, the optical axes of the illumination module and the spectrometer module are configured to be non-parallel such that the optical axis representing the spectrometer module is at an offset angle to the optical axis of the illumination module. This non-parallel configuration can be provided in one or more of many ways. For example, one or more components can be supported on a common support and offset in relation to an optic such as a lens in order to orient one or more optical axes toward each other. Alternatively or in combination, a module can be angularly inclined with respect to another module. In some embodiments, the optical axis of each module is aligned at an offset angle of greater than 1, 2, 3, 4, 5, 6, 7, 8, 9, 10, 12, 14, 16, 18, 20, 25, 30, 35, 40, 45, or 50 degrees. In some embodiments, the illumination module and the spectrometer module are configured to be aligned at an offset angle of less than 1, 2, 3, 4, 5, 6, 7, 8, 9, 10, 12, 14, 16, 18, 20, 25, 30, 35, 40, 45, or 50 degrees. In some embodiments, the illumination module and the spectrometer module are configured to be aligned at an offset angle between than 1-10, 11-20, 21-30, 31-40 or 41-50 degrees. In some embodiments, the offset angle of the modules is set firmly and is not adjustable. In some embodiments, the offset angle of the modules is adjustable. In some embodiments, the offset angle of the modules is automatically selected based on the distance of the spectrometer head from the sample. In some embodiments, two modules have parallel optical axes. In some embodiments, two or more modules have offset optical axes. In some embodiments, the modules can have optical axes offset such that they converge on a sample. The modules can have optical axes offset such that they converge at a set distance. For example, the modules can have optical axes offset such that they converge at a distance of about 10, 20, 30, 40, 50, 60, 70, 80, 90, 100, 150, 200, 250, 300, 350, 400, or 500 mm away.

Figure 7:
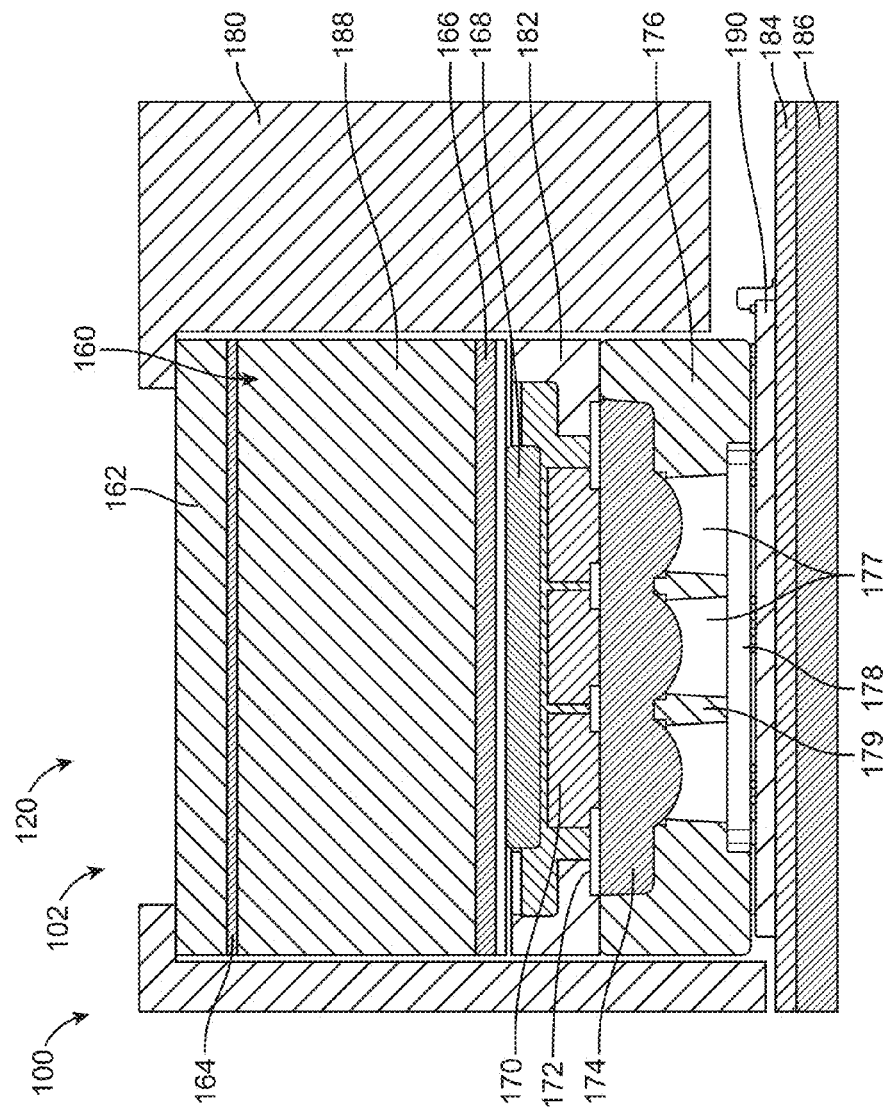
FIG. 7 shows a schematic drawing of cross-section B of the spectrometer head of FIG. 5, in accordance with embodiments.

FIG. 7 shows a schematic drawing of cross-section B of the spectrometer head of FIGS. 3 and 4, in accordance with embodiments. In many embodiments, the spectrometer head 102 comprises spectrometer module 160. The spectrometer module can be sealed by a spectrometer window 162. In some embodiments, the spectrometer window 162 is selectively transmissive to light with respect to the wavelength in order to analyze the spectral sample. For example, spectrometer window 162 can be an IR-pass filter. In some embodiments, the window 162 can be glass. The spectrometer module can comprise one or more diffusers. For example, the spectrometer module can comprise a first diffuser 164 disposed below the spectrometer window 162. The first diffuser 164 can distribute the incoming light. For example, the first diffuser can be a cosine diffuser. Optionally, the spectrometer module comprises a light filter 188. Light filter 188 can be a thick IR-pass filter. For example, filter 188 can absorb light below a threshold wavelength. In some embodiments, filter 188 absorbs light with a wavelength below about 1000, 950, 900, 850, 800, 750, 700, 650, or 600 nm. In some embodiments, the spectrometer module comprises a second diffuser 166. The second diffuser can generate Lambertian light distribution at the input of the filter matrix 170. The filter assembly can be sealed by a glass plate 168. Alternatively or in combination, the filter assembly can be further supported by a filter frame 182, which can attach the filter assembly to the spectrometer housing 180. The spectrometer housing 180 can hold the spectrometer window 162 in place and further provide mechanical stability to the module.

The first filter and the second filter can be arranged in one or more of many ways to provide a substantially uniform light distribution to the filters. The substantially uniform light distribution can be uniform with respect to an average energy to within about 25%, for example to within about 10%, for example. In many embodiments the first diffuser distributes the incident light energy spatially on the second diffuser with a substantially uniform energy distribution profile. In some embodiments, the first diffuser makes the light substantially homogenous with respect to angular distribution. The second diffuser further diffuses the light energy of the substantially uniform energy distribution profile to a substantially uniform angular distribution profile, such that the light transmitted to each filter can be substantially homogenous both with respect to the spatial distribution profile and the angular distribution profile of the light energy incident on each filter. For example, the angular distribution profile of light energy onto each filter can be uniform to within about +/−25%, for example substantially uniform to within about +/−10%.

In many embodiments, the spectrometer module comprises a filter matrix 170. The filter matrix can comprise one or more filters. In many embodiments, the filter matrix comprises a plurality of filters.

In some embodiments, each filter of the filter matrix 170 is configured to transmit a range of wavelengths distributed about a central wavelength. The range of wavelengths can be defined as a full width half maximum (hereinafter "FWHM") of the distribution of transmitted wavelengths for a light beam transmitted substantially normal to the surface of the filter as will be understood by a person of ordinary skill in the art. A wavelength range can be defined by a central wavelength and by a spectral width. The central wavelength can be the mean wavelength of light transmitted through the filter, and the band spectral width of a filter can be the difference between the maximum and the minimum wavelength of light transmitted through the filter. In some embodiments, each filter of the plurality of filters is configured to transmit a range of wavelengths different from other filters of the plurality. In some embodiments, the range of wavelengths overlaps with ranges of said other filters of the plurality and wherein said each filter comprises a central wavelength different from said other filters of the plurality.

In many embodiments, the filter array comprises a substrate having a thickness and a first side and a second side, the first side oriented toward the diffuser, the second side oriented toward the lens array. In some embodiments, each filter of the filter array comprises a substrate having a thickness and a first side and a second side, the first side oriented toward the diffuser, the second side oriented toward the lens array. The filter array can comprise one or more coatings on the first side, on the second side, or a combination thereof. Each filter of the filter array can comprise one or more coatings on the first side, on the second side, or a combination thereof. In some embodiments, each filter of the filter array comprises one or more coatings on the second side, oriented toward the lens array. In some embodiments, each filter of the filter array comprises one or more coatings on the second side, oriented toward the lens array and on the first side, oriented toward the diffuser. The one or more coatings on the second side can be an optical filter. For example, the one or more coatings can permit a wavelength range to selectively pass through the filter. Alternatively or in combination, the one or more coatings can be used to inhibit cross-talk among lenses of the array. In some embodiments, the plurality of coatings on the second side comprises a plurality of interference filters, said each of the plurality of interference filters on the second side configured to transmit a central wavelength of light to one lens of the plurality of lenses. In some embodiments, the filter array comprises one or more coatings on the first side of the filter array. The one or more coatings on the first side of the array can comprise a coating to balance mechanical stress. In some embodiments, the one or more coatings on the first side of the filter array comprises an optical filter. For example, the optical filter on the first side of the filter array can comprise an IR pass filter to selectively pass infrared light. In many embodiments, the first side does not comprise a bandpass interference filter coating. In some embodiments, the first does not comprise a coating.

In many embodiments, the array of filters comprises a plurality of bandpass interference filters on the second side of the array. The placement of the fine frequency resolving filters on the second side oriented toward the lens array and apertures can inhibit cross-talk among the filters and related noise among the filters. In many embodiments, the array of filters comprises a plurality of bandpass interference filters on the second side of the array, and does not comprise a bandpass interference filter on the first side of the array.

In many embodiments, each filter defines an optical channel of the spectrometer. The optical channel can extend from the filer through an aperture and a lens of the array to a region of the sensor array. The plurality of parallel optical channels can provide increased resolution with decreased optical path length.

The spectrometer module can comprise an aperture array 172. The aperture array can prevent cross talk between the filters. The aperture array comprises a plurality of apertures formed in a non-optically transmissive material. In some embodiments, the plurality of apertures is dimensioned to define a clear lens aperture of each lens of the array, wherein the clear lens aperture of each lens is limited to one filter of the array. In some embodiments, the clear lens aperture of each lens is limited to one filter of the array.

In many embodiments the spectrometer module comprises a lens array 174. The lens array can comprise a plurality of lenses. The number of lenses can be determined such that each filter of the filter array corresponds to a lens of the lens array. Alternatively or in combination, the number of lenses can be determined such that each channel through the support array corresponds to a lens of the lens array. Alternatively or in combination, the number of lenses can be selected such that each region of the plurality of regions of the image sensor corresponds to an optical channel and corresponding lens of the lens array and filter of the filter array.

In many embodiments, each lens of the lens array comprises one or more aspheric surfaces, such that each lens of the lens array comprises an aspherical lens. In many embodiments, each lens of the lens array comprises two aspheric surfaces. Alternatively or in combination, one or more individual lens of the lens array can have two curved optical surfaces wherein both optical surfaces are substantially convex. Alternatively or in combination, the lenses of the lens array may comprise one or more diffractive optical surfaces.

In many embodiments, the spectrometer module comprises a support array 176. The support array 176 comprises a plurality of channels 177 defined with a plurality of support structures 179 such as interconnecting annuli. The plurality of channels 177 may define optical channels of the spectrometer. The support structures 179 can comprises stiffness to add rigidity to the support array 176. The support array may comprise a stopper to limit movement and fix the position the lens array in relation to the sensor array. The support array 176 can be configured to support the lens array 174 and fix the distance from the lens array to the sensor array in order to fix the distance between the lens array and the sensor array at the focal length of the lenses of the lens array. In many embodiments, the lenses of the array comprise substantially the same focal length such that the lens array and the sensor array are arranged in a substantially parallel configuration.

The support array 176 can extend between the lens array 174 and the stopper mounting 178. The support array 176 can serve one or more purposes, such as 1) providing the correct separation distance between each lens of lens array 170 and each region of the plurality of regions of the image sensor 190, and/or 2) preventing stray light from entering or exiting each channel, for example. In some embodiments, the height of each support in support array 176 is calibrated to the focal length of the lens within lens array 174 that it supports. In some embodiments, the support array 176 is constructed from a material that does not permit light to pass such as substantially opaque plastic. In some embodiments, support array 176 is black, or comprises a black coating to further reduce cross talk between channels. The spectrometer module can further comprise a stopper mounting 178 to support the support array. In many embodiments, the support array comprises an absorbing and/or diffusive material to reduce stray light, for example.

In many embodiments, the support array 176 comprises a plurality of channels having the optical channels of the filters and lenses extending therethrough. In some embodiments, the support array comprise a single piece of material extending from the lens array to the detector (i.e. CCD or CMOS array).

The lens array can be directly attached to the aperture array 172, or can be separated by an air gap of at least 1, 2, 3, 4, 5, 6, 7, 8, 9, 10, 12, 14, 16, 18, 20, 30, 40, or 50 micrometers. The lens array can be directly on top of the support array 178. Alternatively or in combination, the lens array can be positioned such that each lens is substantially aligned with a single support stopper or a single optical isolator in order to isolate the optical channels and inhibit cross-talk. In some embodiments, the lens array is positioned to be at a distance approximately equal to the focal length of the lens away from the image sensor, such that light coming from each lens is substantially focused on the image sensor.

In some embodiments, the spectrometer module comprises an image sensor 190. The image sensor can be a light detector. For example, the image sensor can be a CCD or 2D CMOS or other sensor, for example. The detector can comprise a plurality of regions, each region of said plurality of regions comprising multiple sensors. For example, a detector can be made up of multiple regions, wherein each region is a set of pixels of a 2D CMOS. The detector, or image sensor 190, can be positioned such that each region of the plurality of regions is directly beneath a different channel of support array 176. In many embodiments, an isolated light path is established from a single of filter of filter array 170 to a single aperture of aperture array 172 to a single lens of lens array 174 to a single stopper channel of support array 176 to a single region of the plurality of regions of image sensor 190. Similarly, a parallel light path can be established for each filter of the filter array 170, such that there are an equal number of parallel (non-intersecting) light paths as there are filters in filter array 170.

The image sensor 190 can be mounted on a flexible printed circuit board (PCB) 184. The PCB 184 can be attached to a stiffener 186. In some embodiments, the stiffener comprises a metal stiffener to prevent motion of the spectrometer module relative to the spectrometer head 120.

Figure 8:
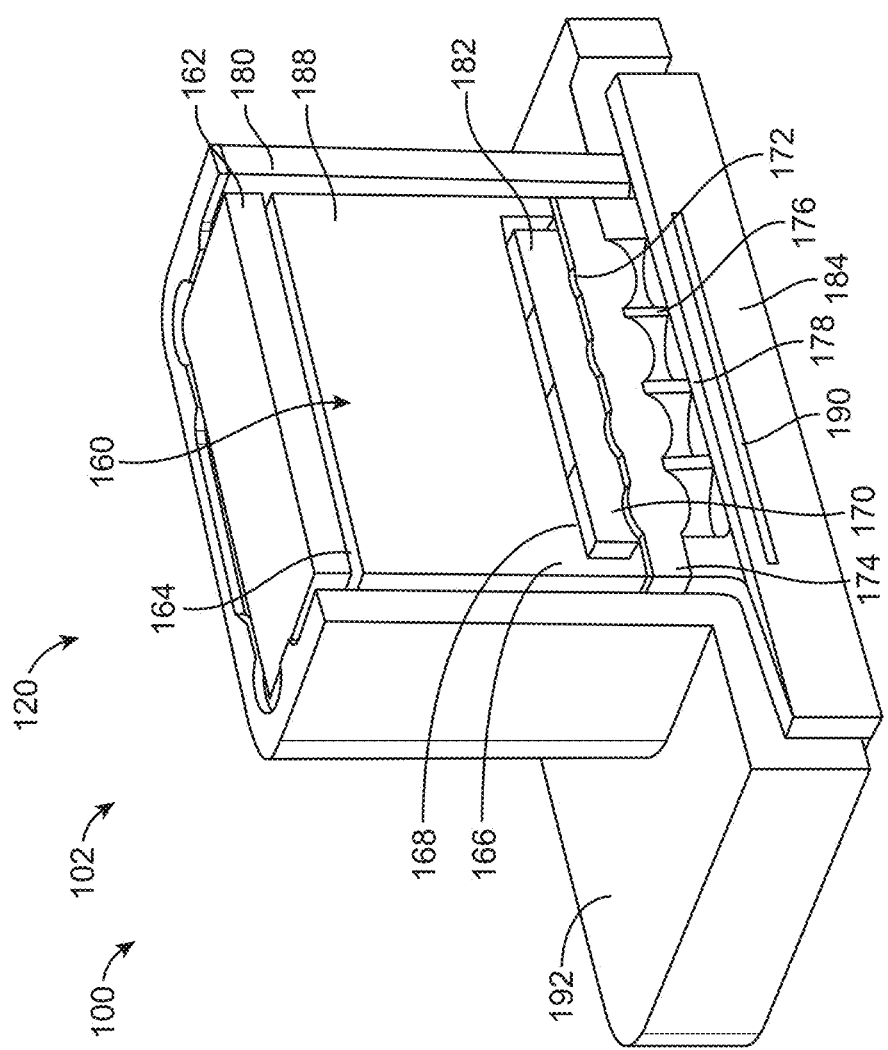
FIG. 8 shows an isometric view of a spectrometer module in accordance with embodiments.

FIG. 8 shows an isometric view of a spectrometer module 160 in accordance with embodiments. The spectrometer module 160 comprises many components as described herein. In many embodiments, the support array 176 can be positioned on a package on top of the sensor. In many embodiments, the support array can be positioned over the top of the bare die of the sensor array such that an air gap is present. The air gap can be less than 10, 9, 8, 7, 6, 5, 4, 3, 2 or 1 micrometer(s).

Figure 9:
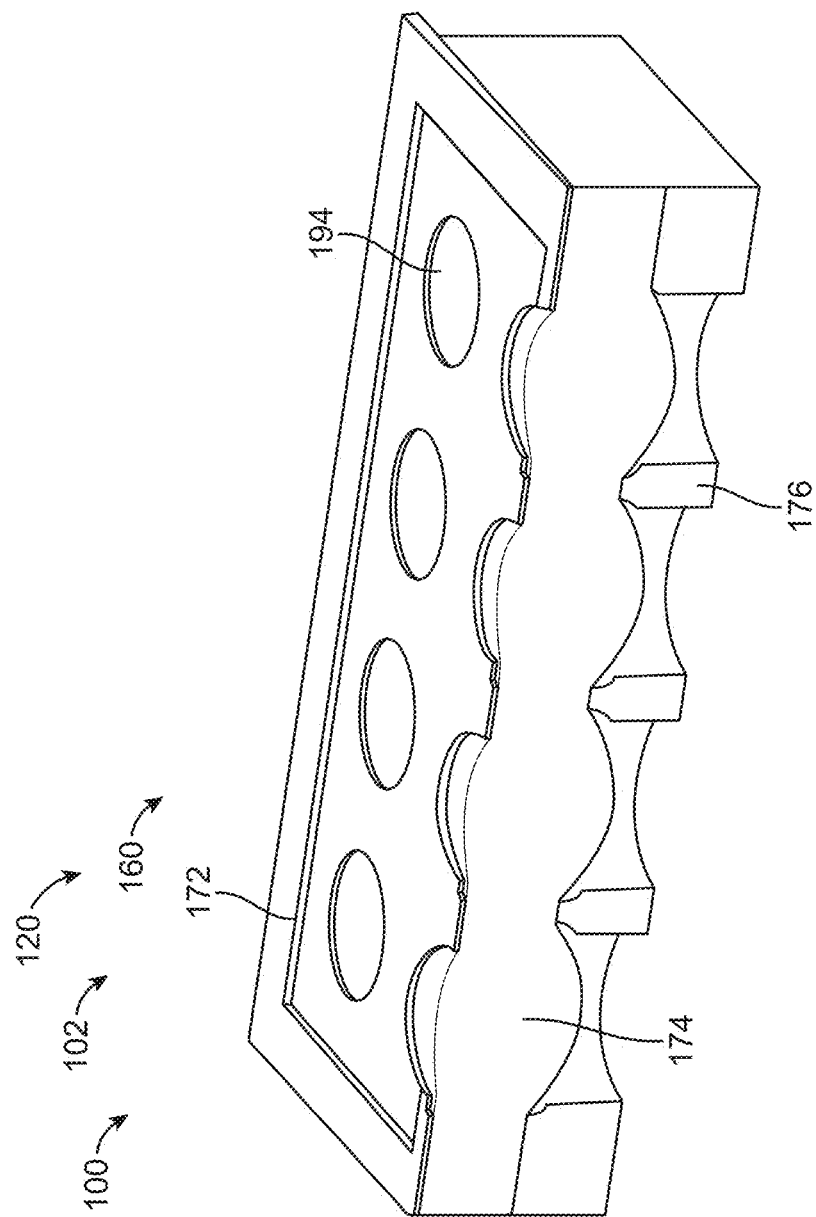
FIG. 9 shows the lens array within the spectrometer module, in accordance with embodiments.

FIG. 9 shows the lens array 174 within the spectrometer module 160, in accordance with embodiments. This isometric view shows the apertures 194 formed in a non-transmissive material of the aperture array 172 in accordance with embodiments. In many embodiments, each channel of the support array 176 is aligned with a filter of the filter array 170, a lens of the lens array 174, and an aperture 194 of the aperture array in order to form a plurality of light paths with inhibited cross talk.

In some embodiments, the glass-embedded phosphor of plate 146 may be a near-infrared (NIR) phosphor, capable of emitting infrared or NIR radiation in the range from about 700 nm to about 1100 nm.

In some embodiments, the light filter 188 is configured to block at least a portion of visible radiation included in the incident light.

In some embodiments, first wavelength range of the first filter and the second wavelength range of the second filter fall within a wavelength range of about 400 nm to about 1100 nm. In some embodiments, the second wavelength range overlaps the first wavelength range by at least 2% of the second wavelength range. In some embodiments, the second wavelength range overlaps the first wavelength range by an amount of about 1% to about 5% of the second wavelength range. The overlap in the range of wavelengths of the filters may be configured to provide algorithmic correction of the gains across different channels, for example across the outputs of a first filter element and a second filter element.

In some embodiments, the coating of the filter array and/or the support array may comprise a black coating configured to absorb most of the light that hits the coated surface. For example, the coating may comprise a coating commercially available from Anoplate (as described on http://www.anoplate.com/capabilities/anoblack_ni.html), Acktar (as described on the world wide web at the Acktar website, www.acktar.com), or Avian Technologies (as described on http://www.aviantechnologies.com/products/coatings/diffuse_black.php), or other comparable coatings.

In some embodiments, the stopper and the image sensor may be configured to have matching coefficients of thermal expansion (CTE). For example, the stopper and the image sensor may be configured to have a matching CTE of about $7 \cdot 10^{-6}$ $K^{-1}$. In order to match the CTE between the stopper and the image sensor where the stopper and image sensor have different CTEs, a liquid crystal polymer, such as Vectra E130, may be applied between the stopper and the image sensor.

In many embodiments, the lens may be configured to introduce some distortion in the output of the lens, in order to improve performance in analyzing the obtained spectral data. The filters described herein may typically allow transmission of a specific wavelength for a specific angle of propagation of the incident light beam. As the light transmitted through the filters pass through the lens, the output of the lens may generate concentric rings on the sensor for different wavelengths of incident light. With typical spherical lens performance, as the angle of incidence grows larger, the concentric ring for that wavelength becomes much thinner (for a typical light bandwidth of ~5 nm). Such variance in the thickness of the rings may cause reduced linearity and related performance in analyzing the spectral data. To overcome this non-linearity, some distortion may be introduced into the lens, so as to reduce the thickness of the rings that correspond to incident light having smaller angles of propagation, and increase the thickness of the rings that correspond to incident light having larger angles of propagation, wherein non-linearity of ring size related to incident angle is decreased. Lenses configured to produce such distortion in the output can produce a more even distribution of ring thicknesses along the supported range of angles of incidence, consequently improving performance in the analysis of the generated spectral data. The distortion can be provided with one or more aspheric lens profiles to increase the depth of field (DoF) and increase the size of the point spread function (PSF) as described herein.

Figure 10:
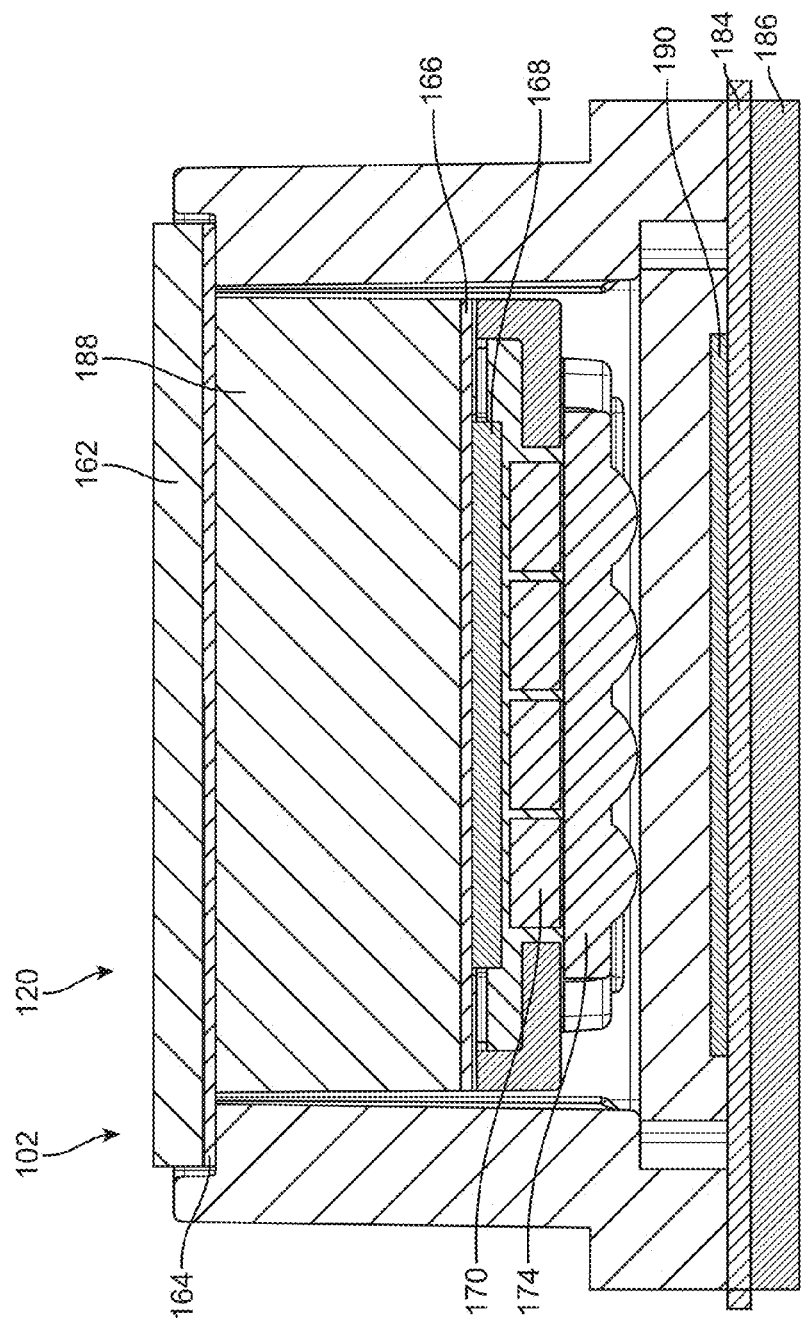
FIG. 10 shows a schematic diagram of an alternative embodiment of the spectrometer head, in accordance with embodiments.

FIG. 10 shows a schematic drawing of a cross-section B of an alternative embodiment of the spectrometer head of FIG. 5. In some embodiments, the spectrometer module may be configured to purposefully induce cross-talk among sensor elements. For example, the spectrometer module may comprise the filter matrix and lens array as shown in FIG. 7, but omit one or more structural features that isolate the optical channels, such as the aperture array 172 or the isolated channels 177 of the support array 176. Without the isolated optical channels, light having a particular wavelength received by the first filter may result in a pattern of non-concentric rings on the detector. In addition, a first range of wavelengths associated with a first filter may partially overlap a second range of wavelengths associated with a second filter. Without the isolated optical channels, at least one feature in the pattern of light output by a first filter may be associated with at least one feature in the pattern of light output by a second filter. For example, when light comprising two different wavelengths, separated by at least five times the spectral resolution of the device, passes through the filter matrix, the light from at least two filters of the filter matrix may impinge on at least one common pixel of the detector. The spectrometer module may further comprise at least one processing device configured to stitch together light output by multiple filters to generate or reconstruct a spectrum associated with the incident light. Inducing cross-talk among sensor elements can have the advantage of increasing signal strength, and of reducing the structural complexity and thereby the cost of the optics.

Spectrometer Using Multiple Illumination Sources

Figure 11:
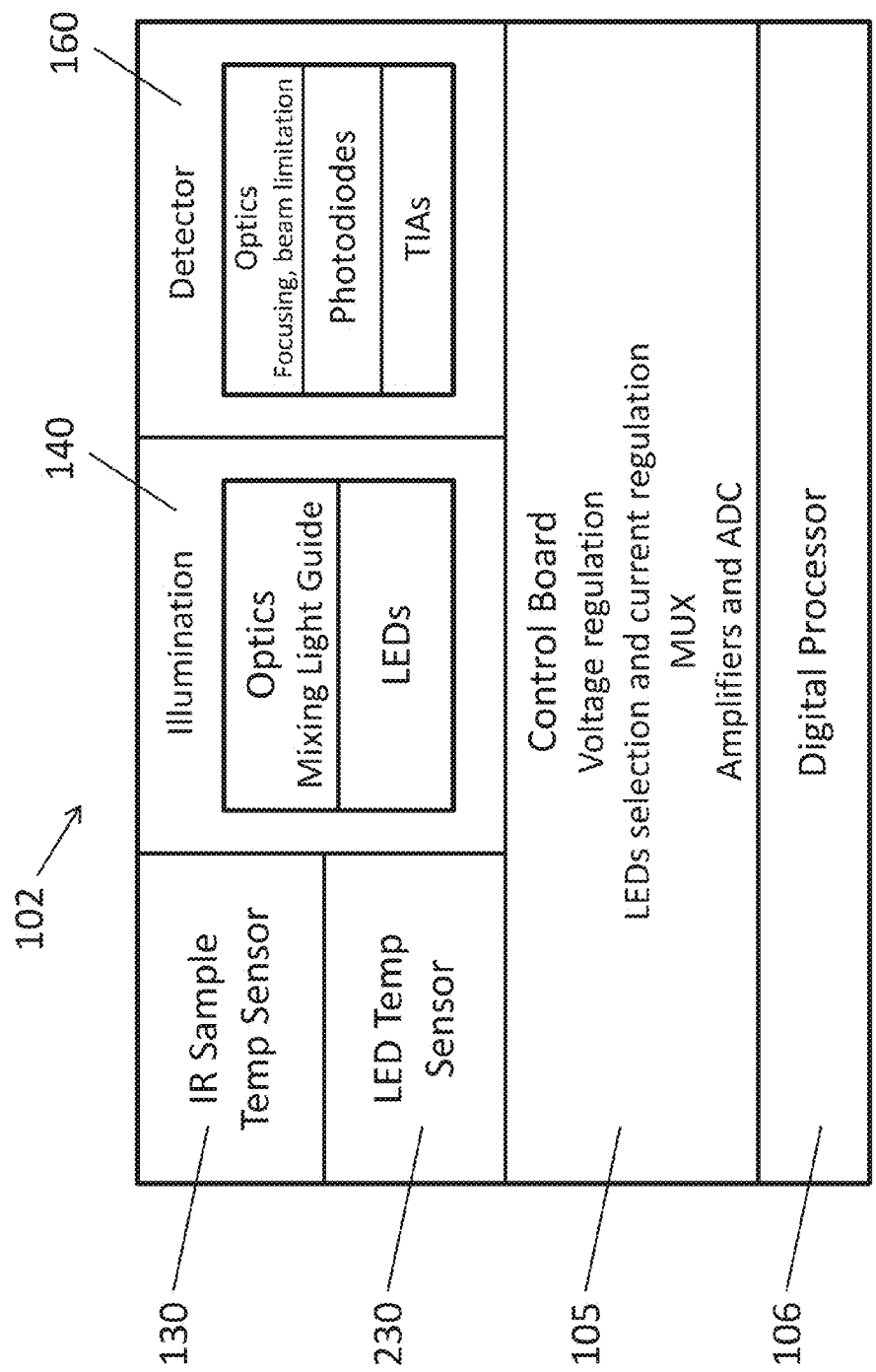
FIG. 11 shows a schematic diagram of an alternative embodiment of the spectrometer head, in accordance with embodiments.

FIG. 11 shows a schematic diagram of an alternative embodiment of the spectrometer head 102. The spectrometer head 102 comprises an illumination module 140, a spectrometer module 160, a control board 105, and a processor 106. The spectrometer 102 further comprises a temperature sensor module 130 as described herein, configured to measure and record the temperature of the sample in response to infrared radiation emitted from the sample. In addition to the temperature sensor module 130, the spectrometer 102 may also comprise a separate temperature sensor 230 for measuring the temperature of the light source in the illumination module 140.

Figure 12:
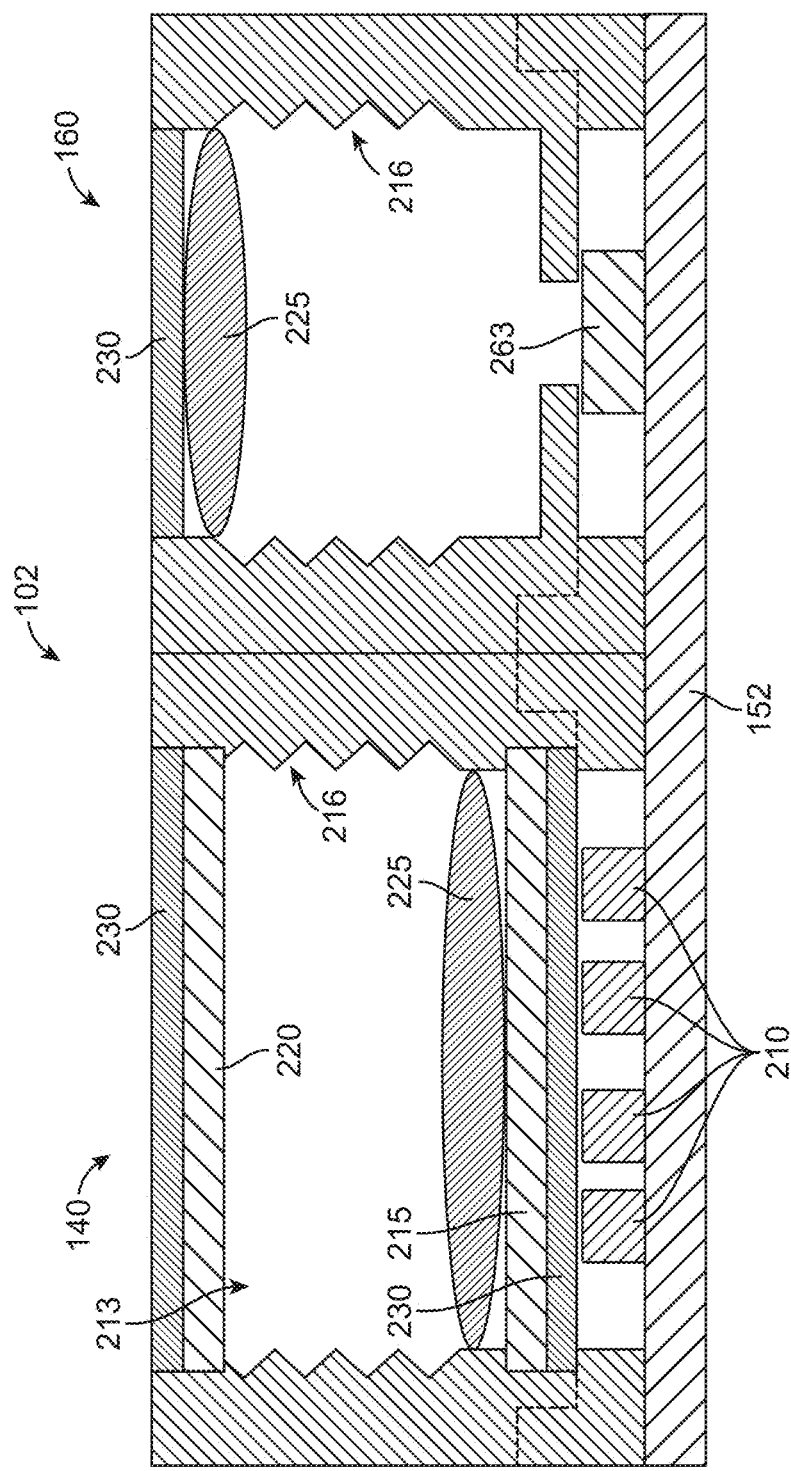
FIG. 12 shows a schematic diagram of a cross-section of the spectrometer head of FIG. 11.

FIG. 12 shows a schematic diagram of a cross-section of the spectrometer head of FIG. 11 (the sample temperature sensor 130 and the light source temperature sensor 230 are not shown). The spectrometer head comprises an illumination module 140 and a spectrometer module 160.

The illumination module 140 comprises at least two light sources, such as light-emitting diodes (LEDs) 210. The illumination module may comprise at least about 10 LEDs. The illumination module 140 further comprises a radiation diffusion unit 213 configured to receive the radiation emitted from the array of LEDs 210, and provide as an output illumination radiation for use in analyzing a sample material. The radiation diffusion unit may comprise one or more of a first diffuser 215, a second diffuser 220, and one lens 225 disposed between the first and second diffusers. The radiation diffusion unit may further comprise additional diffusers and lenses. The radiation diffusion unit may comprise a housing 214 to support the first diffuser and the second diffuser with fixed distances from the light sources. The inner surface of the housing 214 may comprise a plurality of light absorbing structures 216 to inhibit reflection of light from an inner surface of the housing. For example, the plurality of light absorbing structures may comprise one or more of a plurality of baffles or a plurality of threads, as shown in FIG. 12. A cover glass 230 may be provided to mechanically support and protect each diffuser. Alternatively or in combination with the LEDs, the at least two light sources may comprise one or more lasers.

The array of LEDs 210 may be configured to generate illumination light composed of multiple wavelengths. Each LED may be configured to emit radiation within a specific wavelength range, wherein the wavelength ranges of the plurality of LEDs may be different. The LEDs may have different specific power, peak wavelength and bandwidth, such that the array of LEDs generates illumination that spans across the spectrum of interest. There can be between a few LEDs and a few tens of LEDs in a single array.

Figure 13:
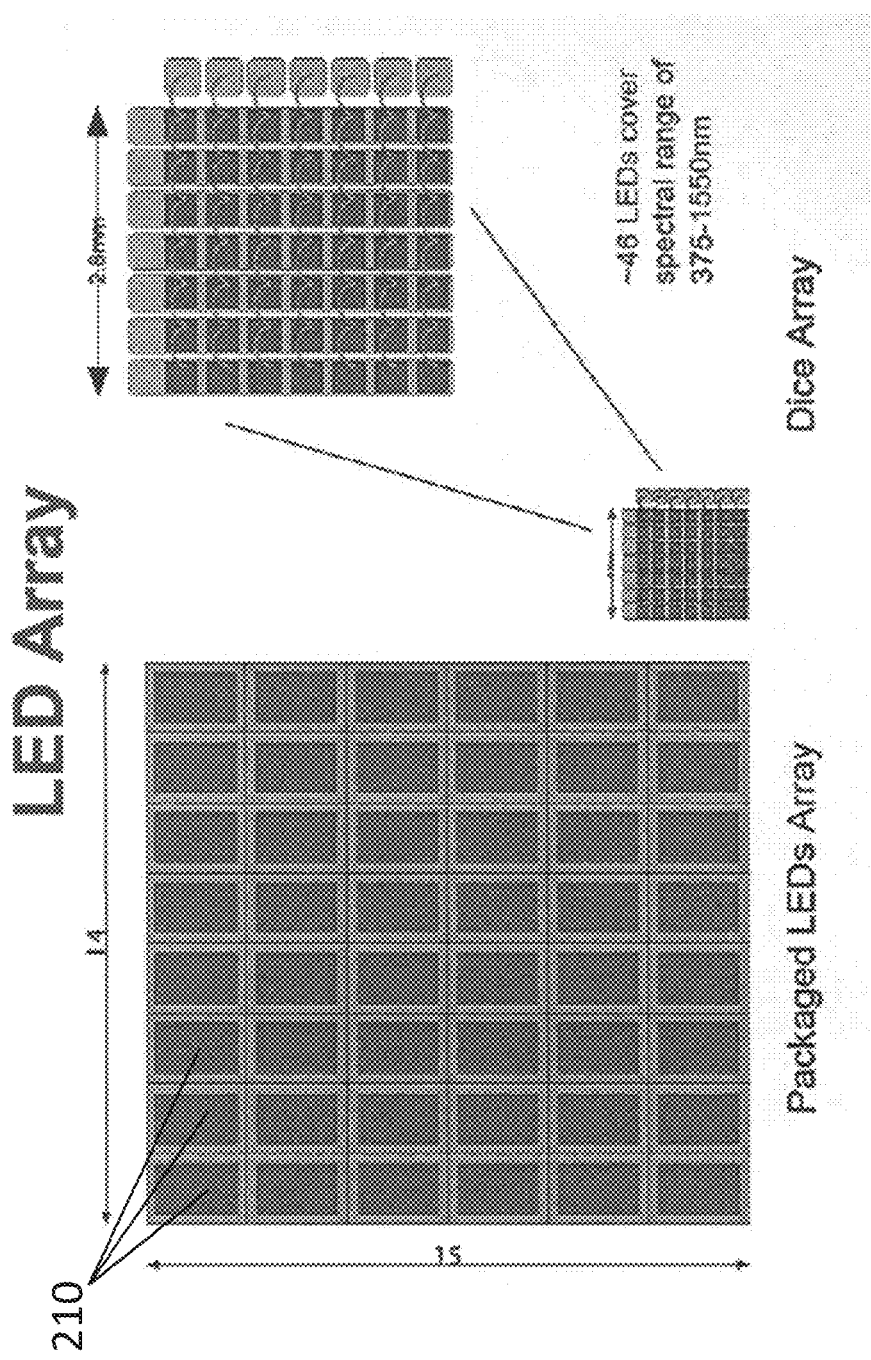
FIG. 13 shows an array of LEDs of the spectrometer head of FIG. 11 arranged in rows and columns, in accordance with embodiments.

In some embodiments, the LED array is placed on a printed circuit board (PCB) 152. In order to reduce the size, cost and complexity of the PCB and LED driving electronics and reduce the number of interconnect lines, the LEDs may preferably be arranged in rows and columns, as shown in FIG. 13. All anodes on the same row may be connected together and all cathodes on the same column may be connected together (or vice versa). For example, the LED in the center of the array may be turned on when a transistor connects the driving voltage to the anodes' fourth row and another transistor connects the cathodes' fourth column to a ground. None of the other LEDs is turned on at this state, as either its anodes are disconnected from power or its cathodes are disconnected from the ground. Preferably, the LEDs are arranged according to voltage groups, to simplify the current control and to improve spectral homogeneity (LEDs of similar wavelengths are placed close together). While bi-polar transistors are provided herein as examples, the circuit may also use other types of switches (e.g., field-effect transistors).

The LED currents can be regulated by various means as known to those skilled in the art. In some embodiments, Current Control Regulator (CCR) components may be used in series to each anode row and/or to each cathode column of the array. In some embodiments, a current control loop may be used instead of the CCR, providing more flexibility and feedback on the actual electrode currents. Alternatively, the current may be determined by the applied anode voltages, though this method should be used with care as LEDs can vary significantly in their current to voltage characteristics.

An optional voltage adjustment diode can be useful in reducing the difference between the LED driving voltages of LEDs sharing the same anode row, so that they can be driven directly from the voltage source without requiring a current control circuit. The optional voltage adjustment diode can also help to improve the stability and simplicity of the driving circuit. These voltage adjustment diodes may be selected according to the LEDs' expected voltage drops across the row, in opposite tendency, so that the total voltage drop variation along a shared row is smaller.

Referring to FIG. 12, the radiation diffusion unit 213, positioned above the LED array, is configured to mix the illumination emitted by each of the LEDs at different spatial locations and with different angular characteristics, such that the spectrum of illumination of the sample will be as uniform as possible across the measured area of the sample. What is meant by a uniform spectrum is that the relations of powers at different wavelengths do not depend on the location on the sample. However, the absolute power can vary. This uniformity is highly preferable in order to optimize the accuracy of the reflection spectrum measurement.

Figure 14:
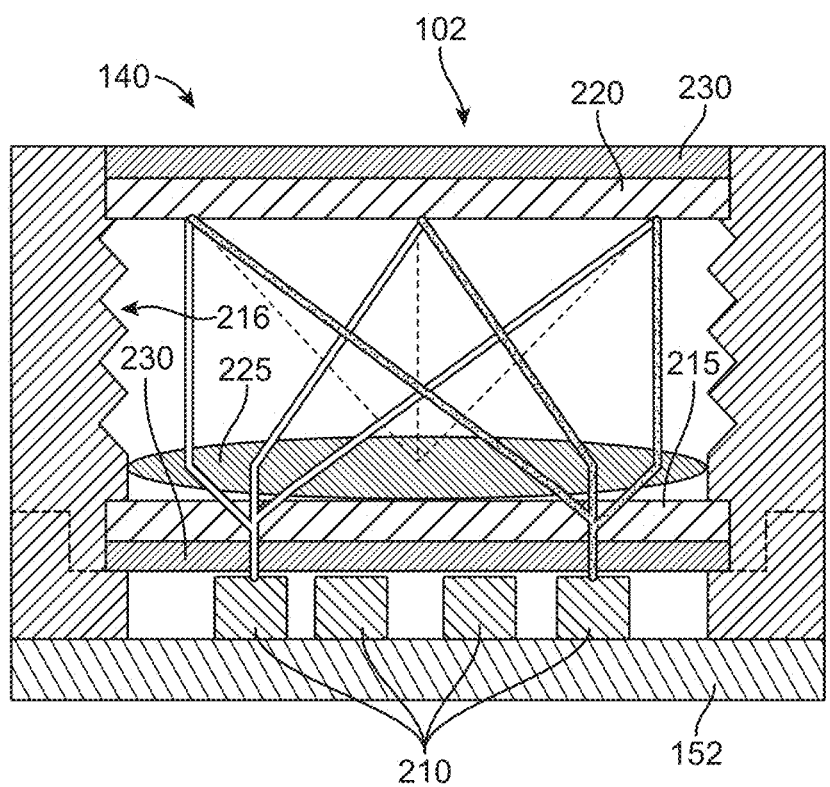
FIG. 14 shows a schematic diagram of a radiation diffusion unit of the spectrometer head of FIG. 11, in accordance with embodiments.

The first diffuser 215, preferably mechanically supported and protected by a cover glass 230, may be placed above the array of LEDs 210. The diffuser may be configured to equalize the beam patterns of the different LEDs, as the LEDs will typically differ in their illumination profiles. Regardless of the beam shape of any LED, the light that passes through the first diffuser 215 can be configured to have a Lambertian beam profile, such that the emitted spectrum at each of the directions from first diffuser 215 is uniform. Ideally, the ratios between the illuminations at different wavelengths do not depend on the direction to the plane of the first diffuser 215, as observed from infinity. Such directions are indicated schematically by the dashed lines shown in FIG. 14, referring to the directions of rays at the output of the first diffuser 215 towards the first surface of lens 225.

The first diffuser 215 is preferably placed at the aperture plane of the lens 225. Thus, parallel rays can be focused by the lens to the same location on the focal plane of the lens, where the second diffuser 220 is placed (preferably supported and protected by cover glass 230). Since all illumination directions at the output of the first diffuser 215 have the same spectrum, the spectrum at the input plane of the second diffuser 220 can be uniform (though the absolute power may vary). The second diffuser 220 can then equalize the beam profiles from each of the locations in its plane, so that the output spectrum is uniform both in location and in direction, leading to uniform spectral illumination across the sample irrespective of the sample distance from the device (when the sample is close to the device it is more affected by the spatial variance of spectrum, and when the sample is far from the device it is more affected by the angular variation of the spectrum).

Figure 15A:
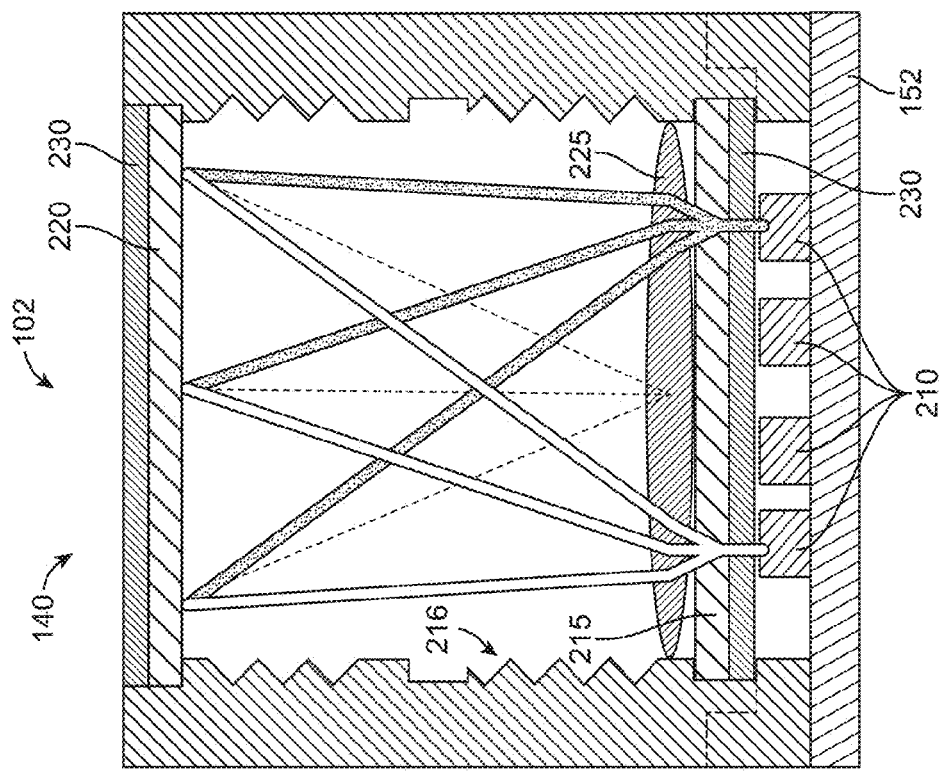
FIGS. 15A and 15B show examples of design options for the radiation diffusion unit of FIG. 13, in accordance with embodiments.
Figure 15B:
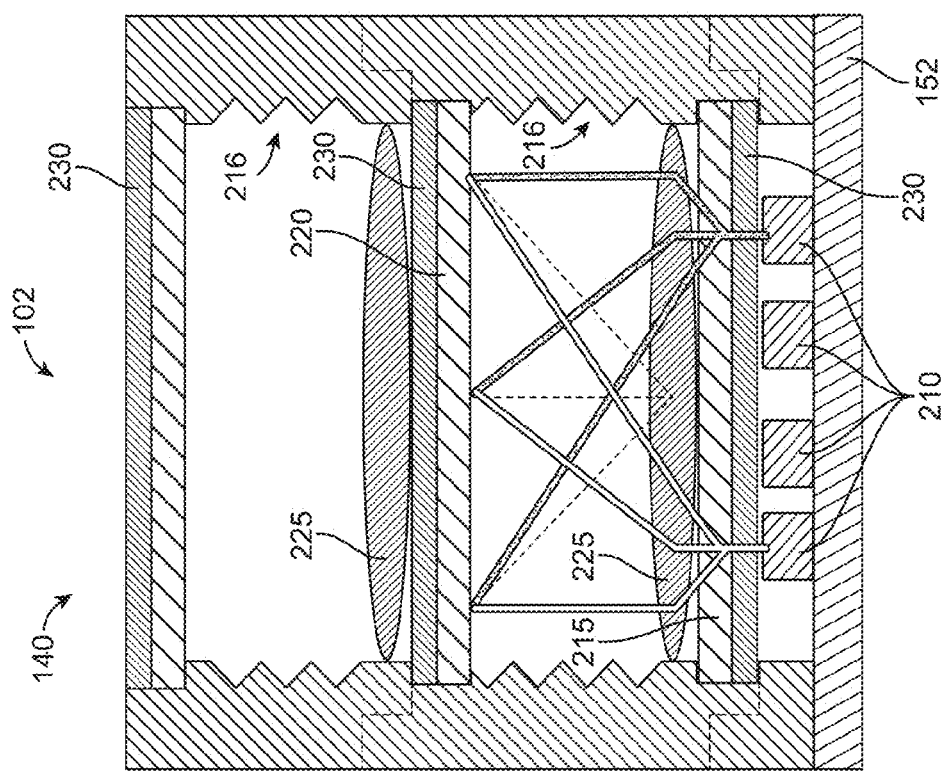

In designing the radiation diffusion unit 213 configured to improve spectral uniformity, size and power may be traded off in order to achieve the required spectral uniformity. For example, as shown in FIG. 15A, the radiation diffusion unit 213 may be duplicated (additional diffusers and lenses added), or as shown in FIG. 15B, the radiation diffusion unit 213 may be configured with a longer length between the first and second diffusers, in order to achieve increased uniformity while trading off power. Alternatively, if uniformity is less important, some elements in the optics can be omitted (e.g., first diffuser or lens), or simplified (e.g., weaker diffuser, simpler lens).

Referring back to FIG. 12, the spectrometer module 160 comprises one or more photodiodes 263 that are sensitive to the spectral range of interest. For example, a dual Si—InGaAs photodiode can be used to measure the sample reflection spectrum in the range of about 400 nm to about 1750 nm. The dual photodiode structure is composed of two different photodiodes positioned one above the other, such that they collect illumination from essentially the same locations in the sample.

The one or more photodiodes 263 are preferably placed at the focal plane of lens 225, as shown in FIG. 12. The lens 225 can efficiently collect the light from a desired area in the sample to the surface of the photodiode. Alternatively, other light collection methods known in the art can be used, such as a Compound Parabolic Concentrator.

The photodiode current can be detected using a transimpedance amplifier. For the dual photodiode architecture embodiment, the photocurrent can first be converted from current to voltage using resistors with resistivity that provides high gain on the one hand to reduce noise, while having a wide enough bandwidth and no saturation on the other hand. An operational amplifier can be connected in photovoltaic mode amplification to the photodiodes, for minimum noise. Voltage dividers can provide a small bias to the operational amplifier (Op Amp) to compensate for possible bias current and bias voltage at the Op Amp input. Additional amplification may be preferable with voltage amplifiers.

In the embodiment of the spectrometer head shown in FIG. 12, each photodiode 263 is responsive to the illumination from typically many LEDs (or wavelengths). In order to identify the relative contribution of light from each of the LEDs, the LED current may be modulated, then the detected photocurrent of the photodiodes may be demodulated.

In some embodiments, the modulation/demodulation may be achieved by time division multiplexing (TDM). In TDM, each LED is switched "on" in a dedicated time slot, and the photocurrent sampled in synchronization to that time slot represents the contribution of the corresponding LED and its wavelength. Black level and ambient light is measured at the "off" times between "on" times.

In some embodiments, the modulation/demodulation may be achieved by frequency division modulation (FDM). In FDM, each LED is modulated at a different frequency. This modulation can be with any waveform, and preferably by square wave modulation for best efficiency and simplicity of the driving circuit. This means that at any given time, one or more of the LEDs can be "on" at the same time, and one of more of the LEDs can be "off" at the same time. The detected signal is decomposed to the different LED contributions, for example by using matched filter or fast Fourier transform (FFT), as known to those skilled in the art.

FDM may be preferable with respect to TDM as FDM can provide lower peak current than TDM for the same average power, thus improving the efficiency of the LEDs. The higher efficiency allows for lower LED temperatures, which in turn provide better LED spectrum stability. Another advantage of FDM is that FDM has lower electromagnetic interference than TDM (since slower current slopes can be used), and smaller amplification channel bandwidth requirement than TDM.

In some embodiments, the modulation/demodulation may be achieved by amplitude modulation, each at a different frequency.

When the LED array uses a shared-electrodes architecture, a single LED can be turned "on" when the corresponding row and column are connected (e.g., anode to power and cathode to GND). However, when more than one row and one column is switched "on", all the LEDs sharing the connected rows and columns will be switched on. This can complicate the modulation/demodulation scheme. In order to resolve such a complication, TDM may be used, wherein a single row and a single column is enabled at each "on" time slot. Alternatively, combined TDM and FDM may be used, wherein a single row is selected with TDM, and FDM is applied on the columns (or vice versa). Alternatively, a 2-level FDM may be used, wherein each row and each column is modulated at different frequencies. The LEDs can be decoupled using matched filter or spectrum analysis, while taking special care to avoid overlapping harmonics of base frequencies.

Spectrometer System

In some embodiments, the spectrometer system described herein includes a digital processing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

In some embodiments, the spectrometer system disclosed herein includes one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

In some embodiments, the spectrometer system disclosed herein includes at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

In some embodiments, the spectrometer system disclosed herein includes software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the spectrometer system disclosed herein includes one or more databases, or use of the same. In view of the disclosure provided herein, those of skill in the art will recognize that many databases are suitable for storage and retrieval of information as described herein. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

Now referring to FIG. 2, the spectrometer system 100 typically comprises a spectrometer 102 as described herein and a hand held device 110 in wireless communication 116 with a cloud based server or storage system 118. The spectrometer system 100 can provide a system for analyzing a material in real time, to determine the identity and/or additional properties of the material. The obtained information regarding the material can then guide users in making decisions relating to the identified material. The spectrometer 102 may have a warm-up time of less than 5 seconds, in some embodiments less than 1 second, in order to support real-time material analysis. The spectrometer can then send the data to a hand held device 110, for example via communication circuitry 104 having a communication link such as Bluetooth™. The hand held device 110 can transmit the data to the cloud based storage system 118. The data can be processed and analyzed by the cloud based server 118, and transmitted back to the hand held device 110 to be displayed to the user. In many embodiments, the hand held device 110 provides a user interface (UI) for controlling the operation of the spectrometer 102 and/or viewing data as described in further detail herein.

The hand held device 110 may comprise one or more of a smartphone, tablet, or smartwatch, for example. In some embodiments, a single device having internet connectivity is configured to communicate with the spectrometer on the one hand and with the cloud based server on the other hand. In some embodiments, the spectrometer system 100 comprises two or more hand held devices, connected via Bluetooth communication and/or internet connection. Each of the two or more hand held devices may be configured to communicate with the other devices of the system either directly or through another hand held device of the system. For example, the system may comprise a mobile phone and a smartwatch, wherein the mobile phone is in communication with the spectrometer and the cloud based server as described. The smartwatch may be configured to communicate with the mobile phone via a wireless data connection such as Bluetooth, wherein the smartwatch can be configured to control the user interface of the mobile phone and/or display data received from the mobile phone. In some embodiments, the smartwatch may be configured to have internet connection, and may be used in place of the mobile phone to function as the data relay point between the spectrometer and the cloud based server, and to present the user interface to the user.

In many embodiments, one or more of the spectrometer, hand held device, and cloud based server of the system may comprise a computer system configured to regulate various aspects of data acquisition, transfer, analysis, storage, and/or display. The computer system typically comprises a central processing unit (also "processor" herein), a memory, and a communication interface (also "communication circuitry" herein). The processor can execute a sequence of machine-readable instructions, which can be embodied in a program or software. The instructions may be stored in a memory location. Each device of the spectrometer system may communicate with one or more of the other devices of the system via the communication interface.

Figure 16:
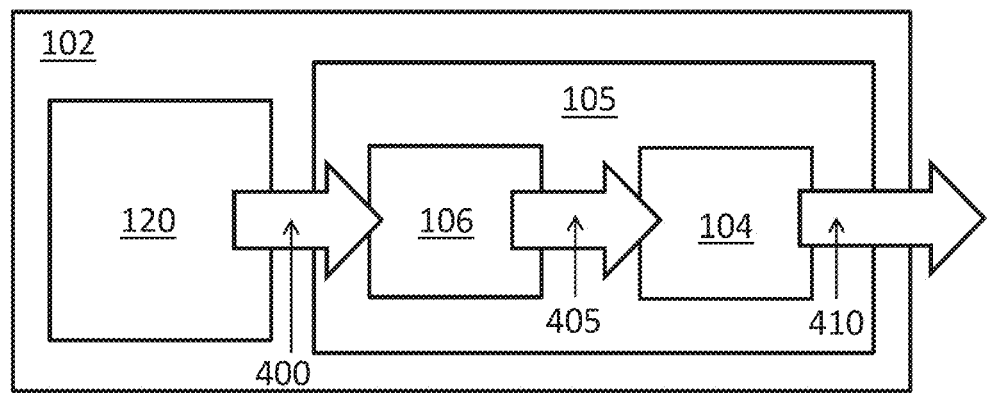
FIG. 16 shows a schematic diagram of the data flow in the spectrometer, in accordance with embodiments.

FIG. 16 shows a schematic diagram of the data flow in the spectrometer 102, in accordance with embodiments. The spectrometer head 120 is configured to acquire raw intensity data for a material when a user scans a material with the spectrometer 102. In addition to the raw spectral data, non-spectral data may also be obtained if the spectrometer 102 includes a sensor module such as a temperature sensor module described herein. The raw data 400 generated by the spectrometer head 120 may be transmitted to a processor 106 of the control board 105. The processor 106 may comprise a tangible medium comprising instructions of a computer program; for example, the processor may comprise a digital signal processing unit, which can be configured to compress the raw data. The compressed raw data signal 405 can then be transmitted to the communication circuitry 104, which may comprise a data encryption/transmission component such as Bluetooth™. Once encrypted, the compressed encrypted raw data signal 410 can be transmitted via Bluetooth to the hand held device 110.

Compression of raw data may be necessary since raw intensity data will generally be too large to transmit via Bluetooth in real time. The compression may be performed using a data compression algorithm tailored according to the physical properties of the optical system that create the spatial distribution of light onto the light detector of the spectrometer module. The data generated by the optical system described herein typically contains symmetries that allow significant compression of the raw data into much more compact data structures.

Figure 17:
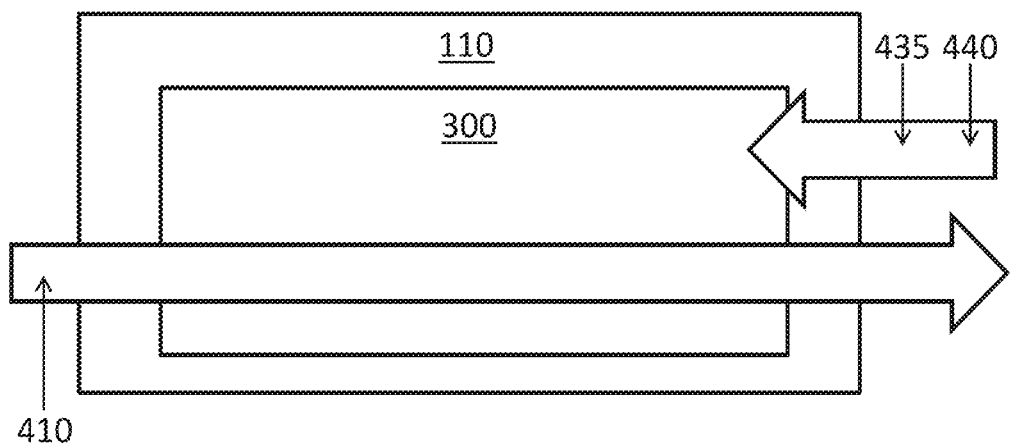
FIG. 17 shows a schematic diagram of the data flow in the hand held device, in accordance with embodiments.

FIG. 17 shows a schematic diagram of the data flow in the hand held device 110. The hand held device 110 can comprise a processor having a computer readable memory, the memory embodying instructions for presenting a user interface (UI) 300 for the spectrometer system via a display of the hand held device 110. For example, in embodiments comprising a mobile phone, a readable memory of the phone may comprise machine executable code in the form of a mobile application, providing instructions for presenting the UI. The hand held device 110 can also comprise a means for receiving user input to the UI, such as a touch-screen interface. The UI provides a space where users may interact with the spectrometer 102 and with the cloud server 118. For example, the UI can provide a user with the means for controlling the operation of the spectrometer 102, selecting analyses types to perform on the data generated from the sample scan, viewing the analyzed data from a sample scan, and/or viewing data from a database stored on the processor of the hand held device 110 or on the cloud server 118. In embodiments of the system comprising two or more hand held devices 110 in communication with one another, the spectrometer may be in communication with a first device, and the first device may be in communication with a second device comprising the display for the UI.

The encrypted, compressed raw data signal 410 from the spectrometer may be received by the UI 300 of the hand held device 110, wherein the UI is provided by a processor of the hand held device. The UI may then transmit the data 410 to the cloud server 118, for example via a wireless internet connection. Data may be transmitted automatically in real time or at certain intervals, or data may be transmitted when requested by a user. The UI can optionally add metadata 415 such as time, location, and user information to the raw data and transmit the data set. In some embodiments, a user may also provide instructions to the UI to perform one or more specific types of analysis; in this case, the UI may transmit, along with the compressed, encrypted raw data 410 and/or metadata 415, user instructions for performing the analysis.

Figure 18:
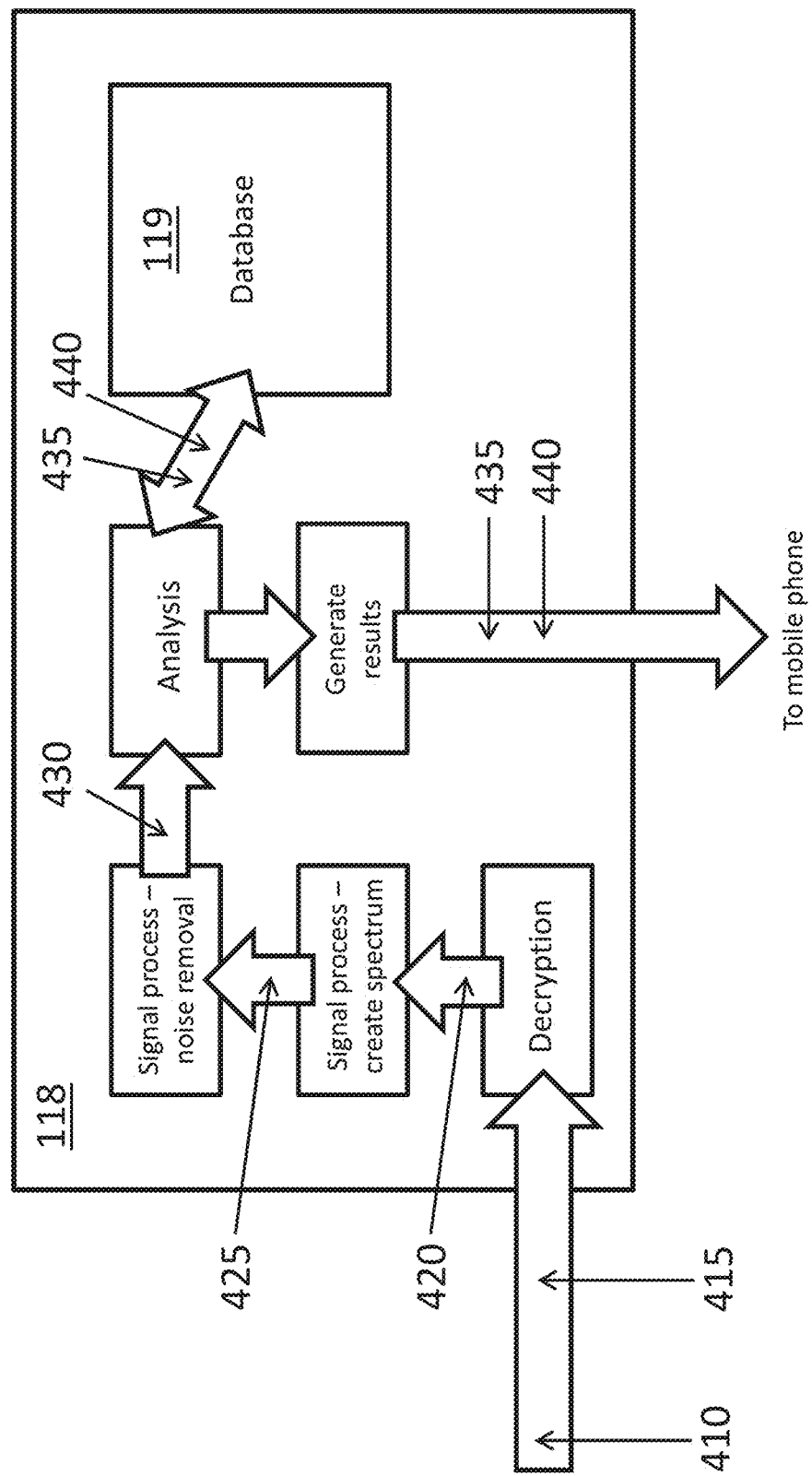
FIG. 18 shows a schematic diagram of the data flow in the cloud based storage system, in accordance with embodiments.

FIG. 18 shows a schematic diagram of the data flow in the cloud based storage system or server 118. The cloud server 118 can receive compressed, encrypted data 410 and/or metadata 415 from the hand held device 110. A processor or communication interface of the cloud server can then decrypt the data, and a digital signal processing unit of the cloud server can perform signal processing on the decrypted signal 420 to transform the signal into spectral data 425. The server may perform additional pre-processing of the spectrum, such as noise reduction, to produce pre-processed spectral data 430. Analysis of the pre-processed spectrum 430 can then be performed by a processor of the server having instructions stored thereon for performing various data analysis algorithms. The analyzed spectral data 435 and/or additional analysis results 440 (e.g., nutritional content of food, quality of gems, etc.) may be transmitted back from the server to the hand held device, so that the results may be displayed to the user via the display of the hand held device. In addition, the analyzed spectral data 435 and/or related additional analysis results 440 may be dynamically added to a universal database 119 operated by the cloud server, where spectral data associated with sample materials may be stored. The spectral data stored on the database 119 may comprise data generated by the one or more users of the spectrometer system 100, and/or pre-loaded spectral data of materials with known spectra. The cloud server may comprise a memory having the database 119 stored thereon.

The cloud based system or server 118 may be accessed remotely, for example via wireless internet connection, by one or more spectrometers and hand held devices of the spectrometer system. In many embodiments, the cloud server is simultaneously accessible by more than one users/hand held devices of the system. In some embodiments, hand held devices up to the order of millions can be simultaneously connected to the cloud server.

The multiple spectrometers 102 within a spectrometer system 100 may differ from one another, for example due to variations in manufacturing. Such differences among the multiple spectrometers may yield significant variations in the spectral data for the same material obtained by each spectrometer. In order to ensure that the data contributed to the universal database 119 by multiple users are comparable, the system may comprise a method for calibrating the data generated by each spectrometer, before adding the data to the universal database. For example, the specific optical response of each spectrometer may be characterized during manufacturing, by measuring how each spectrometer behaves in response to different kinds of inputs. The inputs may comprise a set of calibration patterns (spectra) that are measured with the spectrometer, and the corresponding spectrometer response function may be determined and output with the calibration data. This spectrometer-specific optical response data may be saved and stored as the calibration data for the specific spectrometer, typically in the cloud based server. The calibration data may be stored tagged with an identifier for the specific spectrometer, such that when the server receives raw data from the spectrometer, the server can identify and locate the appropriate calibration data for the specific spectrometer. The server may then apply the spectrometer-specific calibration data in producing the spectral data from the raw data received from the spectrometer. Such a calibration process can compensate for device-to-device variation, providing a way for multiple users of the system to make meaningful comparisons among data for the same material obtained using different spectrometers.

In many embodiments, the cloud based server 118 provides users of the spectrometer system 100 with a way of sharing the information obtained in a particular measurement. Database 119 located in the cloud server can constantly receive the results of measurements made by individual users and update itself in real time or at regular intervals. The updating of the database 119 based on user contribution can rapidly expand the number of substances for which a spectral signature is available. Thus, each measurement made by a user can contribute towards increasing the accuracy and reliability of future measurements made by any user of the spectrometer system.

The sharing of information among multiple users of the spectrometer system through the cloud based server can provide a useful tool for making informed decisions regarding materials of interest. For example, a user shopping for apples may be interested in finding out what stores may carry the sweetest apples. The spectrometer system may provide the user with a means for viewing a map of matter for apples, the map of matter presenting a comprehensive compilation of user-contributed, analyzed spectral and non-spectral data for specific materials, as described in further detail herein. The map of matter may be visualized based on geographical location, providing users with the ability to view what stores in the area carry relatively sweet apples. The map of matter may also be visualized based on time/date, such that users may view the data for apples for different time windows (e.g., within the last hour/day/week/month, on a certain date or over a certain date range, etc.). Alternatively or in combination, the map of matter may also provide visualization of material data based on store/branch, type of object, temperature, number of measurements, and many other factors. For example, the system may provide users with a location-based map displaying all data for apples in the universal database, and users may be click on a particular location/store to view the data summary for the selected store. The store-specific data summary may also be viewed on a timeline, allowing users to determine the trend in the sweetness of apples carried by the store over time. The spectrometer system may thus be used to make a more informed purchasing decision.

The spectrum of a sample material can be analyzed using any appropriate analysis method. The processor of the cloud server 119, hand held device 110, or spectrometer 102 may comprise one or more algorithms for spectrum analysis. Non-limiting examples of spectral analysis techniques that can be used include Principal Components Analysis, Partial Least Squares analysis, and the use of a neural network algorithm to determine the spectral components.

In embodiments in which a Raman spectrum is obtained, the Raman signal can be separated from any fluorescence signal. Both Raman and fluorescence spectra can be compared to existing calibration spectra. After a calibration is performed, the spectra can be analyzed using any appropriate algorithm for spectral decomposition; non-limiting examples of such algorithms include Principal Components Analysis, Partial Least-Squares analysis, and spectral analysis using a neural network algorithm. This analysis provides the information needed to characterize the sample that was tested using the spectrometer. The results of the analysis can then be presented to the user.

In some embodiments the analysis is not contemporaneous. In some embodiments the analysis is in real time.

In some embodiments, the spectrometer system may perform analysis of the raw data locally. The spectrometer system may comprise a memory with a database of spectral data stored therein, and a processor with analysis software programmed with instructions. The memory can be volatile or non-volatile in order to store the user's own measurements in the memory. Alternatively, the database of spectral data can be provided with a computer located near the spectrometer, for example in the same room. Alternatively or in combination, the spectrometer may partially analyze the raw data prior to transmission to a remote server, such as the cloud server 118 described herein, wherein heavier calculations for more complicated analyses may be performed.

An analyzed spectrum can determine whether a complex mixture being investigated contains a spectrum associated with components. The components can, for example, be a substance, mixture of substances, or microorganisms. The intensity of these components in the spectrum can be used to determine whether a component is at a certain concentration, and whether the concentration of an undesirable component is high enough to be of concern. Non-limiting examples of such substances include toxins, decomposition products, or harmful microorganisms. In some embodiments of the invention, if it is deemed likely that the sample is not fit for consumption, the user is provided with a warning. Various possible applications of the compact spectrometer system are described in further detail herein.

User Interface

The spectrometer system 100 is typically provided with a user interface (UI) that provides a means for users to interact with the spectrometer system. The UI is typically provided on a display of the hand held device 110 of the spectrometer system, the hand held device comprising a processor that comprises instructions for providing the UI to the display, for example in the form of a mobile application. The display can be provided on a screen. The screen may comprise a liquid crystal display (LCD) screen, an LED screen, and/or a touch screen. The UI is typically presented to the user via a display of the hand held device 110, and is configured to receive input from the user via an input method provided by the hand held device 110.

Figure 19:
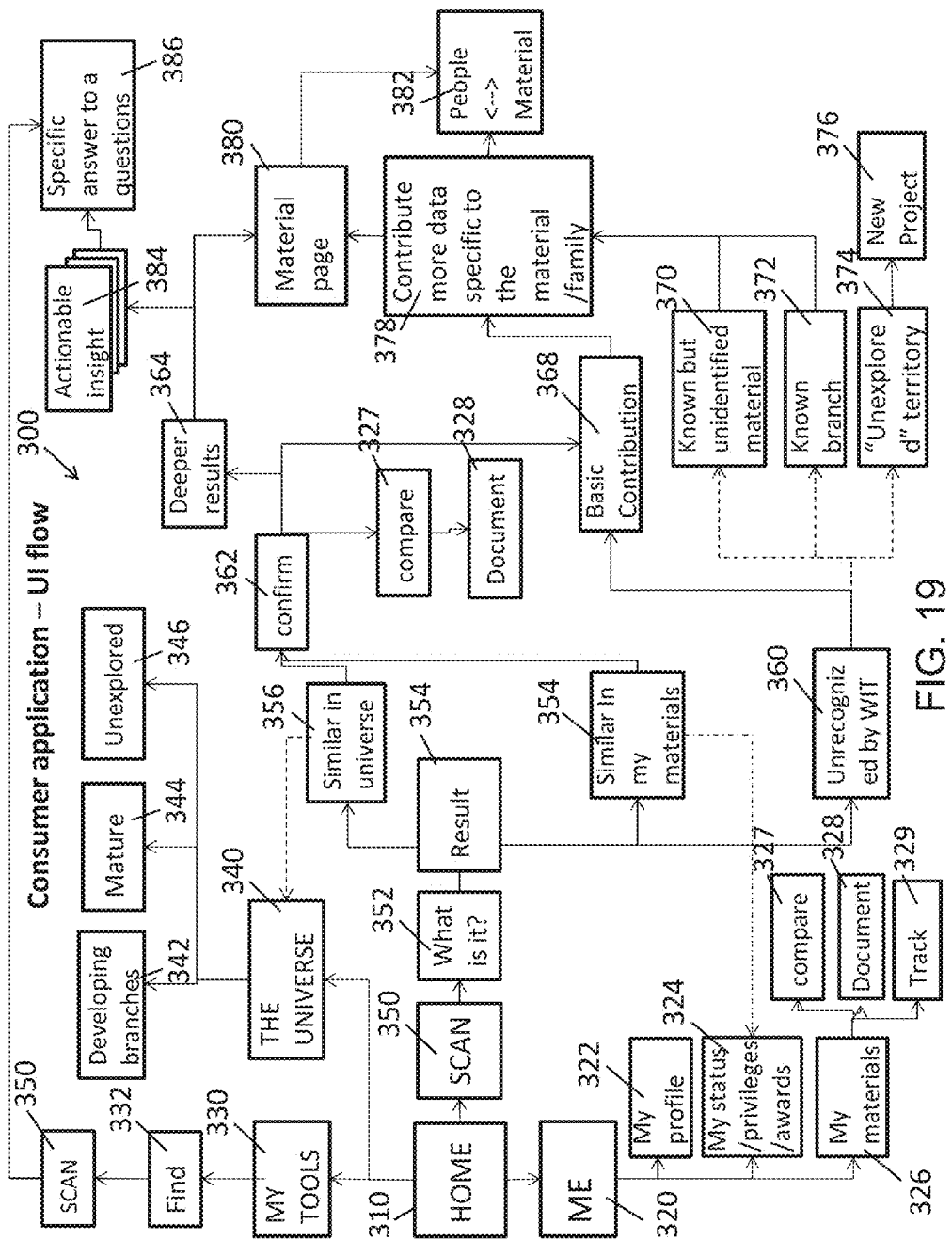
FIG. 19 shows a schematic diagram of the flow of the user interface (UI), in accordance with embodiments.
Figure 20:
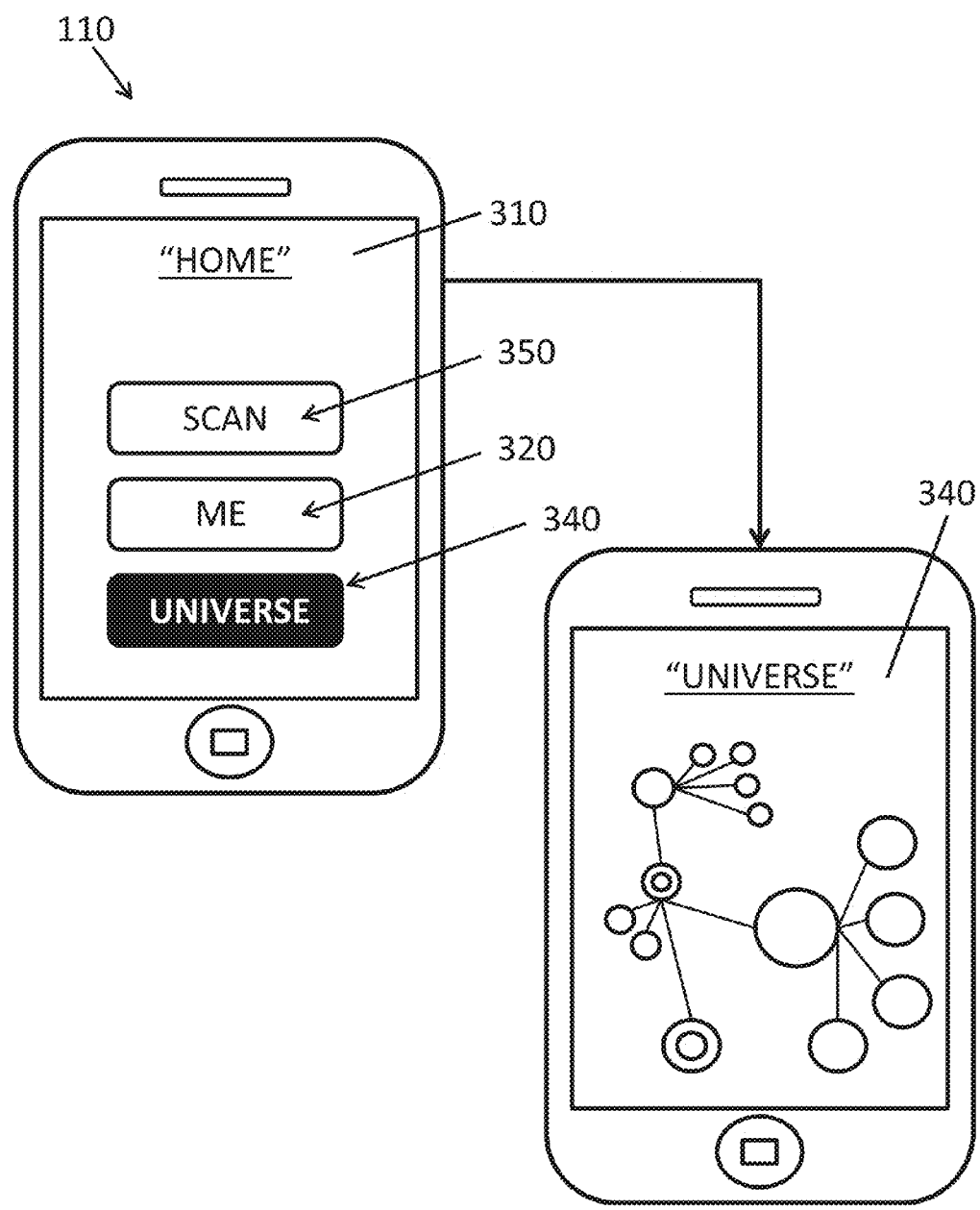
FIG. 20 illustrates an example of how a user may navigate through different components of the UI of FIG. 19.

FIG. 19 shows a schematic diagram of the flow of the user interface (UI) 300. The UI typically comprises a plurality of components as shown in FIG. 19, wherein each UI component may comprise a step of a method for the processor of the hand held device to provide the computer interface. The user may navigate through each component of the UI, wherein each component may have one or more corresponding screens configured to display user-selectable options, take user inputs, and/or display outputs of user-initiated actions (e.g., analyzed data, search results, actionable insights, etc.). A user-selectable option within a UI component may include an analysis identifier, such as an image or text, or an icon associated with a spectroscopic analysis application. When a user selects a user-selectable option within a UI component, for example, by touching the icon for a particular option, the processor providing the UI may carry out a set of instructions associated with the user-selected option. As a result, the UI may be directed to a new screen associated with a component of the UI related to the user-selected option. FIG. 20 illustrates an example of how a user may navigate through different components of a UI. In this example, the user begins from the screen of the UI associated with the component "Home" 310, described in further detail herein, as shown on the left. From "Home" 310, the user selects the option "Universe", which is associated with the component "Universe" 340 of the UI. As a result, the UI directs the user to the screen associated with the "Universe" 340 component, as shown on the right.

A person of ordinary skill in the art will recognize variations and adaptations that may be made to the UI flow as shown in FIG. 19, including, but not limited to, the removal or addition of one or more components, one or more components arranged in a different order, and/or one or more components comprising subcomponents of other components. One or more of the processors as described herein may comprise a tangible medium embodying instructions to provide one or more of the components of the user interface or to implement the method of the computer interface, and combinations thereof.

Figure 21A:
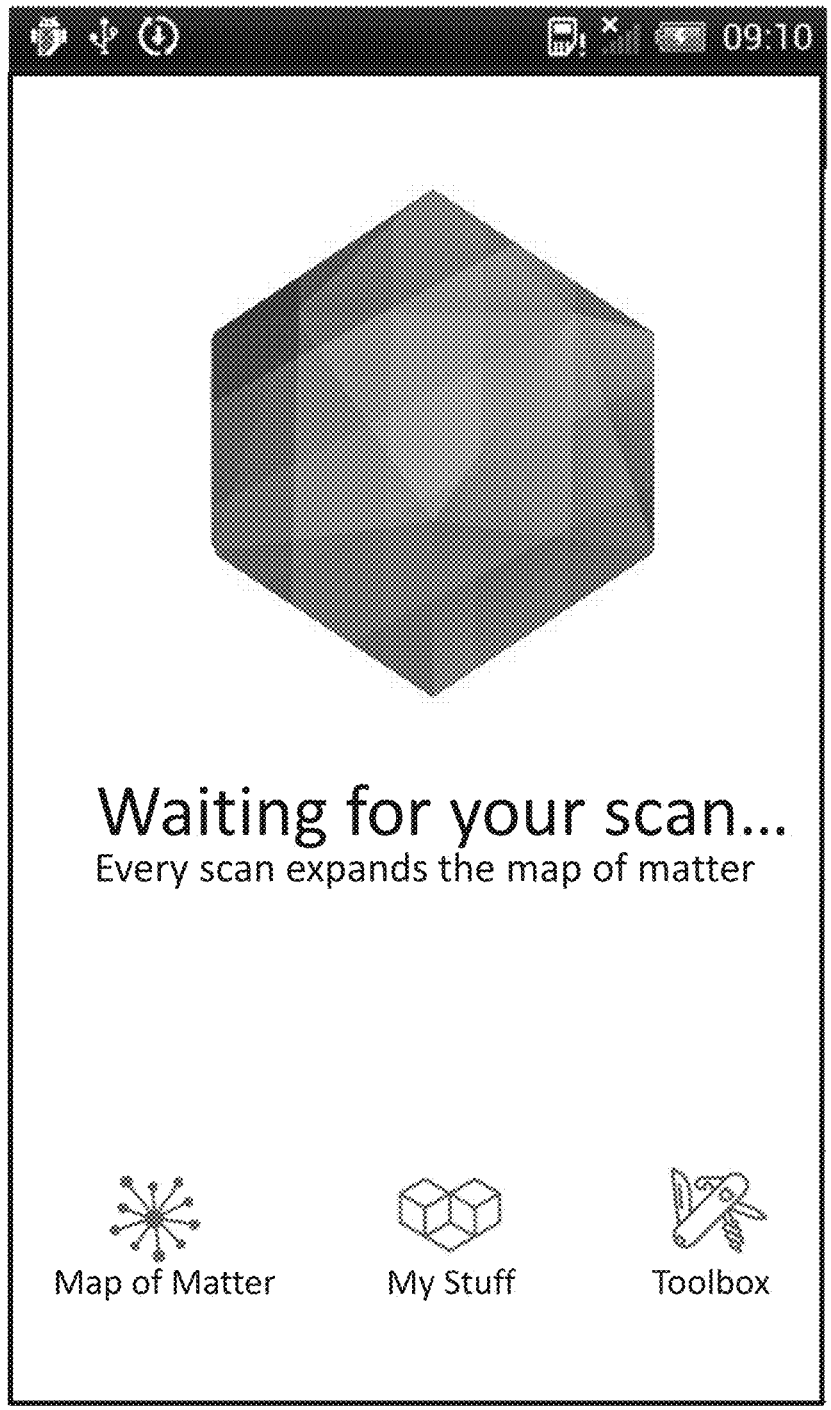
FIG. 21A shows an exemplary mobile application UI screen corresponding to a component of the UI of FIG. 19.

Typically, when a user opens the application providing the UI, the user is directed to the component "Home" 310. In the "Home" 310 component, the main action presented to the user may be an invitation to scan a sample material, via the "Scan" 350 component. FIG. 21A shows an exemplary mobile application UI screen corresponding to the "Home" 310 component of the UI. "Home" 310 is also the entry point to the components "Me" 320, "My Tools" 330, and "Universe" 340. "Me" 320 provides access to private user information. "My Tools" 330 provides access to personalized tools for scanning and analyzing materials. "Universe" 340 provides access to information in the universal database 119 operated by the cloud server 118 as described herein.

"Me" 320 may provide access to one or more of "My profile" 322, "My status/privileges/awards" 324, and "My materials" 326. "My profile" 322 may store a user's personal information, such as name and location, for example. "My profile" 322 can also store a user's personal settings for certain aspects of the system, such as privacy preferences, for example. "My status/privileges/awards" 324 may track a user's history of performing scans using the spectrometer system and contributing data to the universal database 119, for example. Based on the user's contribution to the universal database, the user may be given certain privileges, credits, or recognition, thereby providing an incentive for users to actively contribute data to the universal database. For example, "contribution scores" may be kept by the system for each user, and displayed under "My status/privileges/awards". Users may also be provided with a way of interacting with other users of the spectrometer system, either through "My status/privileges/awards" 324 or through a separate module. For example, users may be provided with a way of recommending/liking other users based on their contribution status, and such feedback from other users may be accessed via "My status/privileges/awards" 324 or another appropriate component. "My materials" 326 can allow users to view and compare data associated with their materials via the "Compare" 327 component. The scans performed by a user may be stored in "My materials" under a tag, and kept private or public (accessible by other users via the universal database 119) depending on user preference. "Compare" 327 can provide users with the ability to compare scans by tags, either across different tags or within a given tag. "My materials" 326 can also provide users with the ability to document their projects via the "Document 328" component, for example by adding notes or image data associated with a material. "My materials" 326 can also provide users with the ability to track their projects via the "Track" 329 component, wherein, for example, the UI may display a complete, sortable and/or searchable list of projects for the user. Scan data that users choose to store in the public domain may be accessed by other users of the system, and "Track" 329 may also provide a way for a user to track other users' projects.

"My tools" 330 can provide quick access to personalized tools for scanning and analyzing materials that may be initiated directly without going through the "Scan" 350 component. A user may directly build and save a specific analysis (e.g., if the user is interested in using the spectrometer to determine the percent fat in cheese, he/she may set up such an analysis by identifying the material and the parameter of interest for the analysis). Alternatively or in combination, once a user has used the spectrometer to perform scans, the user may be given the option of storing favorite tools/analyses. Alternatively or in combination, the system may automatically store frequently used tools/analyses for access under "My tools". "Find" 332 can provide users with a way of searching for a desired analysis tool among stored tools. "My tools" may also be configured to notify users about new tools that are made available by the system. Once a user selects a desired analysis method from the component "Find" 332, the user may be invited to initiate a scan through the UI component "Scan" 350, described in further detail herein. However, since the analysis method has already been selected, "Scan" 350 may be configured to skip over some intermediate steps (e.g., identification of the material), and proceed directly to displaying the answer to the user's query through the component "Specific answer to a question" 386.

"Universe" 340 can give users access to the universal database 119 operated by the cloud server 118, wherein spectral signatures of materials are stored for comparison against and analysis of scanned data. "Universe" 340 may be displayed as a graphical map, providing users with a generic visualization of the map of matter by different attributes. For example, the map may be organized by geographic, material, gender, maturity, or "popularity" attributes. A user may be able to zoom in and out of the map to get to a specific material page. The map of matter for a specific material may be visualized based on one or more of a geographical location, time/date, store/branch, type of object, temperature, number of measurements, and many other factors. Different types of materials in the map may develop at different paces, resulting in different "maturity" levels over time; accordingly, the visualization of the branches of the map may differ based on this maturity level. "Universe" 340 can thus provide users with a way to viewing the map through three separate UI components, "Developing branches" 342, "Mature" 344, and "Unexplored" 346, which may display different types of information, display the map using different visualizations, and/or present different user-selectable options. The map of matter may highlight a user's own contributions to the map in the display, so that the user may be able to visualize his/her scans in the context of the map. Users may be given the ability to search for material "soul mates" (e.g., materials having similar spectral signatures), or track down "experts" in a certain material branch by identifying users who have made significant contributions to a branch of interest. "Universe" 340 may also provide users with notifications regarding materials that the user is interested in, such as new contributions/map progress made on certain materials. Users may be given a way to set up "campaigns" to foster maturity of a certain branch in the map of matter, and the "Universe" may also send users notifications regarding such campaigns.

An exemplary workflow for scanning a material with the spectrometer system is now described with reference to FIG. 19. A user may initiate a scan from the screen corresponding to the UI component "Home" 310, such as the one shown in FIG. 21A, by pressing a button on the spectrometer or on the mobile application presenting the UI. When a scan is initiated, the UI directs the user to the screen corresponding to the component "Scan" 350, which may instruct the spectrometer to begin a measurement, compress and encrypt the raw data, and/or transmit the compressed and encrypted data to the UI of the hand held device.

When data is received by the UI, the UI may initiate the "What is it?" (WIT) 352 component, which may comprise the system's main classification algorithm. The main classification algorithm may, for example, attempt to determine the material's identity based on the spectrum of the material, by comparing the spectrum against the spectra of known materials stored in the user's personal database stored under the "My Materials" component and/or the universal database 119. The algorithm may yield three different results: the identification of similar spectra in the "Universe" database, the identification of similar spectra in the "My Materials" database, or a failure to find any matching spectra in either database. The outcome of the algorithm run by the "What is it?" 352 component may be presented to the user via the "Result" 354 component, wherein the user may view the preliminary identification results and provided with a range of selectable options for further actions, as described herein for each possible outcome.

If one or more similar materials are identified in the "Universe" database, the user may be directed to the screen corresponding to the UI component "Similar in universe" 356. From here, the user may be given the option to view the data relevant to the material in the universal database 119, directing the user to the UI component "Universe" 340. Alternatively, the user may be asked to confirm that the material indeed matches the identified material(s), through the UI component "Confirm" 362. If the system has found a plurality of materials with spectra similar to the sample, the user may be asked to select one or more of these "matching" materials for further analysis.

If one or more similar materials are identified in the "My materials" database, the user may be directed to the "Similar in My Materials" 355 component of the UI. From here, the user may choose to navigate to the "My status/privileges/awards" 324 component or the "My materials" 326 component, where the user may view and compare data associated with their materials. Alternatively, the user may be asked to confirm that the material indeed matches the identified material(s), through the UI component "Confirm" 362.

Figure 21B:
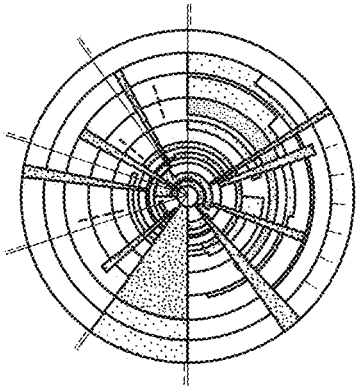
FIGS. 21B and 21C show an exemplary mobile application UI screen corresponding to components of the UI of FIG. 19.

If the identity of the measured material is positively confirmed by the user, the system may initiate the "Compare" 327 component to allow users to view and compare data associated with their material. The user may also document the results of the scan through the "Document" 328 component of the UI, which provide users with the option of adding notes or other miscellaneous data relating to the measurement. For example, as shown in FIG. 21B, an image of the measured material may be added, wherein the image may be acquired by an image capture device integrated with, or separate from but in communication with, the spectrometer system. The UI may also present users with the option of running further analyses of the material, through the UI component "Deeper results" 364. Further analyses may include, for example, analyses of specific nutritional attributes of a food item (e.g., percentage of fat/carbohydrates/protein, number of calories), specific contribution of a pharmaceutical product, or attributes of a plant (e.g., water content). The user may be given the option of selecting one or more types of analysis, for example by searching through a list of available analyses for the confirmed material. Alternatively or in combination, the system may automatically select one or more appropriate analysis tools, based on the identity of the material. For example, the system may further comprise an image capture device such as a camera, and may be configured to receive image data acquired by the image capture device, to use at least a portion of the image data in automatically selecting the appropriate analysis tools. In order to aid in the automatic selection of the analysis tool, a processing device of the spectrometer system may be configured to recognize a characteristic of the material based on the image data. In embodiments where two or more different types of analyses are selected, the selection of the analysis types may be based on a predetermined hierarchy.

Figure 21C:
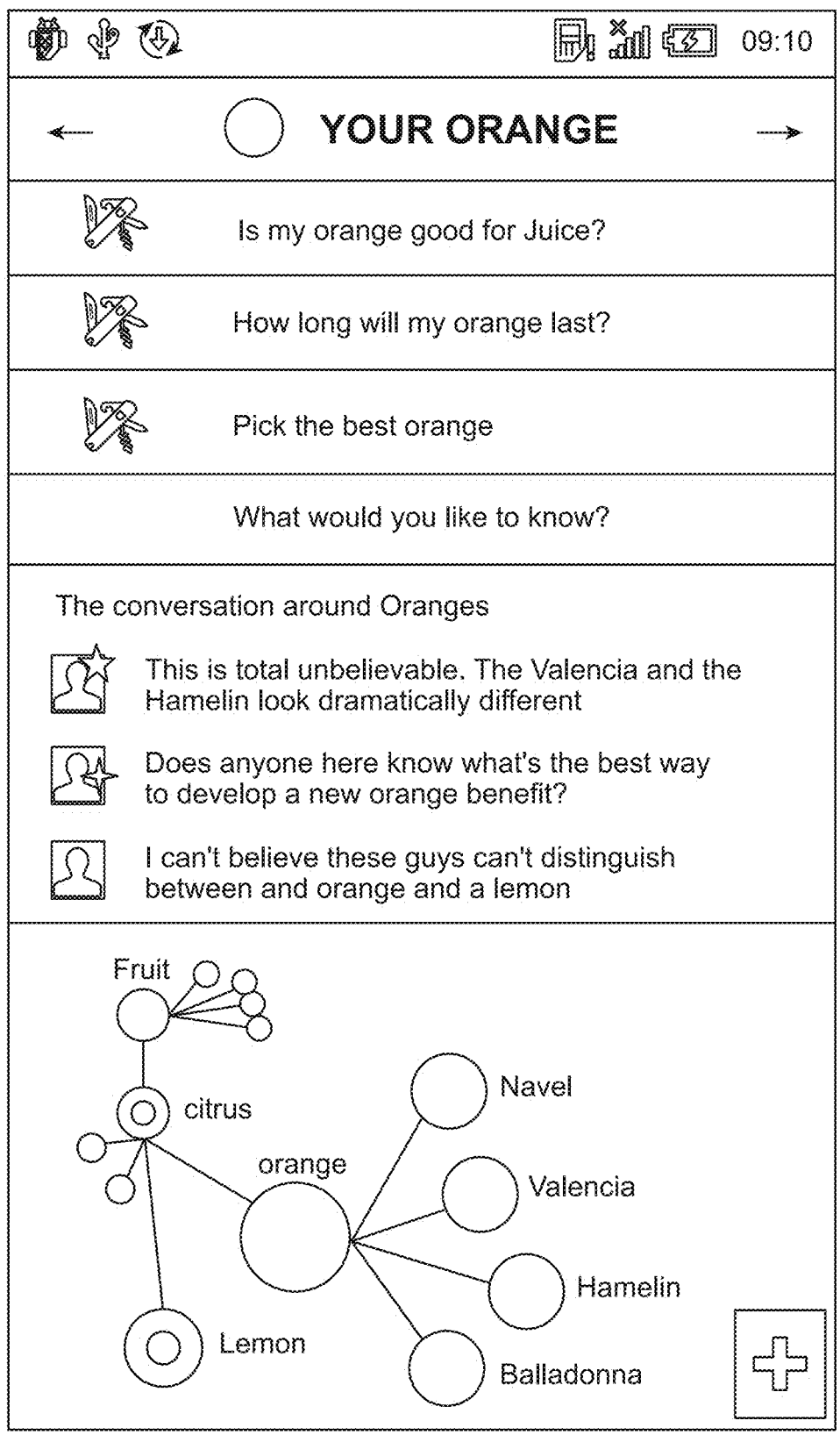

Once further analyses are completed, the UI can display the data for the measured material through the "Material page" 380 component of the UI. The UI may optionally provide the user with actionable insight via the "Actionable insight" 384 component. FIGS. 21B and 21C show an exemplary mobile application UI screen corresponding to the "Material page" 380 and "Actionable insight" 384 components of the UI (FIG. 21C shows the screen of FIG. 21B scrolled down). As shown in FIG. 21B, the UI may display results of the analysis, such as the identity and nutritional content analysis of the material; some additional parameters that may be displayed in the results include an image of a material, a freshness of a material, and a textual description of a material. In many embodiments, a visual representation of the spectral data is also displayed to the user. In many embodiments, the display of results also includes a visualization of the map of matter of the component "Universe" 340. The UI may also provide the users with a way of connecting with other users interested in the measured material, through the "People<-->Material" 382 component. For example, the component may enable users to participate in social messaging as shown in FIG. 21C, fostering conversations among system users related to the identified material.

The "Actionable insight" 384 component may provide users with the option of selecting one or more specific questions related to the measured material, such as those shown in FIG. 21C, whose answer may provide an insight that can be used as basis for taking a certain course of action. For example, if the identified material is an apple with a relatively high sugar content, the UI may inform the user that the user should select/consume the apple if the user desires a sweet fruit, or, conversely, that the user should not select/consume the apple if the user has a condition, such as diabetes, that would make the high sugar content an attribute that should be avoided. The UI may, optionally, have the ability to store personal data such as certain conditions and/or preferences, such that the UI may automatically select and display the most appropriate actionable insight for the specific user. The answer or actionable insight may be provided to the user via the "Specific answer to a question" 386 component. The component 386 may also be directly accessible via the "My Tools" 330 component, wherein a specific analysis method may be chosen prior to initiating a scan, and the user can directly obtain an answer or actionable insight to a specific question regarding a specific material.

Sometimes, the component "Confirm" 362 may not yield a positive confirmation by the user. If the identity of the measured material does not actually match the material(s) that the system has found to be a "match", the user may be prompted to provide basic information regarding the measured material, through the component "Basic contribution" 368. Once the basic identity of the material has been provided, users may optionally be asked to contribute additional data, through the component "Contribute more data specific to the material/family" 378. Users may, for example, contribute metadata such as physical properties of the material, or image data. From here, users may be directed to "Material page" 380 where they may view information regarding the material of interest, and/or users may participate in social conversations/interactions with other users of the system via the component "People<-->Material" 382.

When a user generates spectral data through the "Scan" 350 component or contributes non-spectral data through the "Basic contribution" 368 and/or "Contribute more data" 378 components, the data may be added to the universal database 119. Data may be automatically added to the universal database 119, while giving the user the option to keep the contribution "private" (not accessible by other users of the system). Any data generated or contributed by a specific user may also be added to the user's personal database of materials stored in the "My Materials" component. Data in a user's personal database may be configured to be kept private or to be shared with other users of the system. Alternatively, some of the data in the personal database may be kept private, while some may be shared with other users.

In order to maintain the integrity and validity of the data contained in the universal database, a system check may be implemented before the database is updated with the data from a scan. The system check may be initiated, for example, at the "Document" 328 component (where newly generated spectral data is added to the database), or at the "Basic Contribution" 368/"Contribute more data" 378 component (where user-contributed non-spectral data is added to the database). The system check may, for example, comprise an outlier detection algorithm, wherein data for the relevant material family is sorted, and the new data point is compared against the existing data to verify the validity of the new data point (e.g., whether the new data point falls within a specified standard deviation from the average of the existing data points). Any data point identified as an "outlier" may be held back from being added to the database, and/or "quarantined" in a location separate from the universal database. An "outlier" may comprise, for example, a data point for a known material that differs significantly from the mean data for the material, or any data point for a previously unrecognized material/spectrum. A quarantined "outlier" data point may eventually be added to the universal database, as data points previously recognized as outliers may become recognized as valid as the size and breadth of the universal database grows over time. The system check for verifying the validity of new data may also be based on one or more conditions associated with collection of the acquired light spectrum, including at least one of a temperature, a geographic location, a category of a material, a type of a material, a chemical composition, a time, an appearance of a material, a color of a material, a taste of a material, a smell of a material, and an observable characteristic associated with a material.

After performing a scan through the "Scan" 350 component, the system may fail to find a match for the measured material's spectrum, in either the "Universe" database or the "My materials" database. In this case, the "Unrecognized by WIT" 360 component of the UI may be initiated. The user may be directed to the "Basic contribution" 368 component of the UI, described in further detail herein, where the user may be asked to contribute basic identity information (if known) regarding the sampled material. If the sampled material is a known material with a previously unidentified spectrum, the UI may initiate the "Known but unidentified material" 370 component, wherein the user may be asked to contribute additional data relating to the material via the "Contribute more data" 378 component. If the sampled material is a known material belonging to a known branch of the map of matter, the UI may initiate the "Known branch" 372 component, wherein the user may be asked to contribute additional data relating to the material via the "Contribute more data" 378 component. If the sampled material is a completely unknown material that doesn't appear to belong to any known branches comprising classes of classifications of the map of matter, the UI may initiate the "Unexplored territory" 374 component. The "Unexplored territory" 374 component may direct the UI to run the "New project" 376 component, which can create a new, exploratory branch in the map of matter (e.g., under the "Unexplored" 346 component of the "Universe" 340). The "Unexplored territory" 374 component may prompt the user to contribute as much information as possible regarding the material, including images and/or textual descriptions of the material.

The UI may further be configured to track user preferences and provide recommendations based on acquired light spectra. For example, a user may scan a product to obtain a light spectrum, and based on the spectrum and/or pre-stored user preference data, the system may send the user a recommendation about the scanned product. The universal database may be configured to store spectroscopic data and associated preference data for each system user, and a processing device of the system may be configured to receive a recommendation request from a device associated with a user, and generate and provide a recommendation based on the analyzed data. The processing device of the system can be configured to receive and process update requests for user preference settings. For example, a user may set his/her preferences regarding product tracking and recommendation functions through the "Me" component of the UI.

The UI may further provide means for supporting applications development by users, in order to encourage user involvement in developing and improving the system databases, algorithms, and/or user interface.

The UI may provide support for chemometric applications development, for example, for users/developers who are interested in developing new models, analysis algorithms, and/or databases of the materials they want to support in their applications. Developers may first collect relevant samples and measure them using the spectrometer system disclosed herein. Developers may then create a model or algorithm using a set of algorithms provided by the spectrometer system's infrastructure. Developers can test their model and see how well it functions, and then correct it to get optimal results. Once the model development is completed, developers can "publish" their model on the spectrometer system's infrastructure and allow other users to use the model. Users may use the model as part of the spectrometer system's mobile application, or developers may also develop their own mobile application that can run the developed model. If developers choose to develop their own mobile application, the newly created mobile application may communicate with the spectrometer system's infrastructure to run the model.

The UI may also provide support for mobile applications development, for users/developers who are interested in using the existing database structure and analysis algorithms to build new mobile applications. Developers may take advantage of existing chemometric applications and/or models to create a new user interface and a new user experience, possibly with new related content. Developers may "publish" their new mobile application on the spectrometer system's infrastructure, allowing others to access and use their mobile app.

The UI may also provide an option for researchers ("Researcher Mode"), where researchers are provided with the ability to generate their own database, then download the raw data of the database for their own use, outside of the spectrometer system's infrastructure. Such an option can provide researchers with maximum flexibility in handling data.

FIGS. 22A-22F show a method 500 for the processor of a hand held device to provide the user interface 300 for the spectrometer system, as described herein.

Figure 22A:
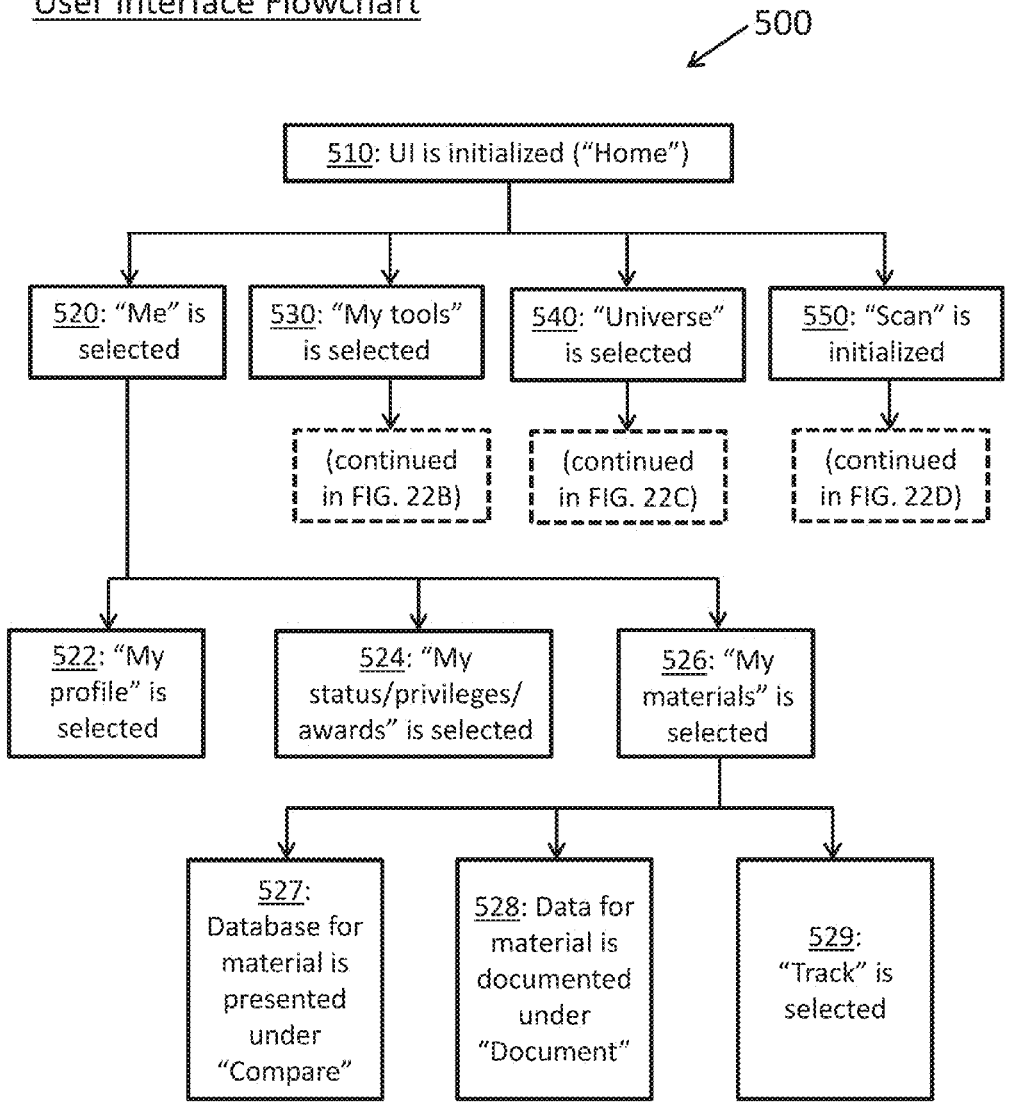
FIGS. 22A-22F show a method for a processor of a hand held device to provide the user interface of FIG. 19, in accordance with embodiments.

Referring to FIG. 22A, at step 510, the UI is initialized, for example by a user starting a mobile application providing the UI, and the "Home" 310 component is presented to the user as described herein. The "Home" 310 component may present the user with the options of selecting one of "Me", "My Tools", "Universe", or "Scan".

At step 520, "Me" is selected from step 510, and the user is directed to the "Me" 320 component of the UI, as described herein. "Me" 320 may provide access to one or more of "My profile" 322, "My status/privileges/awards" 324, and "My materials" 326. At step 522, the "My profile" 322 component is executed, as described herein. At step 524, the "My status/privileges/awards" component 324 is executed, as described herein. At step 526, the "My materials" 326 component is executed, as described herein. "My materials" 326 may provide access to one or more of "Compare" 327, "Document" 328, or "Track" 329. At step 527, the "Compare" 327 component of the UI is executed, as described herein. At step 528, the "Document" 328 component of the UI is executed, as described herein. At step 529, the "Track" 329 component of the UI is executed, as described herein.

Figure 22B:
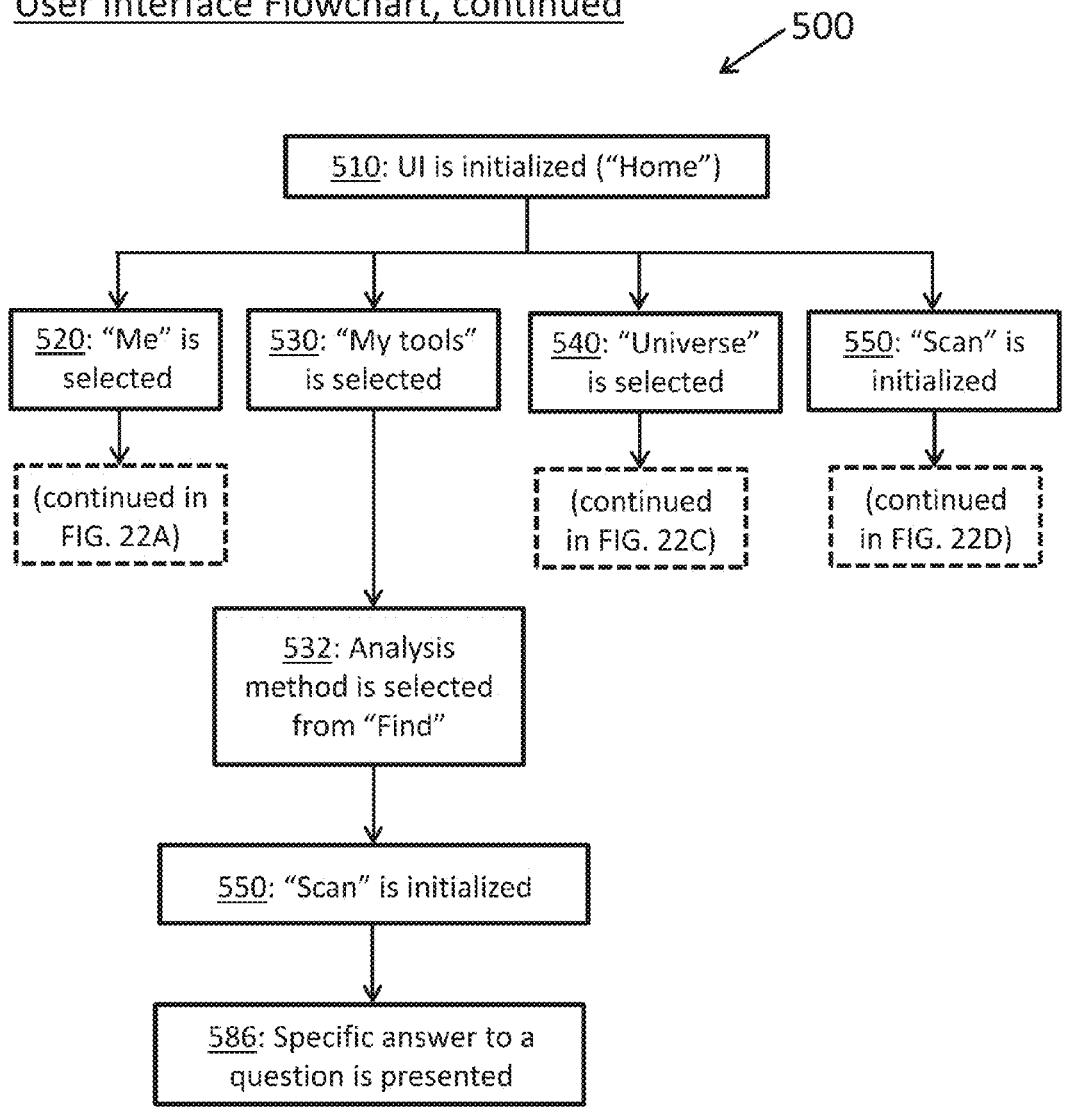

Now referring to FIG. 22B, at step 530, "My Tools" is selected from step 510, and the user is directed to the "My tools" 530 component of the UI, as described herein. At step 532, an analysis method is selected by the user from the UI component "Find" 332, as described herein. At step 550, the "Scan" 350 component of the UI is executed, as described herein, using the analysis method selected at step 532. At step 586, the "Specific answer to a question" 386 component of the UI is executed as described herein, wherein the user is presented with an actionable insight.

Figure 22C:
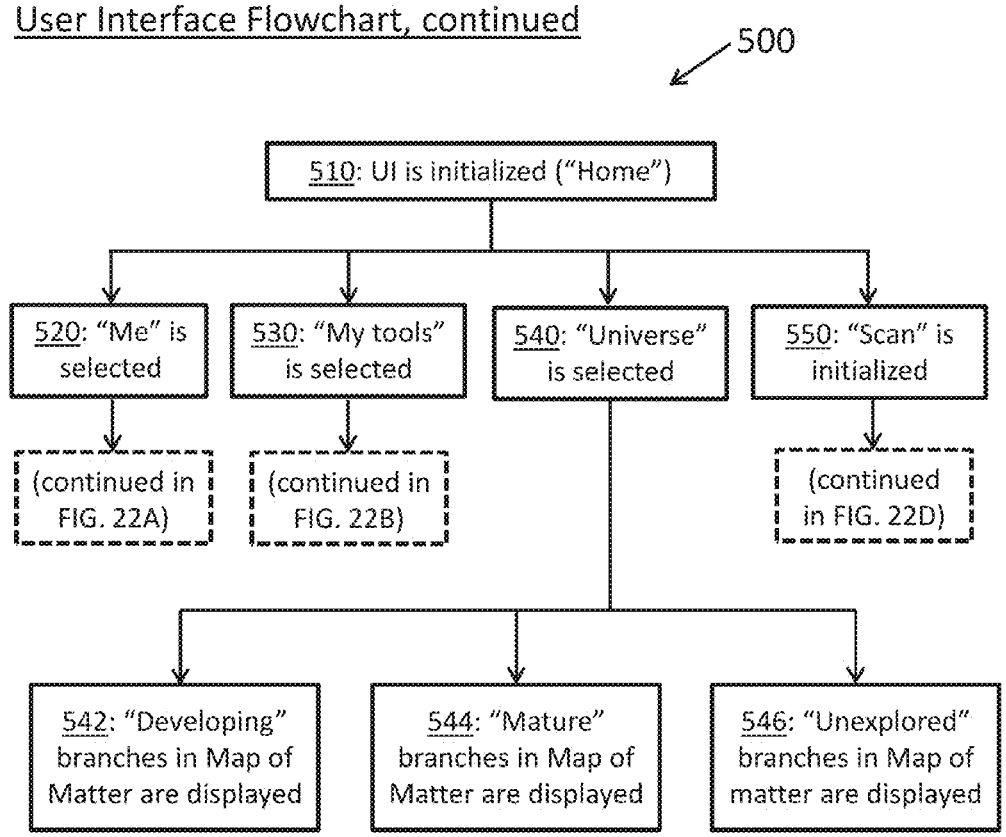

Now referring to FIG. 22C, at step 540, "Universe" is selected from step 510, and the user is directed to the "Universe" 340 component of the UI, as described herein. At step 542, the "Developing branches" 342 component is executed, as described herein. At step 544, the "Mature branches" 344 component is executed, as described herein. At step 546, the "Unexplored branches" 346 component is executed, as described herein.

Figure 22D:
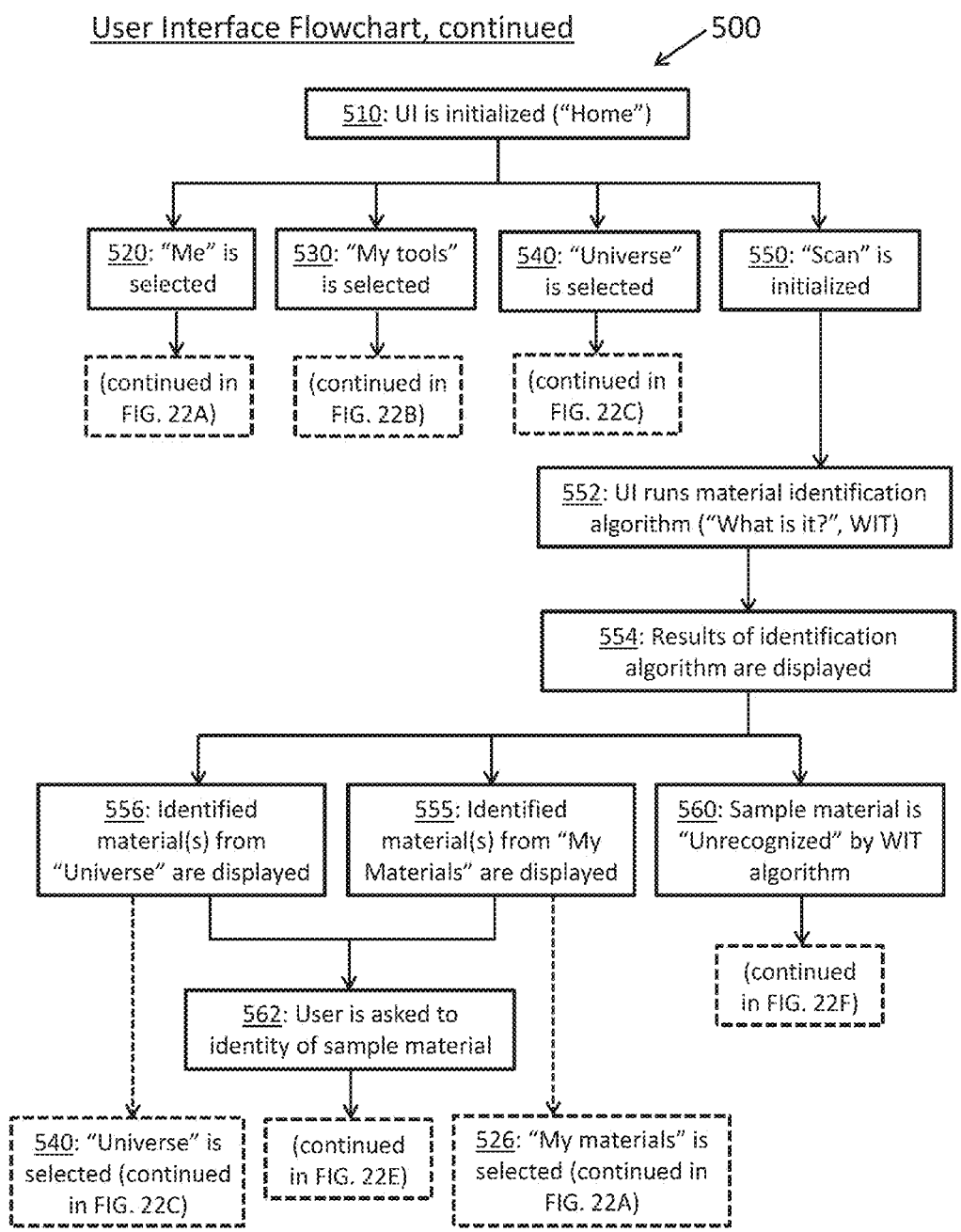

Now referring to FIG. 22D, at step 550, "Scan" is selected from step 510, and the user is directed to the "Scan" 350 component of the UI, as described herein. At step 552, the "What is it?" 352 component is executed, as described herein. At step 554, the "Result" 354 component is executed, as described herein. "Result" 354 may provide access to one or more of "Similar in universe" 356, "Similar in my materials" 355, or "Unrecognized by WIT" 360. At step 556, the "Similar in universe" 356 component is executed, as described herein, wherein the user may be provided with the option of selecting between "Universe" 340 and "Confirm" 362. At step 555, the "Similar in my materials" 355 component may be executed, as described herein. At step 555, the user may be provided with the option of selecting between "My materials" 326 or "Confirm" 362. At step 560, the "Unrecognized by WIT" 360 component of the UI is executed, as described herein.

Figure 22E:
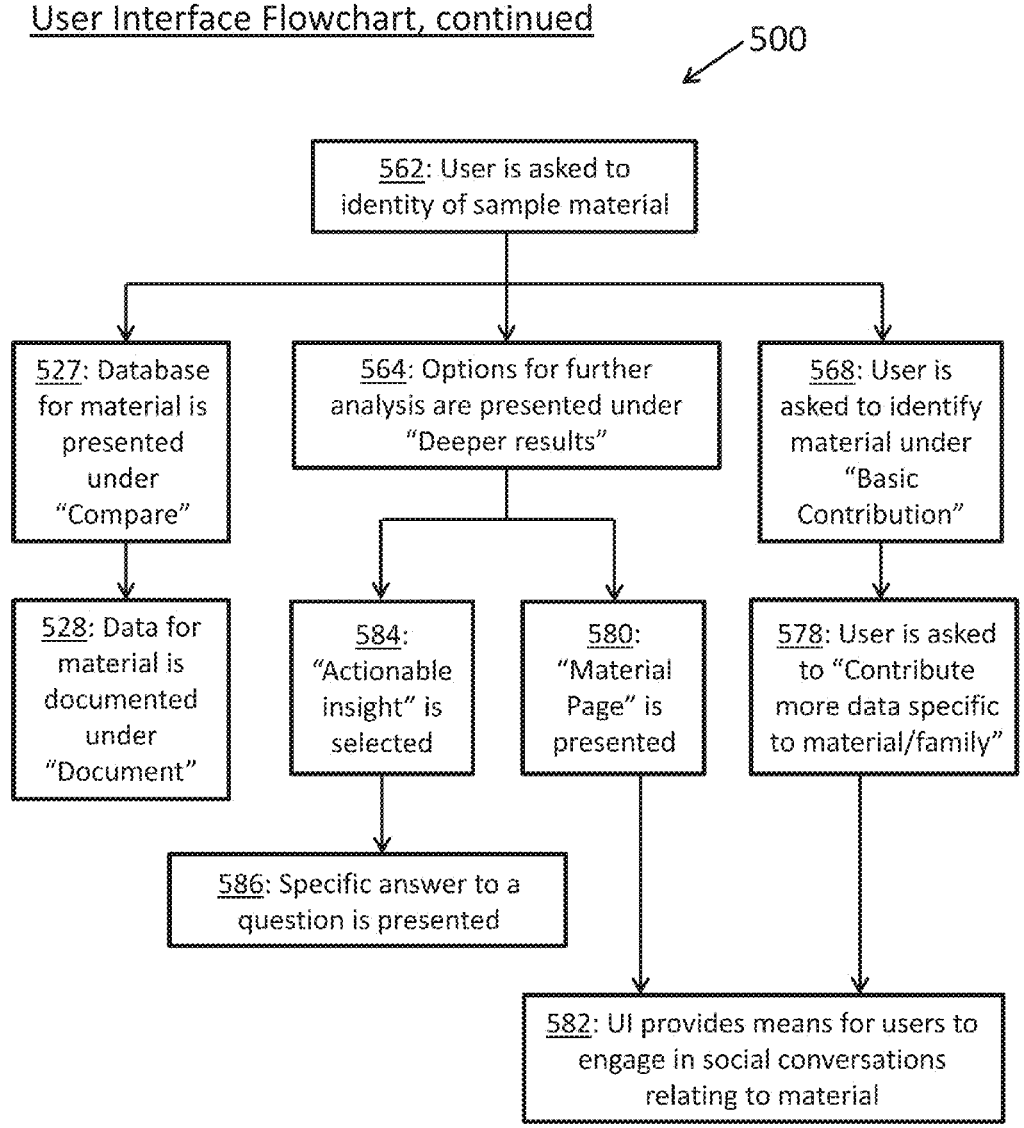

Now referring to FIG. 22E, at step 562, the "Confirm" 362 component of the UI is executed. At step 562, the user may be provided with the option of selecting one or more of "Compare" 327, "Deeper results" 364, or "Basic contribution" 368. At step 527, the "Compare" 327 component of the UI is executed, as described herein. At subsequent step 528, the "Document" 328 component of the UI is executed, as described herein. At step 564, the "Deeper results" 364 component of the UI is executed, as described herein. At step 564, the user may select between "Material page" 380 or "Actionable insight" 384. At step 584, the "Actionable insight" 384 component of the UI is executed, as described herein. At subsequent step 586, the "Specific answer to a question" 386 component of the UI is executed, as described herein. At step 580, the "Material page" 380 component of the UI is executed, as described herein. At subsequent step 582, the "People<-->Material" 382 component of the UI is executed, as described herein. At step 568, the "Basic contribution" 368 component of the UI is executed, as described herein. At subsequent step 578, the "Contribute more data specific to the material/family" 378 component of the UI is executed, as described herein. Subsequent to step 578, the user may be directed to step 582, as described herein.

Figure 22F:
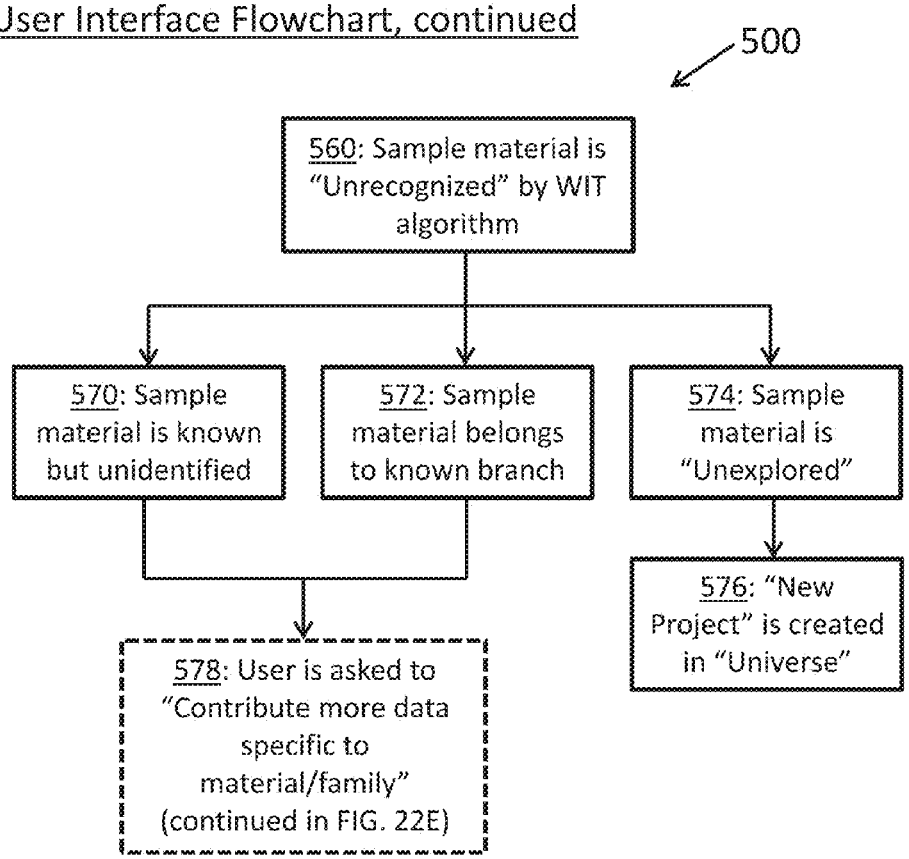

Now referring to FIG. 22F, at step 560, the "Unrecognized by WIT" 360 component of the UI is executed. At step 560, the user may be directed to one of the UI components "Known but unidentified material" 370, "Known branch" 372, or "Unexplored territory" 374. At step 370, the "Known but unidentified material" 370 component of the UI is executed, as described herein. At step 372, the "Known branch" 372 component of the UI is executed, as described herein. Subsequent to steps 370 or 372, the user may be directed to the component "Contribute more data" 378 in step 578, as described herein. At step 574, the "Unexplored territory" 374 component of the UI is executed, as described herein. At subsequent step 576, the "New project" 376 component of the UI is executed, as described herein.

Although the above steps show a method 500 of providing the UI 300 in accordance with embodiments, a person of ordinary skill in the art will recognize many variations based on the teachings described herein. The steps may be completed in a different order. Steps may be added or deleted. Some of the steps may comprise sub-steps of other steps. Many of the steps may be repeated as often as desired by the user.

Applications of the Compact Spectrometer System

The spectrometer system herein disclosed may be integrated into various devices and products across many industries. In order to facilitate the use of the system in various applications, the spectrometer system 100 may comprise a processor comprising instructions for performing various types of analyses for various applications. Some examples of these applications are described herein, but are in no way exhaustive.

Because of its small size and low cost, the spectrometer may be integrated into appliances commonly used in these various applications. For example, for food-related applications, the pocket size spectrometer may be integrated into kitchen appliances such as ovens (e.g. microwave ovens), food processors, and refrigerators. The user can then make a determination of the safety of the ingredients in real time during the course of food storage and preparation.

The spectrometer system disclosed herein may be used for agricultural applications. For example, the spectrometer system may be used to estimate the total solid solubles or "Brix" content in fruit. The pocket sized, hand-held spectrometer can easily be used to non-destructively measure the solid soluble content or water content of unpicked fruits, yielding information regarding the ripeness or firmness of the fruits. This will allow the farmer to monitor the fruits in a fast way and decide on appropriate picking time with no need to destroy products. Another example of an agricultural application for the spectrometer system is the field measurement of fertilization status of plants, such as grains, coffee, spinces, oil-seeds, or forage. The hand-held spectrometer can be used to obtain information about the fertilization status of the plant by non-destructively measuring the near infrared (NIR) spectrum of the plant. The spectral signature of components such as nitrogen, phosphate, and potash can be analyzed to provide the fertilization status per plant. The spectrometer system may also be used for field measurements of plant status. A pocket-sized spectrometer can allow on-line in-field spectrum analysis of the different parts of the plants, and can be used for early detection of plants stress and diseases development. The spectrometer system may also be useful for providing soil analysis. Fast in-field analysis of the soil spectrum using the hand-held spectrometer may provide a tool to monitor fertilization, watering, and salinity of the soil in many points in the field. Such an analysis can provide a powerful decision tool for farmers. The spectrometer may also be used for analyzing milk, for example for analyzing the fat or melamine content of the milk.

The spectrometer system disclosed herein may be used for home gardening applications. For example, the spectrometer may be used to analyze the water content in leaves. The pocket-size spectrometer can be used to obtain the spectra of the leaves, and the spectral signature of water can be used to estimate the water content in the leaves. Such a tool can give the user a direct access to the plant's watering status. As discussed above, the spectrometer system may also be used to analyze soil. The spectral signature of water, nitrogen, phosphate, and potash, and other relevant soil components can be detected by a pocket size spectrometer. By scanning the soil with the spectrometer, the user may be able to estimate the watering and fertilization status of the soil.

The spectrometer system disclosed herein may be used for pharmaceutical applications. For example, the spectrometer system may be used to identify pills. Scanning medications with pocket size spectrometer can reveal the unique spectral signature that each medication has. The pill may be placed in a close and adjusted cave to enhance the signal that is reflected from it, and an analysis of the pill may be performed. The spectral signature of the pill can provide an exact and reliable way to identify the pill, thus helping to prevent confusion between similar medications and/or the use of counterfeit medications. Another example of a pharmaceutical application of the spectrometer system is the identification of active ingredients levels in Cannabis. The active ingredients (e.g., tetrahydrocannabinol (THC), cannabidiol (CBD)) of cannabis can impose unique features on the spectral range of both the wet (unpicked) inflorescence and on its dried form. Scanning the inflorescence with the hand-held spectrometer can provide a fast and accurate estimation of the content of the active ingredients in the inflorescence.

The spectrometer system disclosed herein may be used in food analysis applications. For example, the spectrometer may be used to obtain nutrient information of food. Fats, carbohydrates, water, and proteins have detectable spectral signatures. Scanning the food with a pocket size spectrometer, in tandem with on-line analysis of the spectrum, can provide an immediate way to get the food's macro-nutrients estimation, including accurate estimation of its caloric value. Another example of a food analysis application for the spectrometer system is oil quality assurance. Detecting changes of the spectrum of cooking oils by scanning the oils with pocket size spectrometer can give the users access to chemical changes of the oxidation and acidity levels of the oil. Analysis of these changes can provide an immediate and accurate oil quality measurement. The spectrometer system may also be used to monitor food quality. Bacterial by-products and enzymatic processes can leave chemical traces in the food, which may have unique spectral signatures. Analyzing these chemical fingerprints by scanning the food with pocket size spectrometer can be used to detect these changes and provide information on the food's quality. The spectrometer system can also be used to determine the ripeness of fruits. Enzymatic processes and changes in the water content can be detected by scanning a fruit with pocket size spectrometer, giving an accurate estimation of the fruit's ripeness level. The spectrometer system can also be used for gutter oil identification. The fatty acids composition (FAC) of oils determines the oils' spectra. Thus, the spectrum of an oil can be used to identify the FAC and by that to identify the type of the oil. In particular gutter oil can be identified as different types of edible oils. A pocket size spectrometer with on-line spectrum analysis can thus be used to detect and identify gutter oils. The spectrometer system may also be used to ensure food safety. The existence of hazardous materials in food products can be detected by scanning the food with the spectrometer and analyzing the resultant spectrum. Similarly, the spectrometer can be used to determine pet food quality. The pocket size spectrometer can be used to analyze the content of pet-food, such as the amount of meat and macro-nutrients in the food. Analysis of the spectral signature of the food can verify the food content and quality.

The spectrometer system disclosed herein may also be used in gemology applications. For example, the spectrometer may be used in the authentication of gems. Gems have different spectra than look-alike counterfeits. Scanning a gem with spectrometer can verify the authenticity of the gem and provide its declared quality, by comparing the spectrum of the measured gem with the spectra of gems of known identity and quality, pre-loaded in the database. The spectrometer can be used to sort multiple gems according to their quality. The quality of gems can be determined by analyzing the gem's spectrum, since impurities and processing can affect the spectral signature of the gem. Scanning multiple gems with a pocket size spectrometer gems can enable a quick yet rigorous classification of the gems according to their spectra.

The spectrometer system disclosed herein may also be used in law enforcement applications. For example, the spectrometer may be used to identify explosives. A pocket size spectrometer can provide the law enforcement personnel with an immediate analysis of the spectrum of the potential explosives. The spectrum of the material in question can be compared to an existing database of spectra of explosive materials. Uploading the explosive's spectrum can be used to link explosives that were found in different times and places, because of the unique spectra of non-standard explosives. The spectrometer can also provide the law enforcement personnel a fast and accurate way to identify illegal drugs. This is done by analyzing the spectrum of the material in question and comparing the spectrum to an existing database of drug spectra. Uploading the sampled drug's spectrum can be used to link drugs identified in different cases, because of the unique spectra that the drugs may have (resulting, for example, from adulteration with powders, processing, etc.).

The spectrometer system disclosed herein may also be used in authentication applications. For example, the spectrometer may be used for the authentication of alcoholic beverages. Alcoholic beverages of different brands have unique chemical compositions, determined by the many factors including the source of the ingredients and the processing of the ingredients. A pocket size spectrometer can provide these unique chemical signatures, providing a fast authentication procedure for verifying an expected alcoholic beverage composition. For example, the spectrometer may be configured to detect an amount of methanol or gamma-hydroxybutyric acid present in a beverage. The user may scan the product, and the spectrum can be instantly analyzed and compared to spectra from a pre-loaded database, and within seconds a proof of originality can be provided. The spectrometer system may also be used to obtain infrared spectra of goods, to serve as proofs of originality.

The spectrometer system disclosed herein may also be used in healthcare applications. For example, the spectrometer may be used for body fat estimation. Total body fat may be estimated by measuring the thickness of the subcutaneous adipose tissue at various locations of the human body. This can be done by scanning the skin in various places with pocket size spectrometer, and analyzing the spectra. The spectrometer may also be used to identify dehydration. A direct, non-invasive measurement of fluid balance may be obtained by observing skin surface morphology, which is associated with water content. A pocket-sized spectrometer can be used to scan the skin surface and thereby continuously monitor the dehydration level. A pocket size spectrometer can also provide a fast way to measure blood components non-destructively. The spectrometer can scan the sample inside test tubes, preserving the samples for further laboratory analysis. Such an analysis can yield immediate results that may be less accurate than laboratory test results, but can be followed up and verified by the lab test results at a later time point. For example, hemoglobin analysis can be performed using a pocket size spectrometer, which can identify hemoglobin levels in blood by taking non-invasive scans of blood samples. The small size and ease of use of the spectrometer can enable a continuous monitoring of hemoglobin levels, alerting the user to sharp changes in the levels and potential anemia. The spectrometer can also be used for analyzing the skin for various properties. For example, scanning the skin with the spectrometer can provide a direct way to analyze lesions, wounds, moles and spots, allowing a user to examine skin issues like tissue hypoxia, deep tissue injury, melanoma, etc., from home. In addition, skin analysis using the spectrometer may provide cosmetic information that allows customization of cosmetic products. Similarly, the spectrometer may provide a way to analyze hair. Scanning the hair with a pocket size spectrometer can provide valuable information about the hair (type, condition, damage, etc.) that can be used to customize cosmetic products like shampoo, conditioner, or other hair products.

Figure 23:
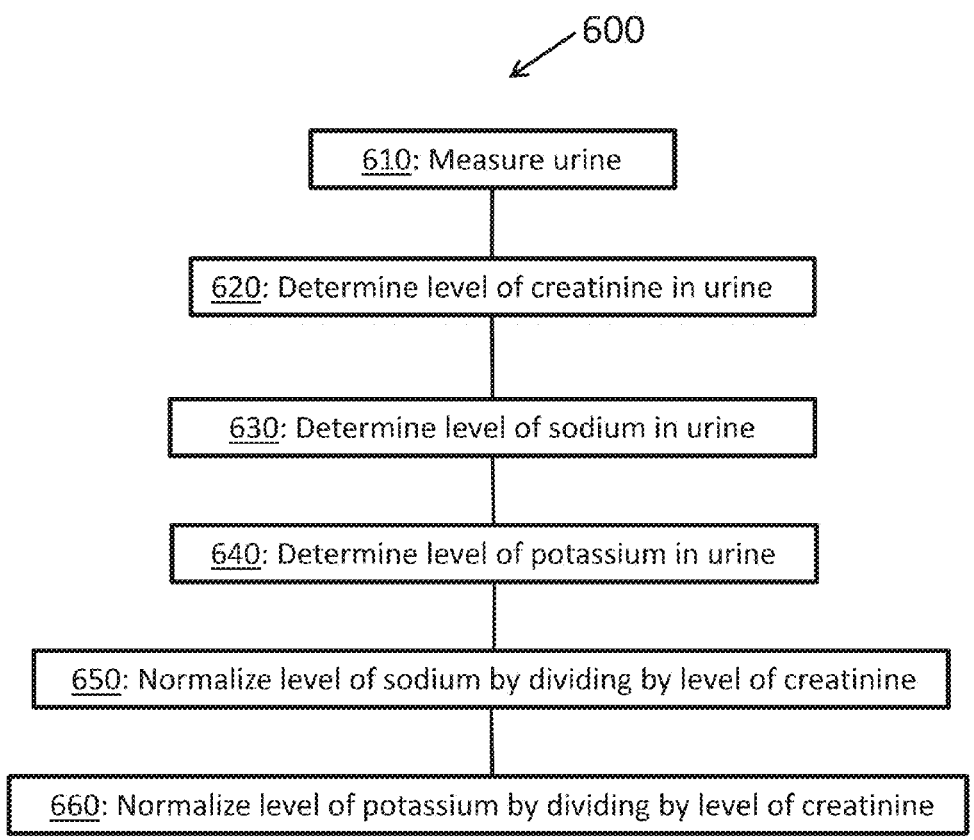
FIG. 23 shows a method for performing urine analysis using a spectrometer system in accordance with embodiments.

The spectrometer may also be used for urine analysis at home. A spectrometer as disclosed herein may allow an immediate analysis of various solutes in the urine such as sodium, potassium, creatinine, and urea. In particular, a method 600 of urine salt analysis, as shown in FIG. 23, can be a useful tool for monitoring blood pressure. High blood pressure may be correlated with high levels of oral sodium intake, which can lead to high levels of sodium and potassium in the urine. However, an accurate determination of sodium intake via urine analysis can be difficult, as the absolute levels of sodium and potassium in the urine may be affected by confounding factors such as the volume of fluids consumed. In order to determine the levels of sodium and potassium in the urine that are truly correlated with sodium intake, measured levels of sodium and potassium may be normalized by measured levels of creatinine in the urine. For example, at step 610, a urine sample may be scanned using the spectrometer system described herein. At step 620, the spectrometer system may determine the level of creatinine in the urine based on the light spectrum of the urine sample. Similarly, at step 630, the spectrometer system may determine the level of sodium in the urine; at step 640, the spectrometer system may determine the level of potassium in the urine. At step 650, the level of sodium may be normalized, by dividing by the level of creatinine; similarly, at step 660, the level of potassium may be normalized, by dividing by the level of creatinine. The user interface may present to the user creatinine-normalized sodium and potassium levels in the urine, as indicators of the user's sodium intake. A spectrometer system configured to perform urine analysis methods such as method 600 can enable the continuous monitoring of urine solutes from home, as a way of monitoring related health conditions such as high blood pressure. The method 600 of urine salt analysis may also be performed using an electro-chemical sensor comprising parts of the spectrometer system described herein. The spectrometer or electro-chemical sensor may be embedded in a urinal and/or a toilet, in order to perform urine analysis as described herein.

The spectrometer system disclosed herein may also be used for fuel quality monitoring. For example, the spectrometer may be used to determine a type of fuel, a contaminant level, octane level, cetane level, or other substance composition. The spectrometer system for such applications may be configured for integration with a vehicle component. The vehicle component may be a fuel system component, such as a fuel tank, fuel line, or fuel injector of the vehicle.

The spectrometer system disclosed herein may also be used for monitoring power components. For example, the spectrometer may be used to determine the condition associated with a fluid of a power converting component.

Experimental Data

Figure 24:
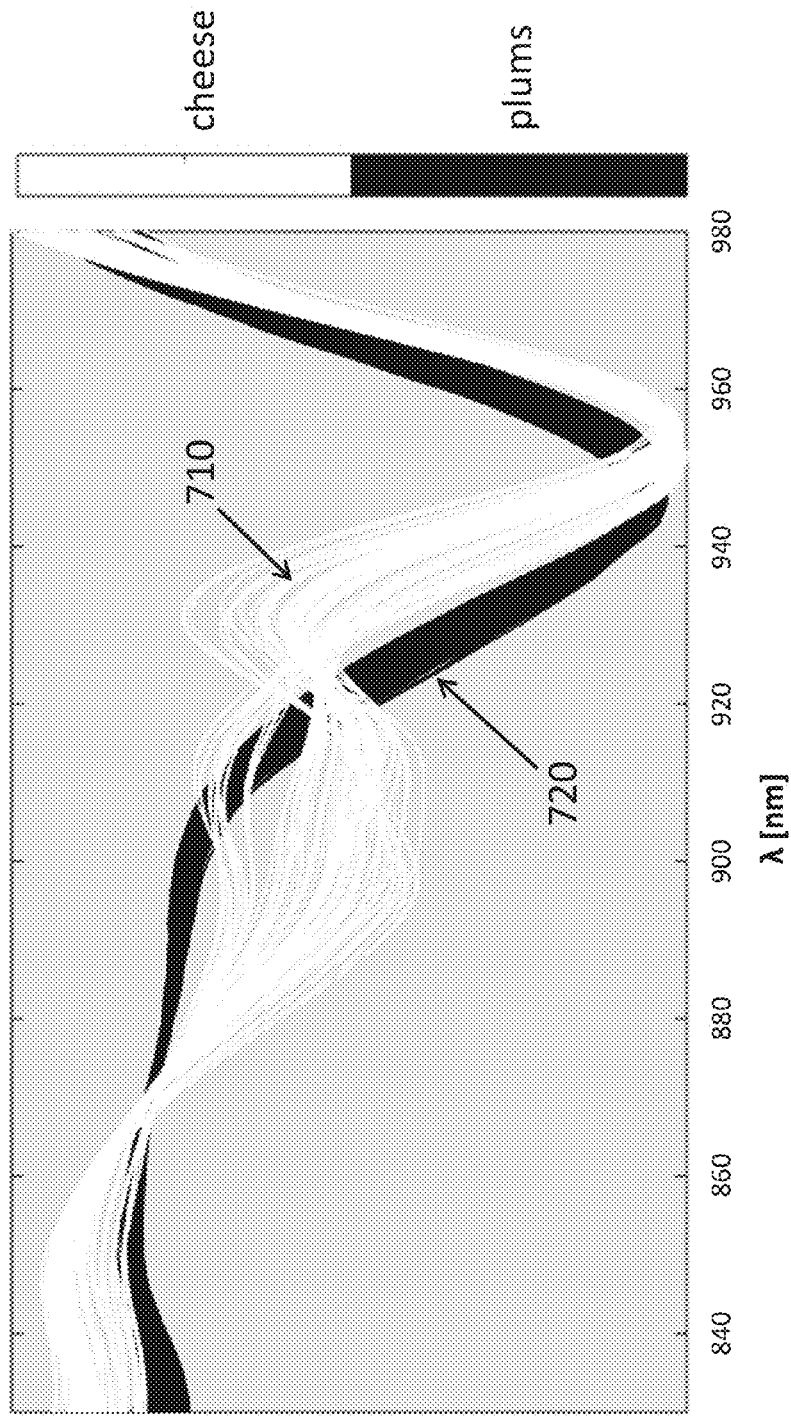
FIG. 24 shows exemplary spectra of plums and cheeses, suitable for incorporation in accordance with embodiments.

FIG. 24 shows exemplary spectra of plums and cheeses, suitable for incorporation in accordance with embodiments. The spectra of various cheeses 710 and the spectra of various plums 720 are shown to have characteristic features specific to the material type. Characteristic features include, for example, the general shape of the spectra, the number of peaks and valleys in the spectra within a certain wavelength range, and the corresponding wavelengths or wavelength ranges of said peaks and valleys of the spectra. Based on such characteristic features, a spectrometer system as described herein can determine the general identity (e.g., "cheese", "plum") of a sampled material, by comparing the measured spectral data against the spectral data of various materials stored in the universal database, as described herein. While FIG. 24 shows the spectra of plums and cheeses in the wavelength range of about 830 nm to about 980 nm, the spectra may be analyzed at any wavelength range that comprises one or more differences between the characteristic features of the spectra of the different materials.

Figure 25:
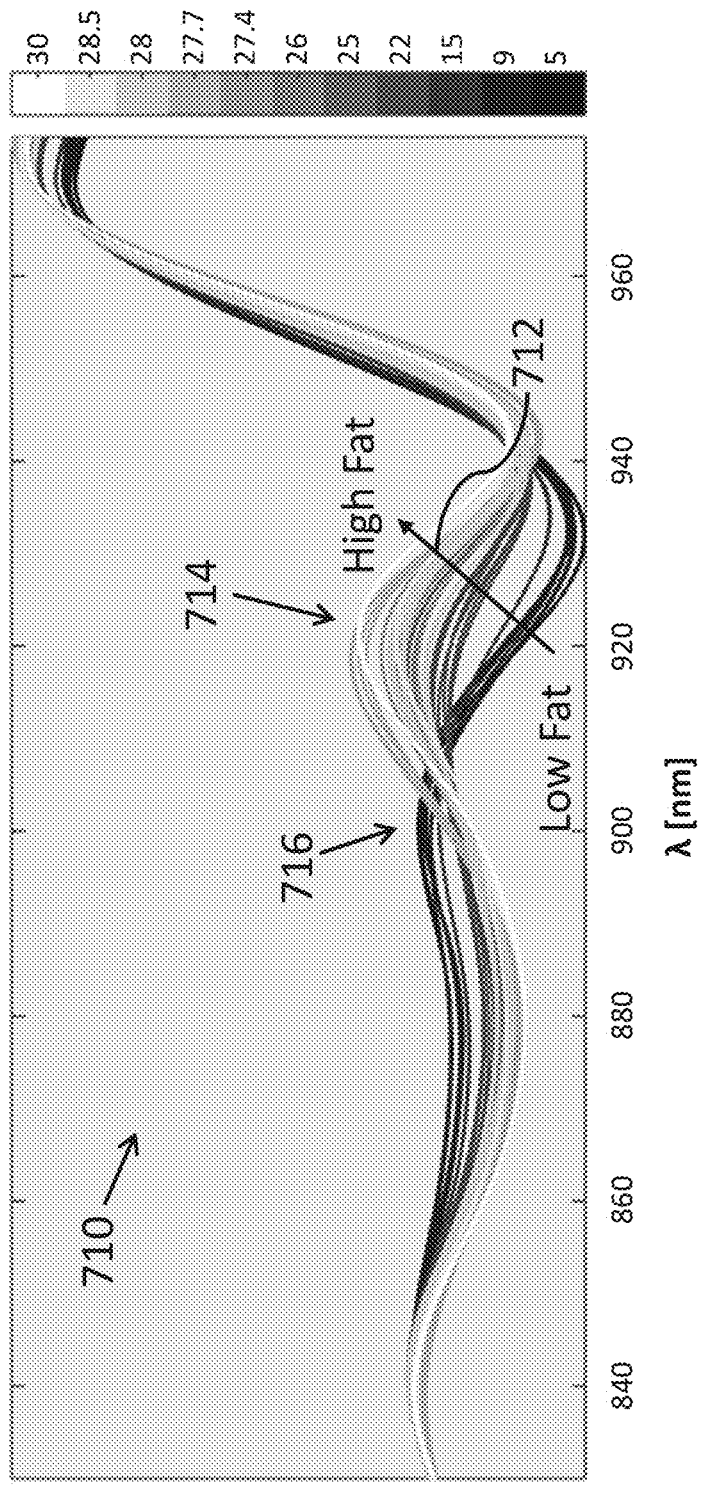
FIG. 25 shows exemplary spectra of cheeses comprising various fat levels, suitable for incorporation in accordance with embodiments.

FIG. 25 shows exemplary spectra of cheeses comprising various fat levels, suitable for incorporation in accordance with embodiments. The spectra share general characteristic features in the wavelength range of about 840 nm to about 970 nm that enable their identification as spectra of cheeses 710, but also have differences in their features that correspond to differences in the fat levels of the measured cheeses. In the spectra shown in FIG. 25, the spectra trend from having relatively lower fat content to relatively higher fat content in the direction indicated by arrow 712. For example, the spectra of cheeses having higher fat levels tend to have more distinct secondary peaks 714 compared to the secondary peaks 716 of the spectra of cheeses having lower fat levels. The secondary peaks 714 of the high-fat cheeses also tend to be shifted to the right (i.e., to higher wavelengths) compared to the secondary peaks 716 of the low-fat cheeses; in FIG. 25, the secondary peaks 714 of the high-fat cheeses are centered at around 920 nm, whereas the secondary peaks 716 of the low-fat cheeses are centered at around 900 nm.

Figure 26:
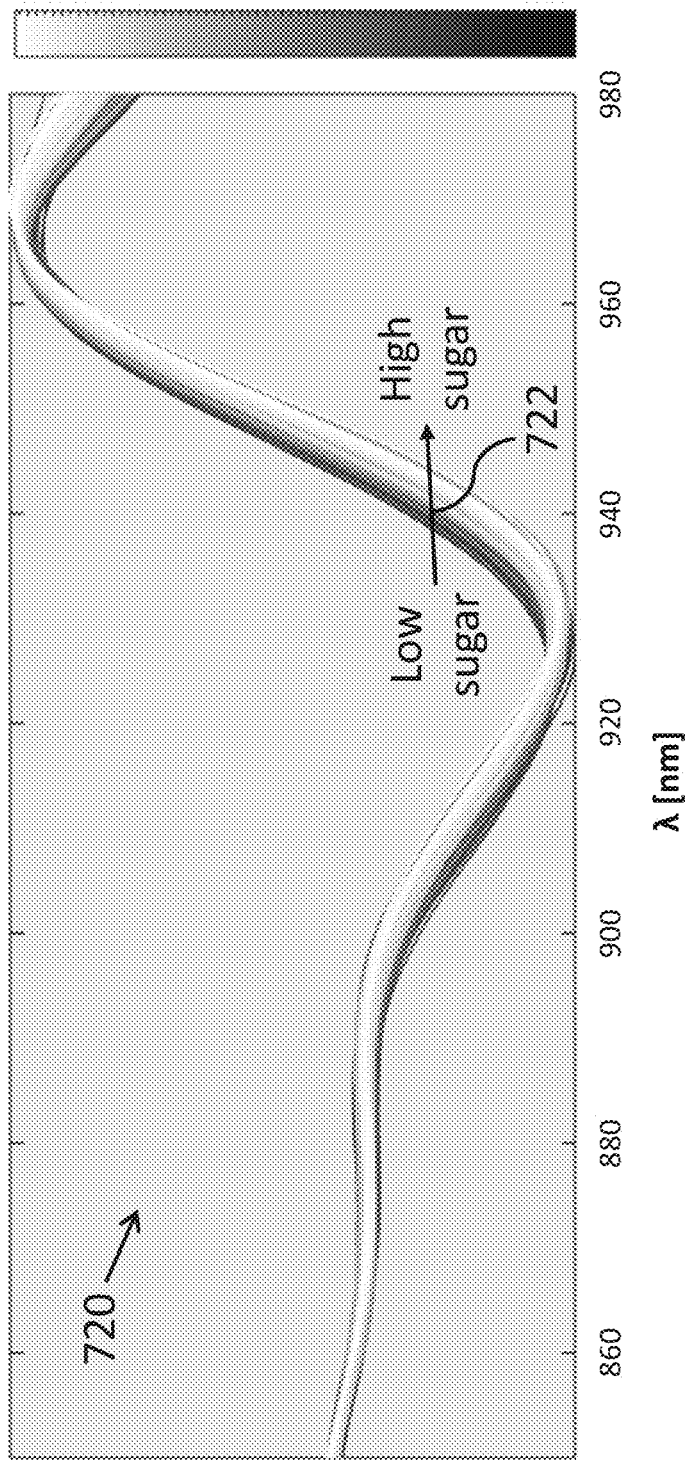
FIG. 26 shows exemplary spectra of plums comprising various sugar levels, suitable for incorporation in accordance with embodiments.

FIG. 26 shows exemplary spectra of plums comprising various sugar levels, suitable for incorporation in accordance with embodiments. The spectra share general characteristic features in the wavelength range of about 860 nm to about 980 nm that enable their identification as spectra of plums 720, but also have differences in their features that correspond to differences in the sugar levels of the measured plums. In the spectra shown in FIG. 26, the spectra trend from having relatively lower sugar content to relatively higher sugar content in the direction indicated by arrow 722. For example, the spectra of plums having higher sugar levels tend to be shifted to the right (i.e., to higher wavelengths) by approximately 5-7 nm compared to the spectra of plums having lower sugar levels.

As shown in FIGS. 25 and 26, differences in one or more spectral features among spectra of the same general material type can provide information regarding the different levels of sub-components (e.g., fat, sugar) of the material. The spectrometer system as described herein may identify such differences by comparing the measured spectral data against the spectral data of a specific material type stored in the universal database, and provide the user with information regarding the composition of the measured material.

Figure 27:
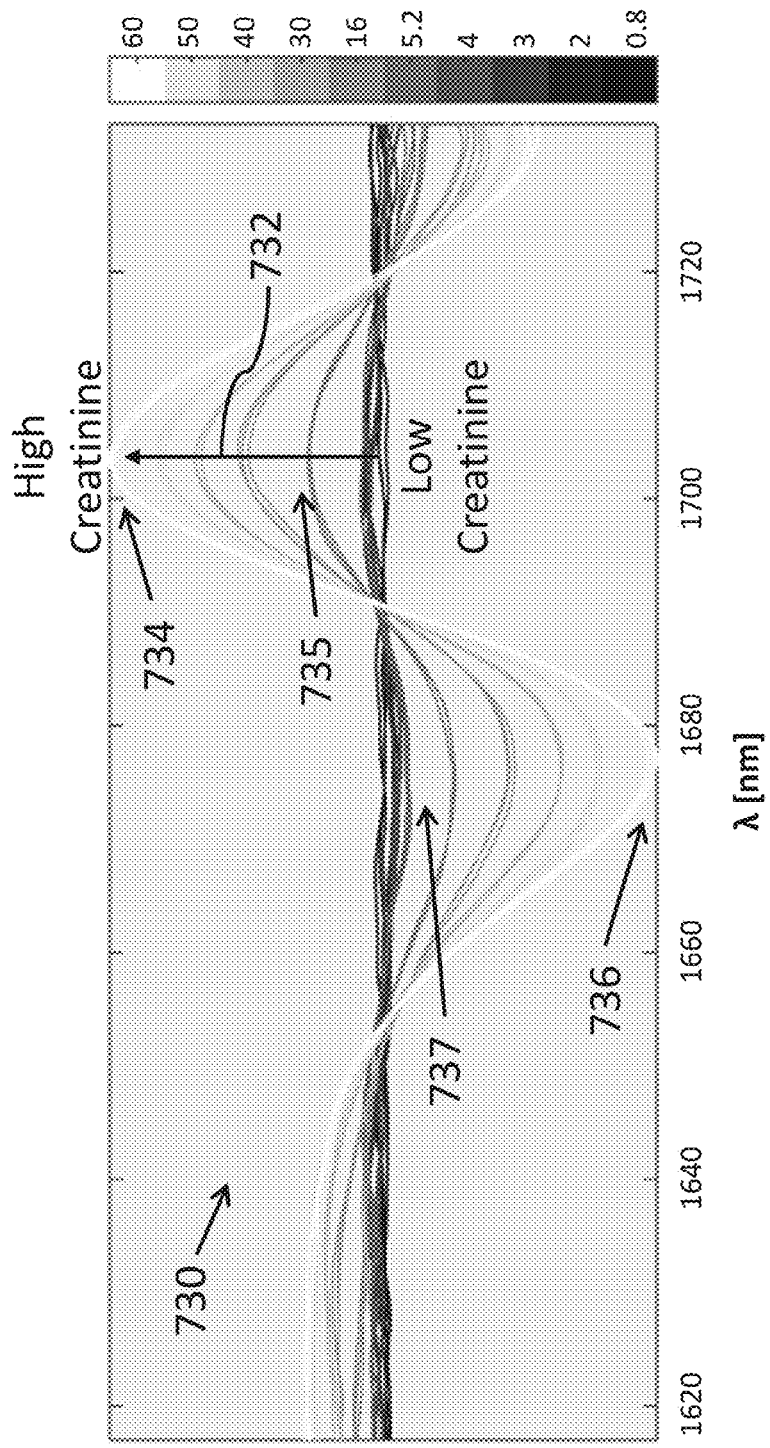
FIG. 27 shows exemplary spectra of aqueous solutions comprising various levels of creatinine, suitable for incorporation in accordance with embodiments.
Figure 28:
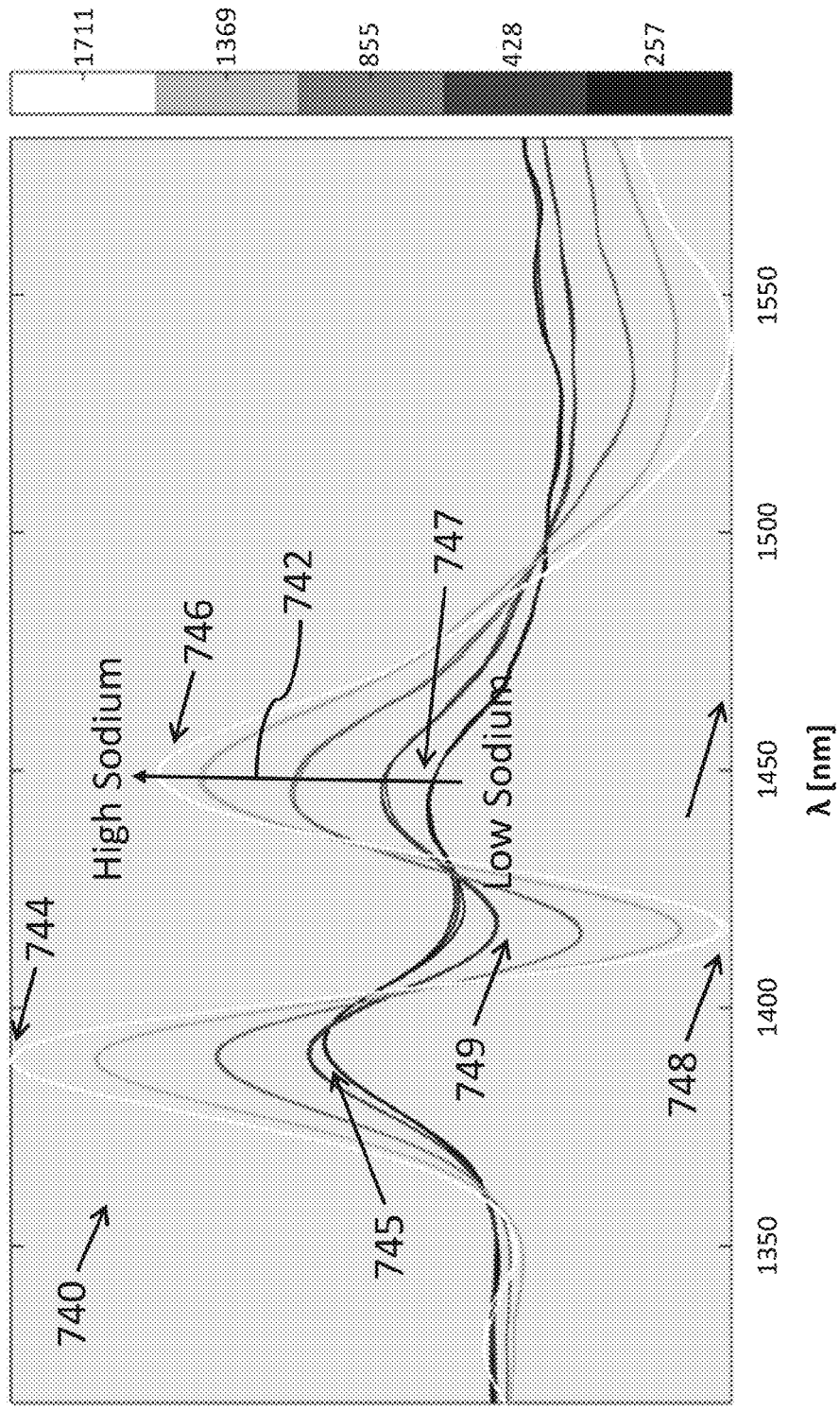
FIG. 28 shows exemplary spectra of aqueous solutions comprising various levels of sodium, suitable for incorporation in accordance with embodiments.
Figure 29:
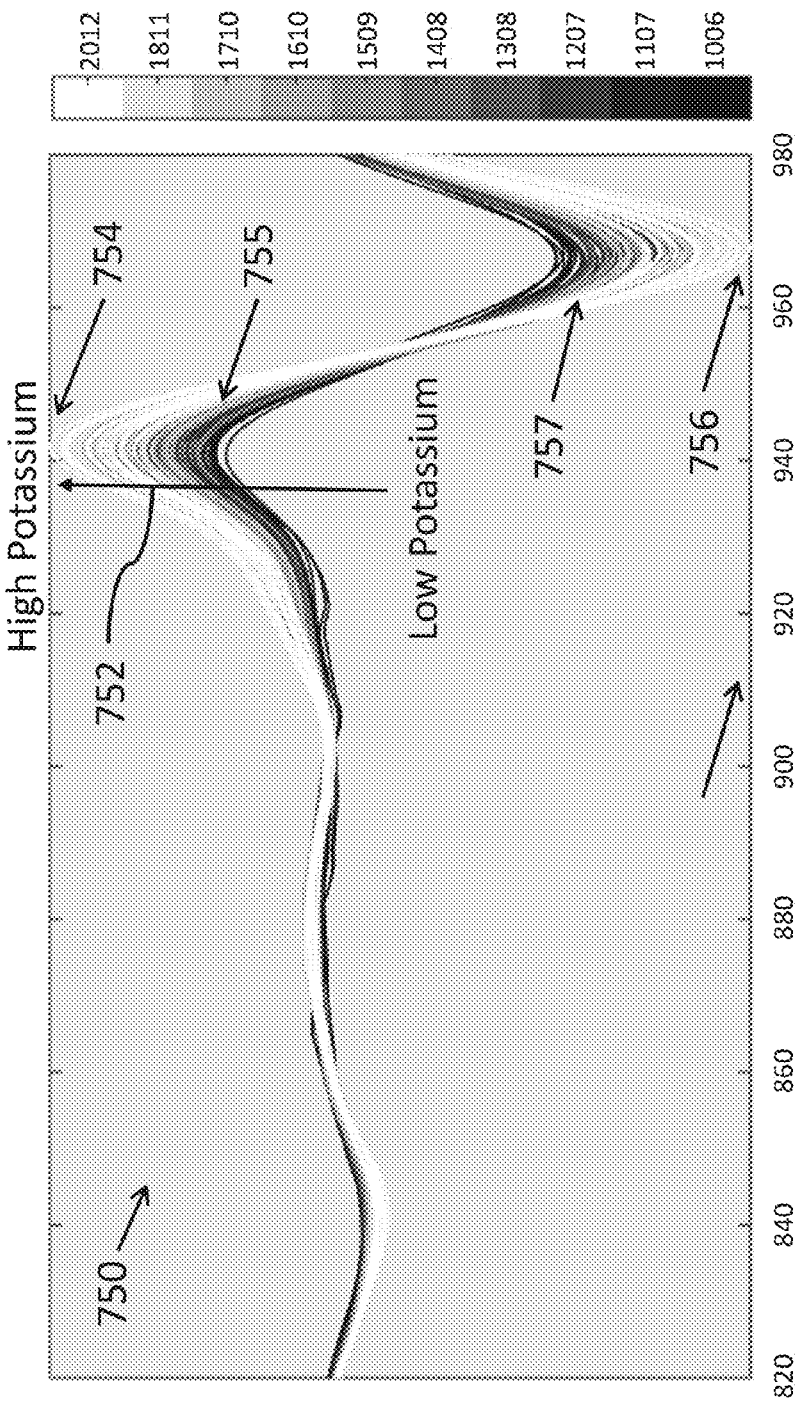
FIG. 29 shows exemplary spectra of aqueous solutions comprising various levels of potassium, suitable for incorporation in accordance with embodiments.

FIGS. 27-29 show exemplary spectra of various components of urine in an aqueous solution, suitable for incorporation into a method of urine analysis in accordance with embodiments. For example, the spectrometer system may be used to detect the levels of creatinine, sodium, and potassium in a sample of urine, and the sodium and potassium levels may be normalized with respect to the creatinine levels in order to provide a meaningful measure of the user's salt intake. Such a method for urine analysis using the spectrometer system is described in further detail herein with reference to FIG. 23.

FIG. 27 shows exemplary spectra of aqueous solutions comprising various levels of creatinine, suitable for incorporation in accordance with embodiments. The spectra share general characteristic features in the wavelength range of about 1620 nm to about 1730 nm that enable their identification as spectra of solutions containing creatinine 730, but also have differences in their features that correspond to differences in the relative levels of the measured creatinine. In the spectra shown in FIG. 27, the spectra trend from having relatively lower creatinine levels to relatively higher creatinine levels in the direction indicated by arrow 732. For example, the spectra of solutions having higher levels of creatinine tend to have higher peaks 734, centered at about 1703 nm, compared to the corresponding peaks 735, also centered at about 1703 nm, of the spectra of solutions having lower levels of creatinine. Also, the spectra of solutions having higher levels of creatinine tend to have lower valleys 736, centered at about 1677 nm, compared to the corresponding valleys 737, also centered at about 1677 nm, of the spectra of solutions having lower levels of creatinine.

FIG. 28 shows exemplary spectra of aqueous solutions comprising various levels of sodium, suitable for incorporation in accordance with embodiments. The spectra share general characteristic features in the wavelength range of about 1350 nm to about 1550 nm that enable their identification as spectra of solutions containing sodium 740, but also have differences in their features that correspond to differences in the relative levels of the measured sodium. In the spectra shown in FIG. 28, the spectra trend from having relatively lower sodium levels to relatively higher sodium levels in the direction indicated by arrow 742. For example, the spectra of solutions having higher levels of sodium tend to have higher peaks 744 (centered at about 1388 nm) and 746 (centered at about 1450 nm) compared to the corresponding peaks 745 (centered at about 1390 nm) and 747 (centered at about 1444 nm) of the spectra of solutions having lower levels of sodium. Also, the spectra of solutions having higher levels of sodium tend to have lower valleys 748 (centered at about 1415 nm) compared to the corresponding valleys 749 (centered at about 1415 nm) of the spectra of solutions having lower levels of sodium.

FIG. 29 shows exemplary spectra of aqueous solutions comprising various levels of potassium, suitable for incorporation in accordance with embodiments. The spectra share general characteristic features in the wavelength range of about 820 nm to about 980 nm that enable their identification as spectra of solutions containing potassium 750, but also have differences in their features that correspond to differences in the relative levels of the measured sodium. In the spectra shown in FIG. 29, the spectra trend from having relatively lower potassium levels to relatively higher potassium levels in the direction indicated by arrow 752. For example, the spectra of solutions having higher levels of potassium tend to have higher peaks 754 (centered at about 942 nm) compared to the corresponding peaks 755 (centered at about 942 nm) of the spectra of solutions having lower levels of potassium. Also, the spectra of solutions having higher levels of potassium tend to have lower valleys 756 (centered at about 968 nm) compared to the corresponding valleys 757 (centered at about 968 nm) of the spectra of solutions having lower levels of potassium.

As shown in FIGS. 27-29, differences in one or more spectral features among spectra of solutions having similar general compositions (e.g., creatinine, sodium, potassium) can provide a means for obtaining a relative measurement of the level of each component. The spectrometer system as described herein may identify such differences by comparing the measured spectral data against the spectral data for a specific material component stored in the universal database, and provide the user with information regarding the composition of the measured sample.

The spectra of cheeses shown in FIGS. 24 and 25 have been acquired using a spectrometer system and device in accordance with embodiments. The spectra of plums, shown in FIGS. 24 and 26, and the spectra of creatinine, sodium, and potassium in aqueous solutions, shown in FIGS. 27-29, show spectra suitable for incorporation in accordance with embodiments described herein, and a person of ordinary skill in the art can configure the spectrometer to make suitable spectral measurements without undue experimentation. For example, in order to provide measurements of creatinine levels as described herein, the spectrometer device may be configured to comprise a combination of the various optical structures disclosed herein. One such exemplary configuration may comprise a filter-based optics structure as described herein, combined with multiple illumination sources as described herein. Another exemplary configuration may comprise modifying the filter-based optics structure disclosed herein to enable its detection of a lower-intensity signal of creatinine that falls within the detected wavelength range of the optical system. Alternatively or in combination, a substance may be added to urine samples to increase the signal intensity of the samples at the wavelength ranges detected by the optical systems described herein.

In many embodiments, the processor of the spectrometer system can be configured with instructions to perform specific steps in order to provide actionable insights or information to the user. For example, for the urine analysis method as described herein, the processor may be configured to compare the ratio of sodium to creatinine, in order to normalize the results presented to the user.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the method and apparatus of the present disclosure provided herein without departing from the spirit and scope of the invention as described herein.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. An apparatus comprising:
a remote server comprising instructions to receive spectral data from a spectrometer and a unique identification of the spectrometer,
a plurality of unique identifications for a plurality of spectrometers, and
calibration data for each of the plurality of spectrometers, said calibration data for each of the plurality of spectrometers associated with one of the plurality of unique identifications.

2. An apparatus as in claim 1, wherein the remote server comprises a centralized cloud based server configured to receive respective spectral data from the plurality of spectrometers and to transmit object data to the plurality of spectrometers in response to the calibration data.

3. An apparatus as in claim 1, wherein the remote server comprises instructions to determine a calibrated spectrum in response to the spectral data, the unique identification of the spectrometer, and the calibration data at the remote server associated with the unique identification, the remote server comprising instructions to transmit object data to a mobile communication device in response to the calibrated spectral data.

4. An apparatus as in claim 1, wherein the remote server is configured to
receive one or more of the spectral data, an ambient temperature measured with a mobile communication device, a temperature of an object, the unique identification of the spectrometer, or compressed spectral data from the mobile communication device coupled to the spectrometer,
determine a calibrated spectrum in response to the one or more of the ambient temperature measured with the mobile communication device, the temperature of the object, the unique identification of the spectrometer, or the compressed spectral data from the mobile communication device coupled to the spectrometer,
determine an object data in response to the calibrated spectrum, and output the object data to the mobile communication device.

5. An apparatus as in claim 1, wherein the remote server comprises instructions to,
receive spectrometer and mobile communication device data from a plurality of the mobile communication devices coupled to the plurality of spectrometers,
store the spectrometer and mobile communication device data from the plurality of mobile communication devices coupled to the plurality of spectrometers on a database of the remote server, and
share the spectrometer and mobile communication device data of the database among the plurality of mobile communication devices.

6. An apparatus as in claim 1, wherein a mobile communication device data comprises one or more of a location of the spectral data when measured, a store associated with the location of the spectral data when measured, a time of the spectral data, a date of the spectral data, a temperature associated with the spectral data, or a user input indicating a type of an object as a member of a class of object types.

7. An apparatus as in claim 1, comprising a processor, wherein said processor comprises instructions to display on a mobile communication device a type of object, a map showing spectral data of similar objects, or an indication of status of the similar objects based on the spectral data of the similar objects.

8. An apparatus as in claim 7, wherein the processor comprises instructions to download a map of attributes derived from spectral data of a plurality of spectrometers, the map having locations on the map, and a location of a store, and wherein the processor comprises instructions for a user interface configured for a user to click on the store and display object data in response to spectral data for objects of a type selected by the user.

9. An apparatus as in claim 8, wherein the processor is configured with instructions to display a time profile of the object data in response to spectral data for the type of object at the store over time.

10. An apparatus as in claim 8, wherein the processor is configured with instructions to display a plurality of time lines comprising a plurality of object data profiles in response to spectral data for a plurality of types of objects at a location with one or more pop up windows associated with the location.

11. An apparatus as in claim 10, wherein the plurality of object data profiles comprises graphic profiles shown on a display corresponding to one or more of fruit or dairy products, and corresponding amounts of one or more of sweetness or fat.

12. An apparatus as in claim 7, wherein the processor comprises instructions to
determine a solid soluble content of an unpicked fruit.

13. An apparatus as in claim 7, wherein the processor comprises instructions to
determine a fertilization status of an unpicked plant with non-destructive measurement of a near infrared spectrum of the unpicked plant or soil near the unpicked plant in response to a spectral signature of one or more of nitrogen, phosphate, or potash.

14. An apparatus as in claim 7, wherein the processor comprises instructions to
determine an on-line in-field spectrum analysis of different parts of plants in order to provide early detection of stress of the plants and detection disease development.

15. An apparatus as in claim 7, wherein the processor comprises instructions to
monitor one or more of fertilization, watering or salinity of soil at many points in a field along with measurement location data in the field.

16. An apparatus as in claim 7, wherein the processor comprises instructions to
determine water content of leaves of a plant in response to a spectral signature of water and display the water content to a user in order to provide a watering status of the plant to the user.

17. An apparatus as in claim 7, wherein the processor comprises instructions to
determine a water and fertilization status of soil and to display the water and fertilization status to a user.

18. An apparatus as in claim 7, wherein the processor comprises instructions to
identify a pill in response to a spectral signature of one or more of a medication of the pill or a coating of the pill.

19. An apparatus as in claim 7, wherein the processor comprises instructions to
identify one or more explosives in response to spectral data of the object and link explosives identified at different places and times.

20. An apparatus as in claim 7, wherein the processor comprises instructions to
identify one or more drugs in response to spectral data of the object.

* * * * *